US010519192B2

(12) United States Patent
Rathbone et al.

(10) Patent No.: US 10,519,192 B2
(45) Date of Patent: Dec. 31, 2019

(54) COMPOUND FOR TREATING CLOSTRIDIUM DIFFICILE

(71) Applicant: Aston University, Birmingham (GB)

(72) Inventors: Daniel Lee Rathbone, West Midlands (GB); Tony Worthington, West Midlands (GB); Sahar Al-Malaika, West Midlands (GB); Matthew Justin Hird, Cambridgeshire (GB); Alexandria Rose Quayle, Derbyshire (GB)

(73) Assignee: INSIGHT HEALTH LIMITED, Middlesex (GB)

( * ) Notice: Subject to any disclaimer, the term of this patent is extended or adjusted under 35 U.S.C. 154(b) by 0 days.

(21) Appl. No.: 15/528,475

(22) PCT Filed: Nov. 26, 2015

(86) PCT No.: PCT/GB2015/053614
§ 371 (c)(1),
(2) Date: May 19, 2017

(87) PCT Pub. No.: WO2016/083819
PCT Pub. Date: Jun. 2, 2016

(65) Prior Publication Data
US 2017/0320906 A1 Nov. 9, 2017

(30) Foreign Application Priority Data
Nov. 27, 2014 (GB) ..................... 1421071

(51) Int. Cl.
*A61K 31/575* (2006.01)
*A61K 31/58* (2006.01)
*A61K 45/06* (2006.01)
*A61K 47/54* (2017.01)
*C07J 43/00* (2006.01)
*C07J 9/00* (2006.01)
*C07J 41/00* (2006.01)
*C08F 293/00* (2006.01)

(52) U.S. Cl.
CPC ........... *C07J 43/003* (2013.01); *A61K 31/575* (2013.01); *A61K 31/58* (2013.01); *A61K 45/06* (2013.01); *A61K 47/554* (2017.08); *C07J 9/005* (2013.01); *C07J 41/0061* (2013.01); *C08F 293/005* (2013.01)

(58) Field of Classification Search
CPC ...... C07J 43/003; C07J 9/005; C07J 41/0061; A61K 47/554; A61K 31/575; A61K 31/58; A61K 45/06; C08F 293/005
See application file for complete search history.

(56) References Cited
U.S. PATENT DOCUMENTS

2014/0045808 A1\* 2/2014 Abel-Santos ........ C07J 41/0061
514/182

FOREIGN PATENT DOCUMENTS

WO 2008/156636 A1 12/2008
WO 2014/084421 A1 6/2014

OTHER PUBLICATIONS

Birikaki, Lemonia, Written Opinion of the International Searching Authority, European Patent Office, PCT/GB2015/053614, dated Feb. 15, 2016.
Birikaki, Lemonia, International Search Report, European Patent Office, PCT/GB2015/053614, dated Feb. 15, 2016.
Vatmurge et al., "Synthesis and antimicrobial activity of beta-lactambile acid conjugates linked via triazole," Bioorganic & Medicinal Chem. Lett., vol. 18, No. 6, pp. 2043-2047, Mar. 2008.
Bhat et al., "Low molecular mass cationic gelators derived from deoxycholic acid: remarkable gelation of aqueous solvents," Tetrahedron, 63:7309-7320, 2007.
Suan et al., "Preparation and Characterization of Cholic Acid-Derived Antimicrobial Agents with Controlled Stabilities," Organic Letters, 2(18):2837-3840, 2000.
Kagedahl et al., "Use of the Intestinal Bile Acid Transporter for the Uptake of Cholic Acid Conjugates with HIV-1 Protease Inhibitory Activity," Pharmaceutical Research, 14(2):176-180, 1997.
Sharma et al., "Ursodeoxycholic Acid Amides As Novel Glucocorticoid Receptor Modulators," J. Med. Chem., 54:122-130, 2011.
Birikaki, Lemonia, Communication Pursuant to Article 94(3) EPC, European Patent Office, Application No. 15804919.7, dated Nov. 26, 2018.
Cravotto et al., "Chemical notifications of bile acids under high-intensity ultrasound or microwave irradiation", Steroids, 70, 2005, pp. 77-83.
Birikari, Lemonia. Examination Report Issued by European Patent Office for EP Appl. No. 15804919.7, dated Oct. 16, 2019.
Quayle, Alexandria Rose. "Preparation of Dual-action Germinant-Biocide Smart Polymer and Soluble Agent for the Elimination of C. Difficile Spores" Thesis, Aston University, Jun. 2013.

(Continued)

*Primary Examiner* — Robert H Havlin
(74) *Attorney, Agent, or Firm* — Gavrilovich, Dodd & Lindsey LLP

(57) ABSTRACT

The invention relates to compounds, compositions and polymers comprising a first component adapted to promote germination of *Clostridium difficile* (*C.diff*) and a second component which acts as an antimicrobial agent. Said compounds, compositions and polymers are useful for destroying *C.diff* where conventional antimicrobial agents are unsuccessful. The compositions can be formulated as coating or materials which actively destroy *C.diff* which come into contact with it. The germination promotion is induced by bile salts. The invention also relates to the use of such materials as a treatment for *C.diff* associated diseases and toxic megacolon.

3 Claims, 2 Drawing Sheets

(56) References Cited

OTHER PUBLICATIONS

Walker, Susan M. Statement of Fact and Exhibits A, B, and C: in regards to the publicly availability date of Quayle thesis. Nov. 8, 2019.
Willemen et al. "Alkyl Derivatives of Cholic Acid as Organogelators: One-Component and Two-Component Gels" Langmuir 18:7102-7106 (2002).

* cited by examiner

COMPOUND FOR TREATING CLOSTRIDIUM DIFFICILE

CROSS REFERENCE TO RELATED APPLICATIONS

This application is a U.S. National Stage Application filed under 35 U.S.C. § 371 and claims the benefit of International Application No. PCT/GB2015/053614, filed Nov. 26, 2015, which claims priority under 35 U.S.C. § 119 to Great Britain Application No. 1421071.0, filed Nov. 27, 2014, the disclosures of which are incorporated herein by reference.

FIELD OF INVENTION

The invention relates to a compound suitable for the treatment of *Clostridium Difficile* (*C.diff.*) and in particular, the use of conjugated bile salts and polymers comprising bile salts.

BACKGROUND TO THE INVENTION

The spore forming bacterium *Clostridium Difficile* (*C. diff.*) is known to cause a variety of problems in the human body and particularly in the human digestive system. The bacterium in its spore form is extremely resilient to antimicrobial agents as well as other forms of chemical and physical treatments. These *C. diff.* spores are capable of surviving the harsh acidic conditions within the stomach and can end up in the intestines of the body.

Once in the intestine, typically the large intestine, *C. diff.* spores are able to germinate into the more active bacterial species which secretes harmful toxins which cause illness such as pseudo-membranous colitis or even toxic megacolon.

In order to destroy such spores outside the body, for example where the spores are present on surfaces, strong chemical cleaning agents such as bleach are required. This is undesirable as such cleaning agents (often used in high concentrations) are more difficult to handle compared to standard antibacterial treatments and also can not be used on the skin.

However, the most significant problem with *C. diff.* infection appears to be where a patient has contracted another, accompanying bacterial infection and is treated with antibiotics, especially broad-spectrum antibiotics. The antibiotics destroy not only the target bacteria for which the antibiotics were prescribed, but also significantly reduce the amount of bacteria present in the gut. As *C. diff.* in its spore form typically resist attack by antibiotics, this leads to a situation where *C. diff.* spores can enter the gut, germinate into the more active bacterial species, and can thrive as there is little in the way of competition from native gut bacteria.

These problems mean that *C. diff.* can be a significant problem in hospitals and healthcare facilities where many patients are undergoing or have recently completed a course of antibiotics and where healthcare professions, although diligent in their use of antimicrobial cleaning products to destroy conventional microbes present on their person in between patient interactions, may still transmit *C. diff.* spores to many individuals.

Current treatments for *C. diff.* infections include administration of antibiotics but patients often experience relapses, possibly because the antibiotics are only capable of treating the germinated *C. diff.* bacteria not any residual ungerminated spores. Alternative treatments include performing a stool transplant in order to re-establish the bacterial environment of the gut, thereby reducing the amount of *C. diff.* bacteria due to increased competition for nutrients with the transplanted bacteria. However, this procedure is not an attractive option for many patients.

Extensive research has been performed to examine what causes germination of *C. diff.* spores. Wilson K (J. Clin Microbial 1983 1017-1019) states that the presence of certain bile salts appears to trigger germination of *C. diff.* spores in the large intestine. Other sources such as Sorg J A and Sonenshein A L (J. Bacteriol 2008, 2505-2512) states that both bile salts and certain amino acids play an important role in bringing about germination of *C. diff.* spores. There has also been some research into compounds which act as inhibitors to the germination of *C. diff.* spores. Sorg J A and Sonenshein A L (J. Bacteriol 2010, 4983-4990) for instance, discloses various compounds found to reduce the rate of germination of *C. diff.* spores.

Accordingly, what is required is a method of treating *C. diff.* spores in vivo as well as methods for preventing the spread of *C. diff.* spores ex vivo, particularly in healthcare environments.

The invention is intended to overcome or at least ameliorate some of the problems outlined above.

SUMMARY OF THE INVENTION

There is provided in a first aspect of the invention, a compound according to general Formula 1 or a pharmaceutically acceptable salts thereof:

$$X-Z-M \qquad \text{Formula 1}$$

wherein; X is a bile salt, Z is a linker and M is an antimicrobial agent.

The inventors have found that by coupling a bile salt compound to an antimicrobial agent, it is possible to stimulate germination of *C. diff.* spores to form the active bacterial species which, being now more vulnerable to attack, are subsequently destroyed by the accompanying antimicrobial agent.

As bile salts are native to the body, produced by the liver and stored in the gallbladder, many of these compounds exhibit good biocompatibility and are relatively low in toxicity. The term "bile salt" as used herein is intended to refer to the compounds having a general structure or skeletal structure similar to that of the naturally occurring bile salts produced by the human body. This includes stereoisomers of naturally occurring bile salts and also includes naturally occurring bile salts comprising modified functional groups.

Typically, X is a compound according to formula 2:

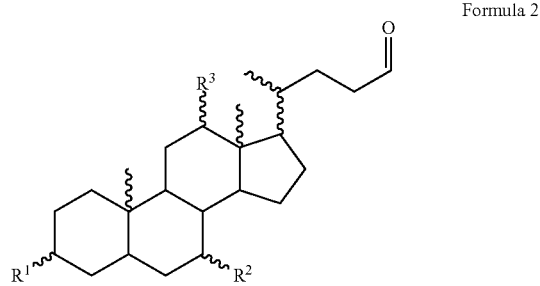

Formula 2 wherein, $R^1$ is selected from: hydroxy, alkoxy, acyloxy, aryloxy, acrylate or methacrylate; $R^2$ and $R^3$ are each independently selected from: hydrogen, hydroxy, alkoxy, acyloxy, aryloxy, acrylate or methacrylate groups.

Even more typically, X is a compound according to general formula 3:

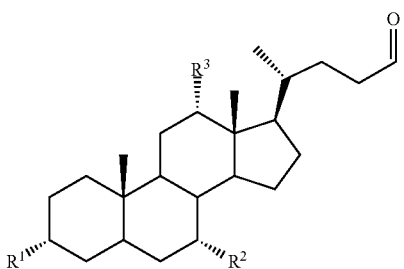

Formula 3 wherein $R^1$, $R^2$ and $R^3$ are as defined above and linker Z is attached to the carbon at the terminal C(O) moiety.

The inventors have found that bile salts having the stereochemistry shown in formula 3 are particularly effective at promoting germination of *C. diff.* spores. Without being bound by theory, it is believe that this orientation provides the most compatible structure with receptors, enzymes or structures present on the *C. diff.* spores which promotes germination.

For the avoidance of doubt, the invention is intended to encompass those compounds described herein as well as prodrugs and/or the biologically active species resulting from metabolisation of said compounds. The term "prodrug" is intended to refer to compounds which, on administration to the body, are converted into a compound as described herein.

It is often the case that $R^1$ is selected from: hydroxy, alkoxy and aryloxy groups and even more typically $R^1$ is a hydroxy or alkoxy group. Typically, $R^1$ is a hydroxy group.

In a typical embodiment, $R^2$ and $R^3$ are each independently selected from: hydrogen, hydroxy, alkoxy or aryloxy groups. $R^2$ and $R^3$ may each independently be selected from: hydrogen, hydroxy and alkoxy groups and it is typically the case that $R^2$ and $R^3$ are each independently selected from hydrogen and hydroxy groups.

The linker "Z" is typically a covalent linker. The term "covalent linker" is intended to mean a compound which is covalently bonded at a first position to the X group and which is also covalently bonded at a second position to the M group. Typically the first and second positions are located at points on the linker which are spaced apart from one another and it is often the case that the first and second positions are located at the two ends of the linker. Usually the linker is of a generally linear configuration having two ends, the two ends being the two extreme most ends of the linker.

In the situation where the first linkage Z is —NR—, R is typically selected from hydrogen, alkyl, aryl, acyl, alkenyl or alkynyl.

The linker Z may also be selected from: alkyl, aryl, acyl, alkenyl, alkynyl, ethers, polyether, esters, polyesters, amides, polyamides, amines or combinations thereof. More typically, the linker Z is selected from alkyl, alkenyl, ethers, polyethers or combinations thereof. Most typically the linker Z is polyethylene glycol and as such the compound of the invention may have a structure as shown in formula 4a:

formula 4a wherein n is an integer in the range of 1 and 10, and wherein X and M are as defined above. Typically, n is an integer in the range of 1 and 5 and most typically n is 1, 2 or 3.

Alternatively, the linker Z may comprise a first linkage A and a second linkage L. The order of the "A" and "L" linkages may be interchangeable i.e. the compound of the invention may be represented as "X-A-L-M" or "X-L-A-M". Typically however, it is the case that the compound of the invention is in the form "X-A-L-M".

In the situation where the first linkage A is —NR—, R is typically selected from hydrogen, alkyl, aryl, acyl, alkenyl or alkynyl. It is typically the case that A is —NR—.

The term 'aryl' is intended to refer to an aromatic ring structure. This may include one or more fused rings and the ring or rings may each independently be 5-, 6-, 7-, 8- or 9-membered rings. Typically, the aryl groups will be a single aromatic ring and even more typically, the ring may be a 5-, or 6-membered ring.

The term 'acyl' is intended to linear or cyclic carbon chains as well as branched carbon chains having at least one carbonyl group.

The term 'alkenyl' is intended to refer to linear or cyclic carbon chains as well as branched carbon chains having at least one unsaturated carbon-carbon double bond.

The term 'alkynyl' is intended to refer to linear or cyclic carbon chains as well as branched carbon chains having at least one unsaturated carbon-carbon triple bond.

The term 'alkyl' is intended to encompass aliphatic, linear and cyclic saturated carbon chains as well as branched saturated carbon chains.

The terms 'alkyl', 'aryl', 'alkenyl', 'acyl' and 'alkynyl' are intended to encompass groups which may be substituted with one or more heteroatoms and is also intended to encompass halogenated analogues thereof.

Typically each the 'alkyl', 'aryl', 'alkenyl', 'acyl' and 'alkynyl' are in the range of $C_1$ to $C_{10}$, more typically between $C_1$ to $C_8$ and even more typically $C_1$ to $C_5$ in length.

It is usually the case that R is selected from hydrogen or alkyl. Typically, R is a $C_1$-$C_{10}$ alkyl group which may be a linear alkyl group.

The second linker L is often selected from: alkyl, aryl, acyl, alkenyl, alkynyl, ethers, polyether, esters, polyesters, amides, polyamides, amines or combinations thereof. More typically, the linker L is selected from alkyl, alkenyl, ethers, polyethers or combinations thereof. Most typically, the linker L is polyethylene glycol and as such the compound of the invention may have a structure as shown in formula 4b or 4c:

Formula 4b

Formula 4c wherein n is an integer in the range of 1 and 10, and wherein X, A and M are as defined above. Typically, n is an integer in the range of 1 and 5 and most typically n is 1, 2 or 3.

M is typically an antibacterial agent. The antibacterial agent may be a broad-spectrum antibacterial agent or may be a specific antibacterial agent. Often, M may be an antibiotic. The antibiotics may be suitable for treating gram-negative bacteria and/or gram-positive bacteria.

In the invention, it is typically the case that M is a quaternary ammonium salt and M may be a compound according to general formula 5:

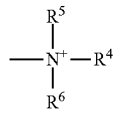

Formula 5 wherein each of $R^4$, $R^5$ and $R^6$ are independently selected from: alkyl, aryl, alkenyl, alkynyl, alkylamides or alkylamines. Each of $R^4$, $R^5$ and $R^6$ may be independently selected from: alkyl, aryl, acyl or alkenyl.

Usually, at least two of $R^4$, $R^5$ and $R^6$ are covalently bonded together and it is often the case that two of $R^4$, $R^5$ and $R^6$ are covalently bonded together. The counter ion accompanying the quaternary ammonium salt is not particularly limited to a specific group. Typically, the counter ion will be an inorganic anion and it is usually the case that the counter ion is a chloride ion.

The inventors have found that quaternary ammonium salts function well as antibacterial agents. Without being bound by theory, it is believed that unlike certain antimicrobial agents such as silver ions, the quaternary ammonium salts are not used up in the process of destroying the target pathogen. It is though that the quaternary ammonium salt catalyses the destruction of pathogens and is not used up, or at least is used up at a much slower rate than other antimicrobial agents, in the process.

In a further embodiment of the invention, there is provided a compound according to any one of the following formulae 6a-6n:

Formula 6a
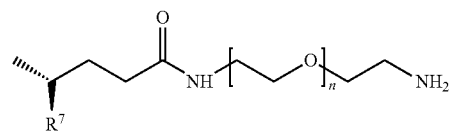

Formula 6b
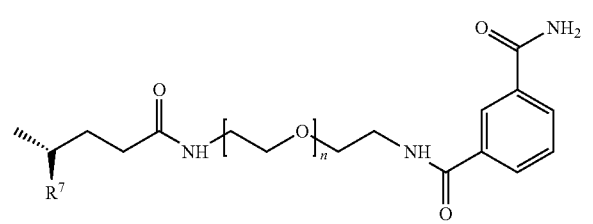

Formula 6c
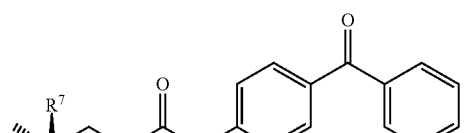

Formula 6d
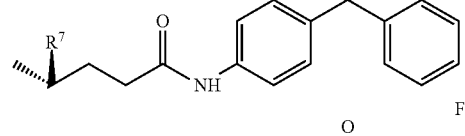

Formula 6e
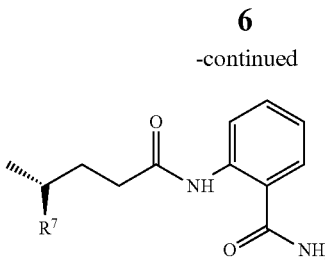

Formula 6f
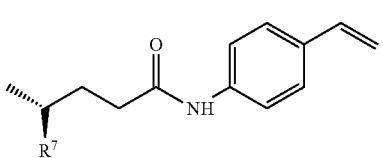

Formula 6g
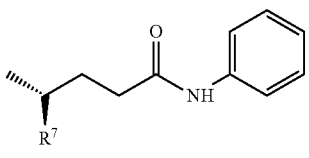

Formula 6h
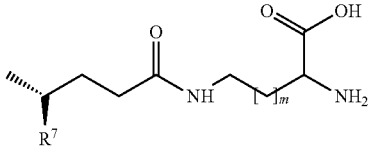

Formula 6i
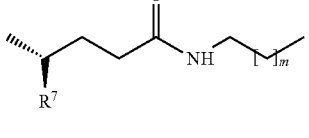

Formula 6j
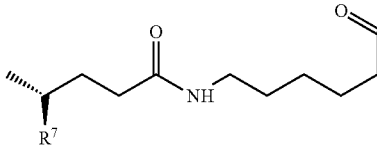

Formula 6k
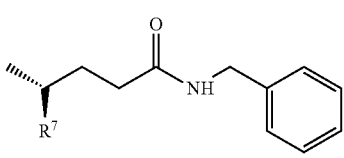

Formula 6l
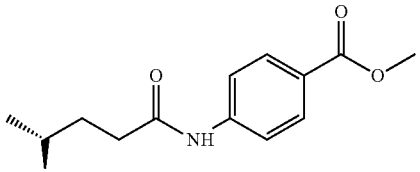

Formula 6m
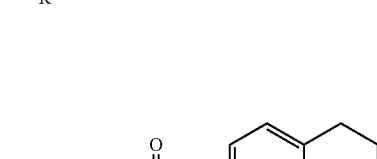

Formula 6n

[Structure: a chiral carbon with R⁷ substituent connected via -CH(CH₃)(CH₂)₂C(O)NH- to a para-substituted phenyl, which bears a -CH(OH)-phenyl group]

wherein n and m are each independently an integer between 1 and 10, and $R^7$ is a bile salt as described above. The skilled person would understand that formulae 6a-n are intended to cover compounds wherein the bile salt group $R^7$ refers to the bile salt minus the —CCH₃(CH₂)₂CONH—.

In a second aspect of the invention, there is provided a composition comprising a compound according to the first aspect of the invention further comprising one or more additives.

Typically the additives are selected from: amino acids, conjugated amino acid, bile salts and/or antimicrobial agents.

The amino acids suitable for inclusion in the composition of the invention may be any of the naturally occurring amino acids and it is typically the case that the amino acids and conjugated amino acids are selected from: glycine, glutamine, leucine, isoleucine, alanine and taurine. It may be the case that the conjugated amino acid is taurine.

Often, the antimicrobial agents used as additives with the composition of the invention are antibiotics. These antibiotics may be broad-spectrum antibiotics or bacteria specific antibiotics. Usually, the antibiotics will be effective at treating *C. diff.* bacteria. The antibiotics may be suitable for treating gram-negative and/or gram-positive bacteria.

In the composition of the invention, it is typically the case that the antimicrobial agent additive is a quaternary ammonium salt according to general Formula 7:

Formula 7

$$R'-\overset{R^5}{\underset{R^6}{N^+}}-R^4$$

wherein each of R', $R^4$, $R^5$ and $R^6$ are independently selected from: alkyl, aryl, alkenyl, alkynyl. Each of R', $R^4$, $R^5$ and $R^6$ may be independently selected from: alkyl, aryl, alkenyl.

Usually, at least two of R', $R^4$, $R^5$ and $R^6$ are covalently bonded together and it is often the case that two of R', $R^4$, $R^5$ and $R^6$ are covalently bonded together. The counter ion accompanying the quaternary ammonium salt is not particularly limited to a specific group. Typically, the counter ion will be an inorganic anion and it is usually the case that the counter ion is a chloride ion.

In an alternative embodiment of the invention, there is provided a composition comprising either a bile salt and an antimicrobial agent; or a compound, polymer or copolymer according to the above aspects of the invention or combinations thereof. Where the composition comprises a compound, polymer or copolymer or combinations thereof according to the above aspects of the invention, the composition may additionally comprise a bile salt and/or an antimicrobial agent.

As mentioned above, the combination of bile salts and an antimicrobial agent provides both *C. diff.* spore germinating properties as well as antimicrobial properties that can destroy subsequently germinated *C. diff.* bacteria. Therefore, by including one or more bile salts, as defined above, in a composition containing an antimicrobial agent, environments containing *C. diff.* spores can be made safe by exposing said environments to the composition thereby forcing germination of the *C. diff.* spores which, in the presence of an antimicrobial agent, are subsequently destroyed. This is particularly advantageous ex vivo in healthcare environments.

Typically, the composition is a cleaning agent for cleaning surfaces and environments containing *C. diff.* spores. It is more difficult to treat *C. diff.* spores present within an infected patient as many antimicrobial agents suitable for use ex vivo are not suitable for in vivo use and also because the bile salts and antimicrobial agents can not act in tandem with one another due to the difficulties in getting both compounds into the gut together at the same time. This problem can be solved by using the compound according to the first aspect of the invention which covalently links the bile salt and the antimicrobial compounds together.

The cleaning agent may additionally comprise a compound, polymer, copolymer or combinations thereof according to the above aspects of the invention as well as other more conventional additives. For example, the cleaning agent may further comprise one or more solvents. Typically these will be hydrophobic or hydrophilic solvents. The cleaning composition may also comprise one or more surfactants and/or other compounds found in conventional cleaning products as would be well familiar to the skilled person.

Alternatively, the composition may be a coating composition adapted to provide a *C. diff.* spore resistant layer on surfaces to which it is applied. Accordingly, the composition typically comprises a solvent for solubilising the one or more bile salts and the at least one antimicrobial agents. The bile salt and antimicrobial agent are typically as defined above. However, the composition may also comprise polymerisable moieties or polymers which cause the coating composition to set once it has been applied to a surface. Other optional additives include leachable antimicrobial agents such as a silver ion source which secrete antimicrobial agents over time. Other additives, such as colorants to improve the aesthetic of the coatings and dispersants and plasticisers to improve the "spray-ability" or improve the ease of application of the coating composition to a surface may also be included in the composition as would be appreciated by a person skilled in the art.

In a third aspect of the invention, there is provided a polymer obtainable by the polymerisation of a composition comprising one or more compounds of general Formula 1, wherein the compounds comprise at least one polymerisable moiety. Preferred aspects of Formula 1 may be as defined above.

By polymerising one or more compounds according to Formula 1, it is possible to fabricate a polymer having many repeating units, each comprising a bile salt moiety capable of stimulating germination of a *C. diff.* spore and an antimicrobial moiety capable of destroying the *C. diff.* bacterium as soon as it has germinated. This polymer can also be manufactured into films and coating materials that can be incorporated into or on surfaces to provide a *C. diff.* spore killing property.

The position of the polymerisable moiety is not particularly restricted, provided that it does not interfere with the ability of the compound of the invention to at least partially promote germination of *C. diff.* spores and not prevent an antimicrobial activity. The polymerisable moiety may form part of the X group on at least one of the compounds of general Formula 1. Alternatively, the polymerisable moiety may be present on the L group and/or M group on at least one of the compounds of general Formula 1. It is typically the case that the L group comprises the polymerisable moiety.

As regards the structure of the polymerisable moiety, the skilled person will appreciate that any moiety which can be polymerised without compromising the spore germination and antimicrobial activity of the compound of the invention can be used. Typically, wherein the polymerisable group is unsaturated. Unsaturated functionalities, such as carbon-carbon double bonds and triple bonds, provide a good "handle" for linking together monomers using a number of known polymerisation techniques with which the skilled person will be familiar.

Often the polymerisable group comprises an alkenyl group and it is typically the case that the polymerisable group comprises a terminal vinyl group.

The polymerisation used in the invention is typically a free radical polymerisation. The polymerisation technique is not particularly limited but may be any reasonable polymerisation method including for example living polymerisations and living radical polymerisations. Examples of some polymerisation techniques which may be used include polymerisations selected from: atom transfer radical polymerisation, reversible addition-fragmentation chain transfer polymerization, stable free radical polymerization, living ionic polymerisation, living ring-opening metathesis polymerization, group transfer polymerization, living Ziegler-Natta polymerization or combinations thereof.

Often the polymerisation is selected from: atom transfer radical polymerisation or reversible addition-fragmentation chain transfer polymerisation and it is most typically the case that the polymerisation is atom transfer radical polymerisation.

In another embodiment of the invention, there is provided a polymer wherein the composition comprises two or more compounds of general Formula 1. The polymer need not be restricted to comprising one particular type of monomer according to general Formula 1 but may in fact be a copolymer. Accordingly, a range of monomers according to general Formula 1 can be polymerised into the polymer which may, for example, each comprise a different antimicrobial agent, bile salt and/or linker.

Additionally, the composition (from which the polymer is obtained) may further comprise one or more monomers other than the compounds of general Formula 1. The polymer need not solely consist of monomers according to general Formula 1 but may include other, typically more simple monomers, in order to change the physical properties of the polymer. For example, where a rigid antibacterial polymer is required, styrene could be incorporated into the polymer in order to modify physical properties of the polymer. Other modifications would be apparent to the skilled person in order to vary a range of properties of the polymer, such as melting point, acid/base resistance and hydrophilicity to name but a few. Further, cross linking agents may be introduced i.e. monomers comprising moieties which can be made to react with other cross linking agents or complimentary groups in other polymer chains in order to form cross linked networks of polymers. The functionality of the monomers not according to general Formula 1 may also be varied to provide particular chemical properties to the polymer. The monomer units may be selected from: amino acids, conjugated amino acids, bile salts, antimicrobial agents or combinations thereof as defined above.

As mentioned above the polymer may be a copolymer which may be a block copolymer, alternating copolymer or statistical copolymer or a combination thereof.

In a fourth aspect of the invention, there is provided a copolymer obtainable by the polymerisation of one or more first monomers comprising a polymerisable group and an antimicrobial group; and one or more second monomers comprising a polymerisable group and a bile salt group.

Typically the bile salt group and the antimicrobial groups have structures as outlined above. The polymerisable groups present in the first and second monomers are not particularly limited nor are these groups required to be identical in both the first and second monomers. These groups need only be capable of undergoing polymerisation with one another to form a copolymer without removing either the *C. diff.* spore germinating properties of the bile salt groups or the antimicrobial properties of the antimicrobial groups.

The copolymer according to the fourth aspect of the invention also need not solely consist of copolymers obtainable by the polymerisation of one or more first monomers comprising a polymerisable group and an antimicrobial group; and one or more second monomers comprising a polymerisable group and a bile salt group. Additional monomers may be included, other than those having antimicrobial or bile salt functional groups. Such monomers can be included into the copolymer in order to change the physical properties of the polymer in much the same way as outlined above as would be clear to a person skilled in the art.

The chemical structure of the copolymer may also be varied by introducing monomers having specific chemical functionality. For instance, the additional monomers may be selected from one of the naturally occurring amino acids. Typically, the amino acids and/or conjugated amino acids may be selected from glycine, glutamine, leucine, isoleucine, alanine and taurine. It is typically the case that the additional monomer is taurine.

Typically, the polymerisable group is unsaturated. Unsaturated functionalities, such as carbon-carbon double bonds and triple bonds, provide a good "handle" on the first, second and additional monomers which can be linked together using a number of known polymerisation techniques with which the skilled person will be familiar. Often the polymerisable group comprises an alkenyl group and it is typically the case that the polymerisable group comprises a terminal vinyl group.

It is also typically the case that the copolymer is a substantially alternating polymer. This ensures that the bile salt groups and the antimicrobial groups are in close proximity to one another along the polymer chain in order to ensure that once germination is provoked by the bile salt group, the antimicrobial group will be available to destroy the germinated *C. diff.* bacterium.

In an alternative embodiment, the copolymer of the fourth aspect of the invention may be fabricated as a graft copolymer. A precursor polymer may be synthesised from one or more monomers comprising reactive connecting groups. The term "connecting group" is intended to refer to a reactive moiety which can function as a point along the length of the precursor polymer at which further functionality can be introduced. Typically, the connecting groups are suitable for undergoing click chemistry, a technique known in the art, and the connecting group may be selected from either an alkyne or azide group. Alternatively, one or more of the bile salt, antimicrobial agent and/or compound of formula 1 (comprising both a bile salt group and an antimicrobial group) may be functionalised with an alkene group which permits said compounds to be grafted onto a precursor polymer such as polyolefins. Examples of preferred polyolefins include polyethylene and in particular high density polyethylene (HDPE).

The precursor polymer may be reacted with antimicrobial agents and bile salt compounds which have been functionalised with suitable groups (corresponding to the connecting groups present in the precursor polymer) in order to form the copolymer according to the fourth aspect of the invention. The precursor polymer is typically obtainable by the polymerisation of a first monomer comprising a first connecting group and a second monomer comprising a second connecting group. By employing different connecting groups, it is possible to more easily control the addition of antimicrobial agents and bile salts on to the precursor polymer backbone.

The polymerisation process used in the fourth aspect of the invention is not particularly restricted, provided that the germinating properties of the bile salt group and antimicrobial properties of the antimicrobial group are not lost in the process, for example by degradation of said groups as a result of harsh reaction conditions or high temperatures. The polymerisation processes used is typically as defined above.

The antimicrobial groups and bile salt groups are typically as defined above.

There is provided in a fifth aspect of the invention, a polymeric material which comprises either a bile salt and an antimicrobial agent; or a compound, polymer or copolymer according to the above aspects of the invention or combinations thereof. Where the polymeric material comprises a compound, polymer or copolymer or combinations thereof according to the above aspects of the invention, the polymeric material may additionally comprise a bile salt and/or an antimicrobial agent.

The polymeric material may be a conventional plastics material into which a bile salt and one or more antimicrobial agents (and/or compound, polymer, copolymer or combinations thereof according to the above aspects of the invention) are incorporated i.e. as a mixture.

By incorporating a bile salt and an antimicrobial agent into conventional plastics, it is possible to imbue conventional plastics materials with properties that cause *C. diff.* spores to germinate on contact with the plastics material and then subsequently destroys the germinated *C. diff.* spores.

Accordingly, in a first embodiment, the plastics material may be selected from any conventional plastics and it is typically the case that the plastics are selected from: low density polyethylene (LDPE), high density polyethylene (HDPE), polypropylene (PP), polyvinyl chloride (PVC), polystyrene (PS), nylon, teflon (polytetrafluoroethylene) and thermoplastic polyurethanes (TPU).

The bile salts, antimicrobial agents, compounds, polymers and copolymers of the invention may be admixed into the polymers when they are in a molten state in order to homogeneously disperse these components throughout the plastics material. Alternatively, said materials could be worked into the surface of the plastics material to form a coating on the surface of the formed plastics material.

In addition, further additives may be combined with the plastics material to modify the plastics material's properties. For example, a wide range of antibacterial, antiviral and antifungal agents may be incorporated into the plastics material and so too may other additives for modifying the flexibility, strength, temperature resistance and other physical properties of the plastic. Various additives, such as colorants and plasticisers may be included in the plastics material as would be familiar to persons skilled in the art.

In another embodiment, the plastics material is a polymer or copolymer according to the above aspects of the invention. In this embodiment, the polymer itself rather than the additives incorporated therein, provides both the *C. diff.* spore germinating properties and the antimicrobial properties although these may be supplemented by incorporating bile salts and/or antimicrobial agents and/or compounds of the invention into the plastics material. Further optional additives may be included as described above.

In a sixth aspect of the invention, there is provided an electronic device comprising a casing, wherein the casing comprises a compound or composition as described above. Typically, the casing is manufactured from a polymeric material and/or has been coated with a coating composition as described above.

Electronic devices, such a phones, watches, computers, tablets, and Personal Digital Assistant are widespread among most populations and are in regular contact with human hands. As such, bacteria and other microorganisms are transferred to and from electronic devices on a regular basis. Such devices can be difficult to clean as many cleaning agents are water based and water can of course interfere with the electric function of said devices.

Accordingly it is desirable to introduce antimicrobial agents into and on the surfaces of electronics devices to minimise spread of microbes. The term "casing" as used herein is intended to encompass the outer surface of an electronic device which typically contacts human skin in normal use. This includes screens, which may be glass or transparent plastics materials, as well as the housing (which contains the working electronics) as well as buttons which may be integral to the device and/or protrude from the device. Typically, the electronic devices are mobile phones or portable computer devices.

In a seventh aspect of the invention, there is provided a sheath or detachable casing for an electronic device, wherein the sheath or detachable sheath or detachable casing comprises a compound or composition as described above. Typically, the casing is manufactured from a polymeric material and/or has been coated with a coating composition as described above.

It is often the case that electronic devices are themselves housed within protective sheaths or detachable casings. This is usually to protect the electronic devices from impacts in the event that the device is dropped or to provide an alternative aesthetic to the device. However, such sheaths or detachable casings then become a component on which microbes can be transferred. As such, it is desirable to incorporate the compounds, composition, polymers, copolymer and/or combinations thereof as described above into these sheaths or detachable casings in order to minimise the spread of microbes.

In an eighth aspect of the invention, there is provided a compound according to the first aspect of the invention for use in the treatment and/or prevention a disease selected from: *C. difficile* associated disease (CDAD), and toxic megacolon.

In an ninth aspect of the invention, there is provided a method of treating or preventing a disease selected from *C. difficile* associated disease (CDAD), and toxic megacolon comprising administering a compound according to the first aspect of the invention to a patient.

The invention also provides a compound as defined in the materials and methods below, and its use in a method according to the invention.

The invention will be described with reference to the accompanying figures and examples.

EXAMPLES

*Clostridium difficile* Spore Germination Potential of Compound 129

Figure 1:
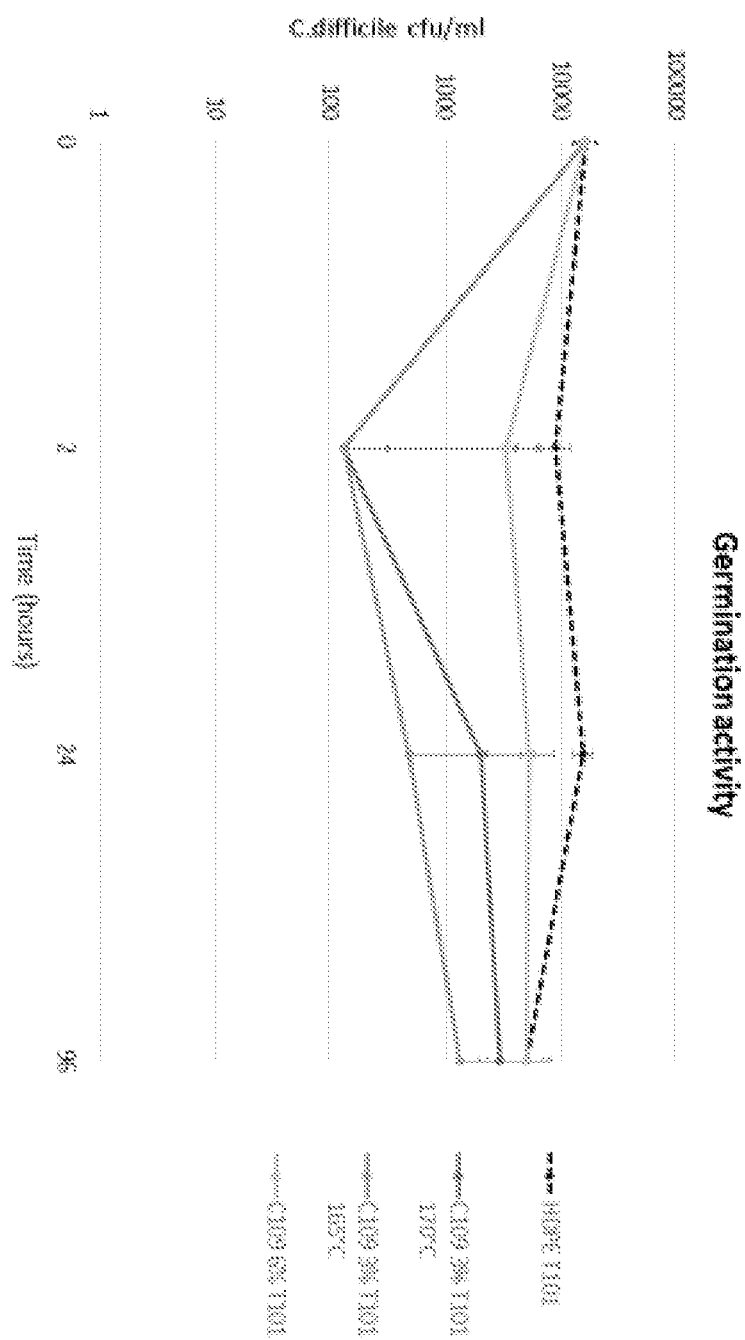
FIG. 1 shows germination activity of HDPE (high density polyethylene)/"T101" (radical initiator 2,5-dimethyl-2,5-bis-(tert-butyl peroxy)hexane) polymer films prepared with and without (control) C109 (compound 129) at 3% (at 165° and 170° C.) and at 6% (at 160° C.).

HDPE (high density polyethylene) samples containing the modified bile salt compound 129, reactively processed under different compression moulding conditions, were tested to determine the germination activity. Polymer film samples containing 3% of compound 129 prepared (at molar ratio of 0.005 of peroxide to bile salt) both at 165° C. and 170° C. demonstrated an equal level of germination activity at 2 hours, resulting in a 2.2 Log reduction compared to the HDPE/peroxide T101 control (FIG. 1). However, after 24 and 46 hours, samples processed at the lower temperature demonstrated a slightly higher level of germination activity suggesting that higher temperatures, used under these conditions, give rise to a reduction in the germination activity of the modified bile salt compound 129. Samples prepared similarly but with a higher amount of compound 129 (6%) did not perform well. Table 1 shows that, following subsequent exposure to ethanol, compound 129 prepared at 165° C./170° C. yields a 99.2% reduction in *C. difficile* spores. This confirms the germination activity of compound 129 when incorporated into HDPE by reactive processing.

TABLE 1

Germination activity of compound 129 reactively processed with HDPE after subsequent exposure to ethanol

| | Log Reduction | | | % Reduction | | |
|---|---|---|---|---|---|---|
| Polymer | 2 hours | 24 hours | 96 hours | 2 hours | 24 hours | 96 hours |
| compound 129 3% T101 170° C. | 2.165 | 0.971 | 0.802 | 99.2 | 87.8 | 82.0 |
| compound 129 3% T101 165° C. | 2.165 | 1.598 | 1.154 | 99.2 | 97.1 | 92.0 |
| compound 129 3% T101 160° C. | 0.752 | 0.546 | 0.577 | 79.8 | 67.6 | 69.8 |

Dual Activity of Compound 129 (Germination of *C. difficile* Spore and Subsequent Elimination)

Figure 2:
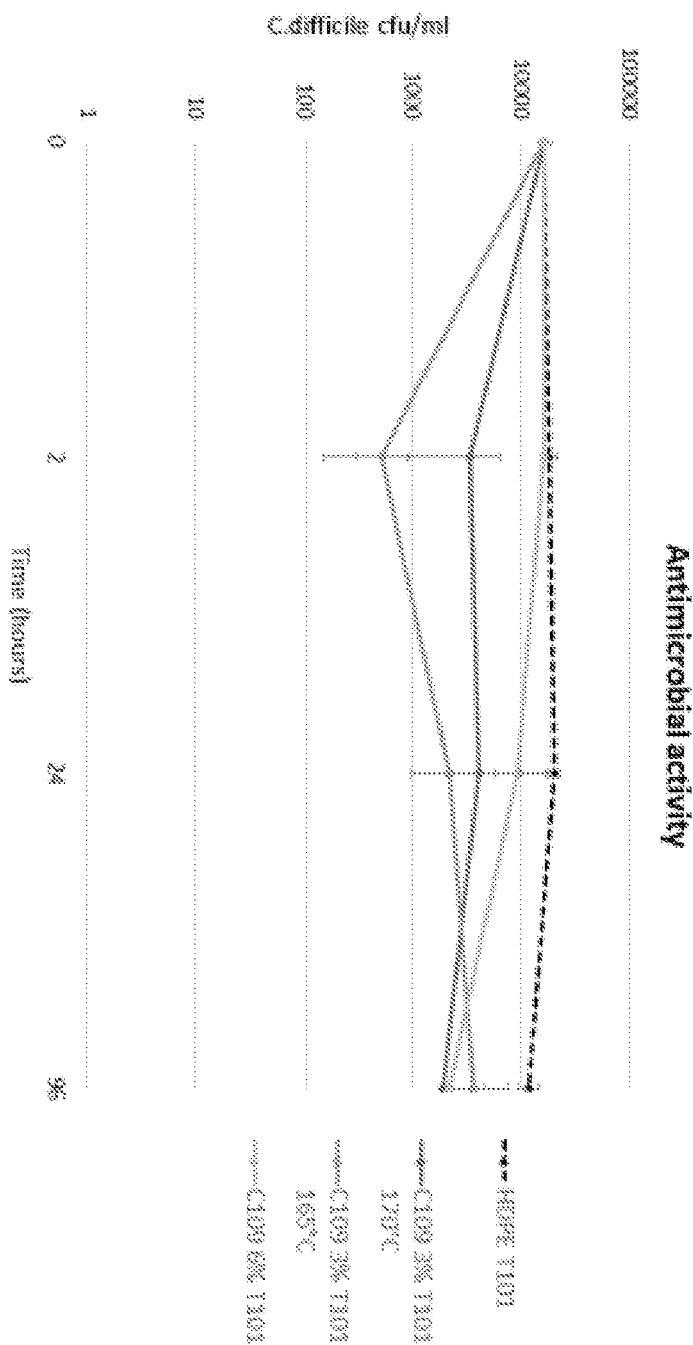
FIG. 2 shows germination and antimicrobial efficacy of C109 (compound 129) reactively processed in HDPE (high density polyethylene).

Reactively processed HDPE polymer containing compound 129 is shown to have the ability to both germinate the spores of *C. difficile* and reduce the subsequent metabolically active bio-load by 96.9%, see FIG. 2 and Table 2. This exemplifies, therefore, the dual action of compound 129 and its efficacy both as a germinant and an antimicrobial. Reactive processing the polymer at 170° C. changes markedly the dual activity of compound 129 giving a spore reduction of 79.6%.

TABLE 2

Germination and antimicrobial efficiency of compound 129 in HDPE

| | Log Reduction | | | % Reduction | | |
|---|---|---|---|---|---|---|
| Polymer | 2 hours | 24 hours | 96 hours | 2 hours | 24 hours | 96 hours |
| compound 129 3% T101 170° C. | 0.747 | 0.666 | 0.998 | 79.6 | 75.4 | 88.5 |
| compound 129 3% T101 165° C. | 1.563 | 0.940 | 0.714 | 96.9 | 86.9 | 78.0 |
| compound 129 6% T101 160° C. | 0.057 | 0.315 | 0.936 | 0.0 | 44.8 | 86.8 |

Materials and Methods

Proton NMR spectra were obtained on a Bruker AC 250 instrument operating at 250 MHz as solutions in $CDCl_3$ and referenced from $\delta CDCl_3 = 7.26$ ppm unless otherwise stated. Carbon NMR spectra were obtained on a Bruker AC 250 instrument operating at 63 MHz as solutions in $CDCl_3$ and referenced from $\delta CDCl_3 = 7.26$ ppm unless otherwise stated. Infrared spectra were recorded as KBr discs on a Mattson 3000 FTIR spectrophotometer. Electrospray mass spectrometry was carried out on a Waters LCT Premier ToF (Time of flight) mass spectrometer. Electrospray mass spectrometry and accurate mass spectrometry was also carried out by the EPSRC National Mass Spectrometry Facility in Swansea with a MAT95 magnetic sector. Melting points were obtained using a Reichert-Jung Thermo Galan hot stage microscope and are corrected. All chemicals were purchased from Sigma Aldrich.

Synthesis of methyl cholate (1)

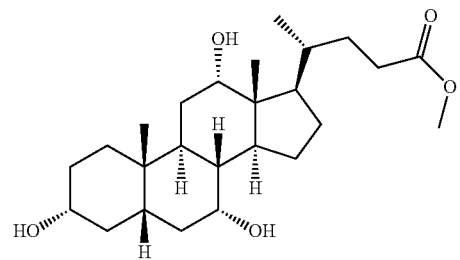

Cholic acid (5.0 g, 12.2 mmol) was added to dry methanol (20 mL). Acetylchloride (0.5 mL, 0.04 mmol) was added under argon. The solution was heated at reflux for 45 minutes, then left to cool. Once at room temperature, the solution was cooled further on ice whereupon crystals appeared. The solid material was collected by filtration and washed with small amounts of methanol to give methyl cholate as a white solid. It was dried at room temperature under vacuum.

Yield=3.548 g (68.9%)

Melting point=110.8-111.9° C.

$^1$H NMR ($CDCl_3$) δ ppm: 0.67 (s, 3H, Me-18), 0.88 (s, 3H, Me-19), 0.99 (d, 3H, Me-21), 1.0-2.43 (m steroid structure) 2.49 (s, 1H, H—C—C═O), 3.47 (s, 1H, H—C—OH), 3.66 (s, 1H, CH-3), 3.84 (d, 1H, CH-7), 3.95 (s, 1H, CH-12) ppm $^{13}$C NMR ($CDCl_3$) δ 174.77 (C═O), 73.26 (C12), 68.66 (C7), 52.67 (C3), 51.50 ($CH_3$), 50.33, (47.05, 46.44, 41.82, 39.47, 39.01, 35.24, 34.70, 31.06, 29.86, 28.17, 27.45, 26.60, 23.17 steroid structure) 22.44 (C19), 17.31 (C21), 12.49 (C18).

MS (+APCI) m/z=482 (M+)
IR ν=3399 (OH), 2921, 2869, 1739 (C=O), 1449 cm$^{-1}$

Synthesis of cholic acid benzyl amide (2)

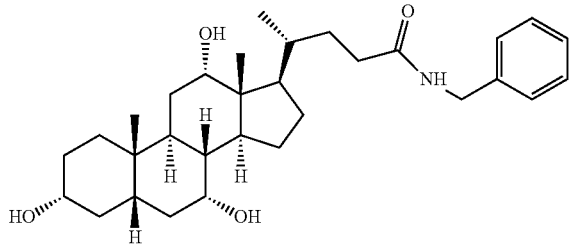

Methyl cholate (1 g, 2.3 mmol) was placed into a stainless steel pressure vessel along with benzyl amine (1.3 mL, 12.2 mmol) and toluene (5 mL). The pressure vessel was placed into an oil bath and heated to 150° C. for 48 hours. The pressure vessel was left to cool before dismantling it. The solution was poured into a round bottomed flask and placed on ice. The solid product was then collected by filtration and dried at room temperature under vacuum. The material was recrystallised from ethanol/water to give a white, powdery solid which was dried at room temperature under vacuum under vacuum.

Yield=0.378 g (37.8%)
Melting point=114.1-114.7° C.
$^1$H NMR (Methanol-d$_4$) δ ppm: 0.69 (s, 3H, Me-18), 0.91 (s, 3H, Me-19), 1.02 (d, J=6.2 Hz, 3H, Me-21), 1.0-2.439 (m, steroid structure) 3.36 (m, 1H, CH-3), 3.78 (s, 1H, H—C-7), 3.94 (s, 1H, CH-12), 4.35 (d, 2H, J=1.9 Hz PH—CH$_2$), 7.29 (m, J=6.2 Hz, 6H, aromatic ring)
$^{13}$C NMR (CDCl$_3$) δ 219.45, 218.76, 173.58 (C=O), 154.31 (aromatic ring), 128.69 (aromatic ring), 127.85 (aromatic ring), 127.48 (aromatic ring), 125.07 (aromatic ring), 76.51 (C12), (43.61, 41.92, 39.51, 35.26, 34.69 steroid structure), 26.58 (C19), 17.44 (C21), 12.54 (C18)
MS (+APCI) m/z=Found 498.3578; calculated for C$_{31}$H$_{48}$N$_1$O$_4$ 497.71; -1.4 ppm
IR ν=3411, 2917, 1644 (C=O), 1540, 1457 cm$^{-1}$ Synthesis of N-(4-aminobutyl) cholanamide (3)

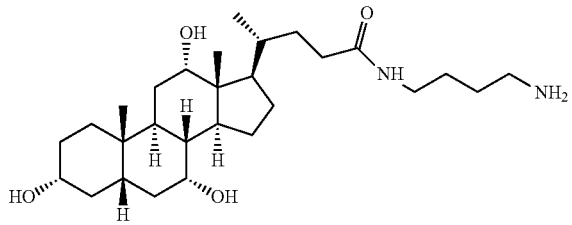

Methyl cholate (1 g, 2.3 mmol) along with 1,4-diaminobutane (1,4-DAB) (10 mL) was put into a stainless steel pressure vessel and tightly secured. It was placed into an oil bath and heated to 150° C. for 48 hours. The pressure vessel was left to cool to room temperature before dismantling it. 30 mL chloroform was added to dissolve the product and excess 1,4-DAB which was then poured into a round bottomed flask. The chloroform was taken off using a rotary evaporator and the 1,4-DAB was taken off under reduced pressure rotary evaporation. Dichloromethane (90 mL) was added to precipitate the product. The yellow solid was collected by filtration and dried at room temperature under vacuum.

Yield: 0.3 g, (30.14%)
Melting point: 116.4-124.5° C.
$^1$H NMR (CDCl$_3$) δ ppm: 0.68 (s, 3H, Me-18) 0.89 (s, 3H, Me-19) 1.00 (d, J=6.3 Hz, 3H, Me-21) 1.0-2.43 (m, steroid structure) 1.22 (dd, J-14.1, 8.5 Hz, CH) 2.71 (s, CH$_2$) 3.28 (m, 1H, CH-3) 3.86 (s, 1H, CH-7) 3.98 (s, 1H, CH-12)
$^{13}$C NMR (DMSO) δ 172.43 (C=O), 107.85, 70.97 (C12), 66.20 (C7), (46.08, 45.70, 41.35, 40.17, 39.84, 37.97, 35.65, 35.13, 34.87, 34.36, 28.55, 27.51, 27.25, 26.42, 26.20, 22.81, 22.60 steroid ring), 41.71 (CH$_2$), 40.51 (CH$_2$), 30.38 (CH$_2$), 20.75 (C19), 19.52 (C21), 17.10, 12.31 (C18).
MS (+APCI) m/z=Found 479.3849; calculated for C$_{28}$H$_{50}$N$_2$O$_4$ 478.3771; -1.0 ppm
IR (KBr) ν=3274, 2935, 2898, 2865, 2831, 1736, 1669 (C=O), 1548 cm$^{-1}$ Synthesis of N-[2-(2-aminomethylamino)ethyl] cholanamide (4)

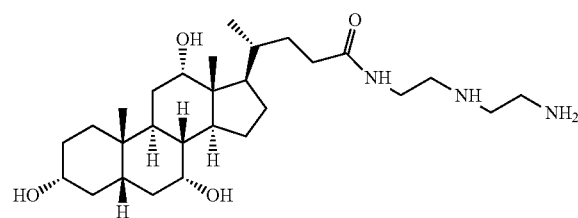

Methyl cholate (0.5 g, 1.15 mmol) along with diethylenetriamine (2 mL) was put into a round bottomed flask under argon. It was placed into an oil bath and heated to 95° C. for 48 hours. The flask was left to cool to room temperature. Aceonitrile (15 mL) was added to precipitate the product which was then collected by filtration. Solvent extraction between water and chloroform to carried out to purify the product. The chloroform was evaporated under reduced pressure. The solid was dried at room temperature under vacuum at room temperature under vacuum.

Yield=0.07 g (14%)
Melting point: 205.6-206.8° C.
$^1$H NMR (CDCl$_3$) δ ppm: 0.66 (s, 3H, Me-18) 0.87 (s, 3H, Me-19) 0.9 (d, J=6.0 Hz, 3H, Me-21) 1.0-2.44 (m, steroid structure) 2.69 (d, J=5.9 Hz, CH$_2$) 2.75-2.88 (m) 3.35 (s) 3.47 (m, 1H, CH-3) 3.57 3.69 3.72 3.83 (s, 1H, CH-7) 3.94 (s, 1H, CH-12) 7.01 (s, 1H, NH)
$^{13}$C NMR (DMSO) δ ppm: 172.59 (C=O), 70.98 (C12), 70.41 (C3), 66.22 (C7), (45.70, 41.50, 41.32, 40.49, 40.16, 35.28, 34.35, 32.44, 31.57, 30.38, 28.53, 27.28, 26.18 steroid ring), 22.58 (C19), 17.08 (C21), 12.32 (C18).
MS (+APCI) m/z=Found 494.3958; calculated for C$_{29}$H$_{53}$N$_3$O$_4$ 493.3880; 0.6 ppm
IR (KBr) ν=3253, 2929, 2865, 1751, 1648 (C=O), 1557 cm$^{-1}$

Synthesis of N-[3-(cyclohexylamino)propyl] cholanamide (5)

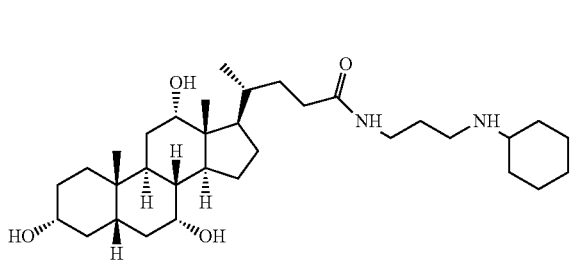

Methyl cholate (2 g, 4.6 mmol) along with cyclohexyl-1,3-propanediamine (4.08 mL) was added to a round bottomed flask under nitrogen. The flask placed in a oil bath at 95° C. for 48 hours before raising the temperature to 120° C. for 12 hours. The flask was allowed to cool before chloroform (30 mL) was added to dissolve the product. Solvent extraction between chloroform (30 mL) and water (30 mL) removed any excess amine. This was repeated three times. The chloroform layer was dried over magnesium sulphate and evaporated under reduced pressure to give a solid that was recrystallized from chloroform-petrol 60-80.

Yield=1.2 g (60%)

Melting point: 104.5-105.8° C.

$^1$H NMR (CDCl$_3$) δ ppm: 0.67 (s, 2H, Me-18) 0.89 (s, 2H, Me-19) 0.98 (d, 3H, Me-21) 1.0-2.43 (m, steroid structure) 2.61-2.79 (m, ring) 3.26 (m, 1H, CH-3) 3.43 (m, 1H, NH) 3.84 (s, 1H, CH-7) 3.97 (s, 1H, CH-12)

$^{13}$C NMR (CDCl$_3$) δ ppm: 173.94 (C=O), 71.85 (C12), 68.27 (C7), 56.87 (CH), (46.51, 41.49, 40.08, 39.58, 38.83, 35.38, 31.74, 31.62, 30.41, 29.08, 28.17, 27.61, 26.43 (CH), 26.10 steroid ring), 45.30 (CH$_2$), 40.68 (CH$_2$), 25.11 (CH), 34.80 (CH), 33.12 (CH), 23.31, 22.69, 22.51 (C19), 17.57 (C21), 14.17, 12.50 (C18), 11.48.

MS (+APCI) m/z=Found 547.4475; calculated for C$_{33}$H$_{58}$N$_2$O$_4$ 546.4397; 0.4 ppm IR (KBr) ν=3265, 3068, 2919, 2853, 1648 (C=O), 1554 cm$^{-1}$ Coupling of Cholic Acid with Ethylchloroformate and Various Amines General procedure for the coupling of cholic acid to primary and secondary amines Cholic acid (0.5 g, 1.2 mmol) was dissolved in THF (30 mL) along with triethylamine (2.9 mL, 0.3 mmol). The solution was put on ice for 10 minutes before ethylchloroformate (0.13 mL, 0.013 mmol) was dripped in over 10 minutes. The solution was allowed to react for two hours at room temperature. The required amine (1.2 mmol) was added and left to react for 3 hours. The reaction was quenched with water (30 mL). The mixture was washed with water (3×30 mL). The organic layer was dried over magnesium sulphate and the solvent was evaporated under reduced pressure. Solvent extraction between water and ethyl acetate was preformed 3 times before the organic layer was removed on the rotary evaporator. The product was dried at room temperature under vacuum.

Synthesis of N-[3-(cyclohexylamino)propyl] cholanamide (6)

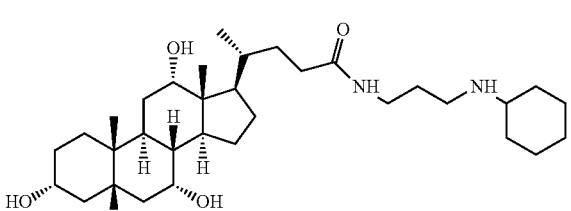

The procedure was followed as the above with the exception of the removal of the two hour wait before adding the amine. Cyclohexylpropanediamine (0.24 mL, 1.56 mmol) added in one portion. The crude material was purified by flash chromatography eluting with methanol.

Yield=0.36 g (72%)

Melting point: 104.5-105.9° C.

$^1$H NMR (CDCl$_3$) δ ppm: 0.67 (s, 2H, Me-18) 0.89 (s, 2H, Me-19) 0.98 (d, 3H, Me-21) 1.0-2.439 (m, steroid structure) 2.61-2.79 (m, ring) 3.26 (m, 1H, CH-3) 3.43 (m, 1H, NH) 3.84 (s, 1H, CH-7) 3.97 (s, 1H, CH-12)

$^{13}$C NMR (CDCl$_3$) δ ppm: 173.94 (C=O), 73.08 (12), 71.85 (C3), 68.27 (C7), 56.87 (CH), (46.51, 41.49, 40.08, 39.58, 38.83, 35.38, 31.74, 31.62, 30.41, 29.08, 28.17, 27.61, 26.10 steroid ring), 45.30 (CH$_2$), 40.68 (CH$_2$), 34.80 (CH$_2$), 33.12 (CH$_2$), 26.43 (CH), 25.11 (CH), 23.31, 22.69, 22.51 (C19), 17.57 (C21), 14.17, 12.50 (C18), 11.48.

MS (+APCI) m/z=Found 547.4461; calculated for C$_{33}$H$_{59}$N$_2$O$_4$ 547.4469; −1.5 ppm IR (KBr) ν=3265, 3068, 2919, 2853, 1648 (C=O), 1554 cm$^{-1}$

Synthesis of N-[3-(dibutylamino)propyl] cholanamide (7)

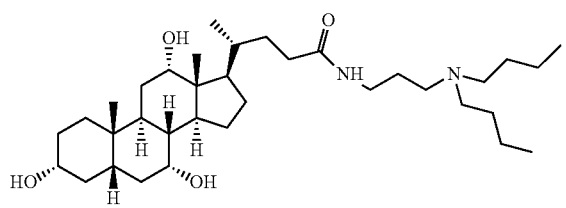

The procedure was followed as above with 3-dibutylaminopropylamine (0.22 mL, 1.18 mmol). Purification of the crude product was done dissolving the product in ethyl acetate (10 mL), removing solid impurities by filtration followed by removing the organic solvent. The product was dried at room temperature under vacuum.

Yield=0.42 g (84%)

Melting point: 145.1-145.9° C.

$^1$H NMR (CDCl$_3$) δ ppm: 0.68 (s, 3H, Me-18) 0.89 (s, 3H, Me-19) 0.92 (d, J=6.3 Hz 3H, Me-21) 1.0-2.439 (m, steroid structure) 2.44 (m, butyl chain) 2.55 (m, butyl chain) 3.33 (m, propyl chain) 3.44 (m, 1H, CH-3) 3.84 (s, 1H, CH-7) 3.97 (s, 1H, CH-12) 7.43 (m, 1H, NH)

Carbon=N/A

MS (+APCI) m/z=577.4931

IR (KBr) ν=3299, 3089, 2919, 2853, 2358, 1727, 1642 (C=O), 1545, 1463 cm$^{-1}$

Synthesis of N-(2-pyrrolidin-1-ylethyl) cholanamide (10)

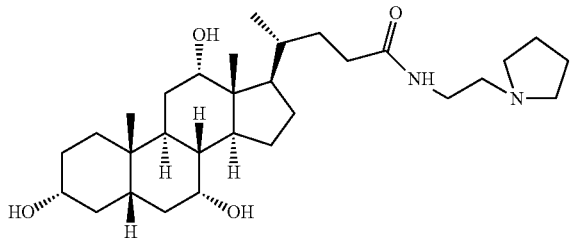

The procedure was followed as above with 1-(2-aminoethyl) pyrrolidine (0.21 mL, 1.8 mmol).

Yield=0.74 g (74%)

Melting point: 96-97.1° C.

$^1$H NMR (CDCl$_3$) δ ppm: 0.68 (s, 3H, Me-18) 0.89 (s, 3H, Me-19) 1.00 (d, J=6.2 Hz, 3H, Me-21) 1.0-2.43 (m, steroid structure) 2.23 (d, J=12.1 Hz, CH$_2$) 2.64 (s 2H, CH$_2$) 3.44 (m 1H, CH-3) 3.84 (s, 1H, CH-7) 3.96 (s, 1H, CH-12) 6.40 (s, 1H, NH)

$^{13}$C NMR (DMSO) δ ppm: 172.45 (C=O), 79.14, 70.98 (C12), 66.21 (C7), 55.02 (CH$_2$), 53.58 (CH$_2$ ring), (46.12, 45.70, 41.49, 37.81, 35.13, 34.35, 32.51, 31.70, 26.18 steroid ring), 41.34 (CH$_2$) 23.08 (CH$_2$ ring), 22.59 (C19), 17.07 (C21), 12.30 (C18).

MS (+APCI) m/z=Found 505.3993; calculated for C$_{30}$H$_{53}$N$_2$O$_4$ 505.4000; −1.4 ppm IR (KBr) ν=3287, 2929, 2862, 2155, 1642 (C=O) cm$^{-1}$ Synthesis of N-[3-(dimethylamino)propyl] cholanamide (12)

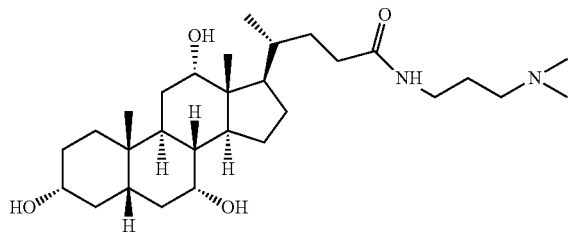

The procedure was followed as above with 3-(dimethylamino)-1-propylamine (0.18 mL, 1.76 mmol).

Yield=0.70 g (70%)

Melting point: 163.2-164.0° C.

$^1$H NMR (CDCl$_3$) δ ppm: 0.67 (s, 2H, Me-18) 0.87 (s, 2H, Me-19) 0.97 (d, J=6.2 Hz, 3H, Me-21) 1.0-2.43 (m, steroid structure) 2.21 (m, CH$_2$) 2.33 (s, 6H, 2CH$_3$) 3.30 (m, J=5.7 Hz, 1H) 3.82 (s, 1H, CH-7) 3.96 (s, 1H, CH-12) 6.97 (s, 1H, NH)

$^{13}$C NMR (DMSO) δ ppm: 176.07 (C=O), 70.99 (C12), 70.41 (C3), 66.23 (C7), 56.42 (CH$_3$), (46.25, 44.96, 41.50, 41.31, 40.14, 35.25, 34.84, 34.36, 32.61, 30.38, 28.51, 27.30, 26.77, 26.17 steroid ring), 45.72 (CH$_3$), 40.47 (CH$_2$), 31.52 (CH$_2$), 22.80, 22.58 (C19), 17.04 (C21), 12.34 (C18).

MS (+APCI) m/z=Found 493.3994; calculated for C$_{29}$H$_{53}$N$_2$O$_4$ 493.4000; −1.2 ppm IR (KBr) ν=3387, 2932, 2862, 2209, 1991 cm$^{-1}$ Synthesis of N-(1-phenyl-4-piperidyl) cholanamide (13)

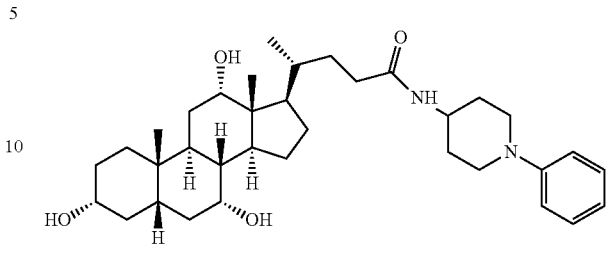

The procedure was followed as above with 4-amino-1-benzylpiperidine (0.34 mL, 1.79 mmol).

Yield=0.88 g (88%)

Melting point: 79.9-86.5° C.

$^1$H NMR (CDCl$_3$) δ ppm: 0.67 (s, 3H, Me-18) 0.89 (s 3H, Me-19) 0.99 (d, J=6.1 Hz, 3H, Me-21) 1.0-2.43 (m, steroid structure) 2.83 (d, J=11.9 Hz) 3.43 (m, 1H, CH-3) 3.48 (d, J=3.2 Hz) 3.83 (s, 1H, CH-7) 3.96 (s, 1H, CH-12) 5.72 (d, J=8.0 Hz, 1H) 7.317 (s, 1H, NH)

$^{13}$C NMR (DMSO) δ ppm: 171.78 (C=O), 138.72, 138.63, (128.65, 128.09, 126.77 aromatic ring), 70.98 (C12), 70.41 (C3), 66.21 (C7), 62.15, 51.97, 51.87, (46.12, 45.71, 41.50, 41.33, 40.51, 40.32, 40.17, 35.29, 35.11, 34.85, 34.36, 32.59, 31.73, 31.62, 30.39, 28.53, 22.77 steroid ring), 27.27 (CH$_2$ ring), 26.19 (CH$_2$ ring) 22.59 (C19), 17.12 (C21), 14.63, 12.31 (C18).

MS (+APCI) m/z=Found 519.4138; calculated for C$_{36}$H$_{57}$N$_2$O$_4$ 581.4313. −61=benzene ring IR (KBr) ν=3279, 3006, 2925, 2810, 2358, 2162, 1782, 1646 (C=O), 1513 cm$^{-1}$ Synthesis of 1-(3-phenylimidazolidin-1-yl) cholanone (14)

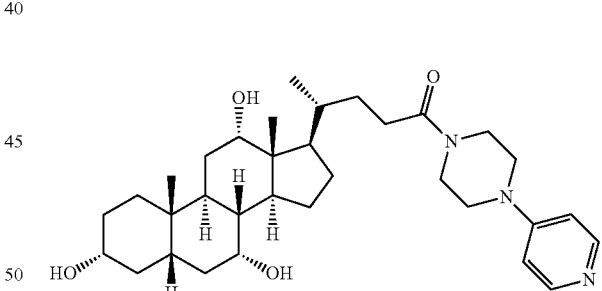

The procedure was followed as above with 1-(4-pyridyl) piperazine (0.24 g, 1.5 mmol).

Yield=0.523 g (53%)

Melting point: 139.6-141.2° C.

$^1$H NMR (CDCl$_3$) δ ppm: 0.68 (s, 3H, Me-18) 0.89 (s, 3H, Me-19) 0.98 (d, 3H, Me-21) 1.0-2.43 (m steroid structure) 2.26 (m 1H) 3.63 (m 1H CH-3) 3.85 (m 1H CH-7) 3.98 (s 1H CH-12) 4.12 (d, J=6.95 Hz, 2H) 6.55-6.81 (m, 2H NH) 8.12-8.45 (m, 2H NH)

$^{13}$C NMR (DMSO) δ ppm: 173.30 (C=O), 171.33, 154.17, 149.80, 108.29, 99.48, 71.02 (C12), 70.41 (C3), 66.21 (C7), 59.58, (45.74, 45.74, 45.12, 40.47, 40.14, 35.27, 34.96, 34.35, 30.70, 30.37, 28.49, 26.17 steroid rings), 27.27 (CH$_2$ ring) 22.77, 22.59 (C19), 17.17, 16.87 (C21), 14.11, 12.28 (C18).

MS (+APCI) m/z=Found 454.3528; calculated for $C_{33}H_{51}N_3O_4$ 553.387. MI—N(Ph)-NCH$_2$CH$_2$ IR (KBr) v=3396, 3250, 2929, 2859, 2158, 1724, 1593, 1515 cm$^{-1}$ Synthesis of 1-[4-(2-hydroxyethyl)piperazin-1-yl]cholanone (15)

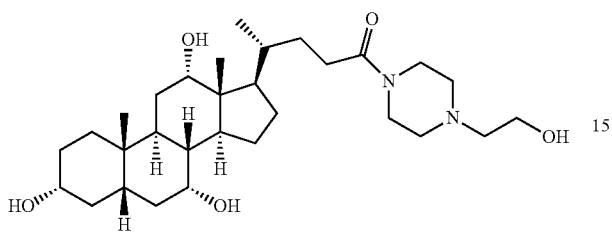

The procedure was followed as above with 1-(2-hydroxyethyl)piperazine (0.2 mL, 1.5 mmol). Proton NMR analysis showed excess of amine present.

Yield=0.4 g (80%)

Melting point: 167.8-168.1° C.

$^1$H NMR (CDCl$_3$) δ ppm: 0.70 (s, 2H, Me-18) 0.90 (s, 2H, Me-19) 1.10 (d, J=5.3 Hz, 3H, Me-21) 1.0-2.43 (m, steroid structure) 2.50-2.63 (m, CH—N) 3.48 (m, J=4.9 1 Hz, CH-3 and CH) 3.64 (d, J=5.3 Hz, CH—N) 3.86 (s, 1H, CH-7) 3.98 (s, 1H, CH-12)

$^{13}$C NMR (DMSO) δ ppm: 170.97 (C=O), 154.56, 71.00 (C12), 70.40 (C3), 66.22 (C7), 60.61, 60.12 (CH$_2$), 58.43 (CH$_2$), 52.93 (CH$_2$ ring), 52.80, (46.08, 43.29, 41.48, 35.26, 35.21, 34.83, 34.35, 31.19, 30.39, 29.48, 28.47, 27.29, 26.17 steroid ring), 45.74 (CH$_2$ ring), 22.81, 22.59 (C19), 17.14 (C21), 14.54, 12.32 (C18).

MS (+APCI) m/z=521.3943

IR (KBr) v=3617, 3414, 2916, 2853, 2810, 1687 (C=O), 1624 cm$^{-1}$

Synthesis of N-octadecylcholanamide (16)

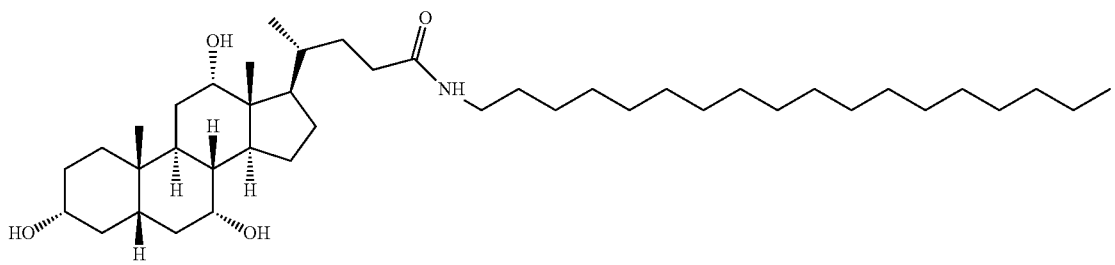

The procedure was followed as above with octadecylamine (0.8 g, 2.9 mmol). Further purification carried out using solvent extraction (×3) between THF/water (30 mL) and chloroform (30 mL). The organic layer was dried over magnesium sulphate and the solvent was evaporated under reduced pressure. The product was dried at room temperature under vacuum.

Yield=0.922 g (90%)

Melting point: 83.6-84.4° C.

$^1$H NMR (CDCl$_3$) δ ppm: 0.66 (s, 3H, Me-18) 0.87 (d, J=3.4 Hz, 3H, Me-19) 0.97 (d, J=5.9 Hz, 3H, Me-21) 1.0-2.43 (m, steroid structure) 1.23 (s, 37H, CH$_2$) 3.2 (q, J=7.3, 6.8 Hz) 3.43 (m, 1H, CH-3) 3.83 (s, 1H, CH-7) 3.96 (s, 1H, CH-12) 5.56 (s, 1H, NH)

$^{13}$C NMR (DMSO) δ ppm: 172.90 (C=O), 172.43, 70.98 (C12), 70.40 (C3), 66.21 (C7), 56.68, (46.15, 45.68, 45.08, 41.48, 36.68, 35.12, 34.35, 31.75, 31.26, 30.34, 29.02, 28.67, 27.13, 26.18 steroid ring), 22.79 (CH$_2$), 22.59 (CH$_2$), 22.57 (C19), 22.06, 17.08 (C21), 13.92 (CH$_2$), 12.31 (C18).

MS (+APCI) m/z=Found 660.5923; calculated for $C_{42}H_{77}N_1O_4$ 660.5925; −0.4 ppm IR (KBr) v=3299, 2916, 2847, 1648 (C=O), 1642 cm$^{-1}$ Synthesis of N-benzylcholanamide (17)

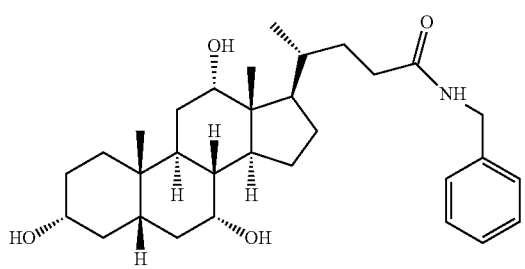

The procedure was followed as above with benzylamine (0.12 mL, 1.1 mmol). The product was recrystallised in dichoromethane.

Yield=0.282 g (56.4%)

Melting point=114.1-114.7° C.

$^1$H NMR (Methanol-d$_4$) δ ppm: 0.69 (s, 2H, Me-18), 0.91 (s, 2H, Me-19), 1.02 (d, J=6.2 Hz, 3H, Me-21), 1.0-2.43 (m, steroid structure) 3.36 (m, 1H, CH-3), 3.78 (s, 1H, H—C-7), 3.94 (s, 1H, CH-12), 4.35 (d, 7.29 (m, J=6.2 Hz, 6H)

$^{13}$C NMR (DMSO) δ ppm: 172.55 (C=O), (139.77, 128.17, 127.06, 126.60 aromatic ring), 70.97 (C12), 70.41 (C3), 66.20 (C7), (46.15, 45.71, 41.89, 40.49, 40.16, 35.28, 35.09, 34.86, 34.36, 34.36, 32.49, 31.77, 30.38, 28.53, 27.30, 26.18 steroid ring), 22.61 (C19), 17.06 (C21), 12.31 (C18).

MS (+APCI) m/z=Found 498.3569; calculated for $C_{31}H_{47}N_1O_4$ 498.3578; −1.8 ppm IR v=3411, 2917, 1644, 1540, 1457 cm$^{-1}$

Synthesis of 2-cholanamidobenzamide (18)

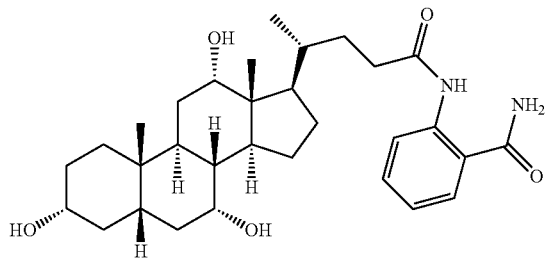

The procedure was followed as above with 2-aminobenzomide (0.5 g, 3.7 mmol). Further separation of the crude product to purify it was carried out with sodium hydrogen carbonate (30 mL) and 2M hydrochloric acid (30 mL). The organic layer was dried over magnesium sulphate and the solvent was evaporated under reduced pressure. The product was dried at room temperature under vacuum.

Melting point: 103-104° C.

$^1$H NMR (CDCl$_3$) δ ppm: 0.69 (s, 3H, Me-18) 0.89 (s, 3H, Me-19) 1.03 (d, J=6.0 Hz, 3H, Me-21) 1.0-2.43 (m steroid structure) 2.10 (s) 3.47 (m, J=7.9 Hz, 1H, CH-3) 3.84 (s, 1H, CH-7) 3.98 (s, 1H, CH-12) 6.25 7.07 (m, ring) 7.52 (d, J=8.3 Hz, ring) 8.62 (d, J=8.4 Hz, 1H, NH) 11.10 (s)

$^{13}$C NMR (CDCl$_3$) δ ppm: 176.74, 176.03 (C=O), (145.05, 137.37, 133.74, 124.55 aromatic ring), 71.47 (C12), 51.28, 51.00, (46.75, 46.58, 45.75, 45.42, 45.09, 44.75, 44.42, 44.09, 43.75, 40.29, 39.61, 31.43, 27.84 steroid ring), 22.27 (C19), 17.56 (C21).

MS (+APCI) m/z=Found 527.3473; calculated for C$_{31}$H$_{46}$N$_5$O$_5$ 527.3479; −1.2 ppm IR (KBr) ν=3350, 3220, 2932, 2865, 1721, 1660 (c=C=O), 1612, 1581 cm$^{-1}$

Synthesis of N-(4-benzoylphenyl)cholanamide (19)

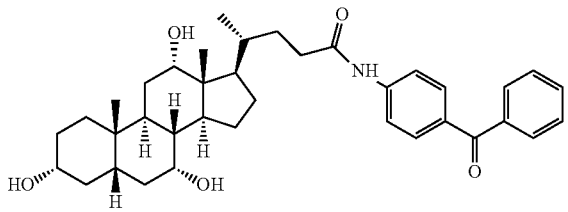

The procedure was followed as above with 4-aminobenzophenone (0.23 g, 1.17 mmol).

Yield=0.1270 g (25.4%)

Melting point: 125.8-127.6° C.

$^1$H NMR (CDCl$_3$) δ ppm: 0.70 (s, 3H, Me-18) 0.90 (s, 2H, Me-19) 1.02 (d, J=6.1 Hz, 3H, Me-21) 1.0-2.43 (m, steroid structure) 3.48 (m, 1H, CH-3) 3.86 (s, 1H, CH-7) 3.99 (s, 1H, CH-12) 7.37-7.65 (m, 6H, ring) 7.65-7.91 (m, 6H, ring) 8.25 (s, 1N, NH)

$^{13}$C NMR (DMSO) δ ppm: 194.48 (C=O), 172.42 (C=O), (143.55, 137.59, 132.14, 131.11, 130.99, 129.30, 128.43, 118.16 aromatic rings), 66.21 (C7), (45.72, 40.50, 40.17, 39.84, 39.50, 39.17, 38.84, 38.50, 35.27, 35.12, 34.36, 34.36, 33.56, 31.29, 30.39, 28.54, 27.31, 26.20 steroid ring), 22.60 (C19), 17.13 (C21), 12.34 (C18).

MS (+APCI) m/z=Found 588.3684; calculated for C$_{37}$H$_{50}$N$_1$O$_5$ 587.36; −0.6 ppm IR (KBr) ν=3317, 3098, 2932, 2865, 1967, 1645, 1584, 1521 cm$^{-1}$

Synthesis of N-(4-vinylphenyl)acetamide (20)

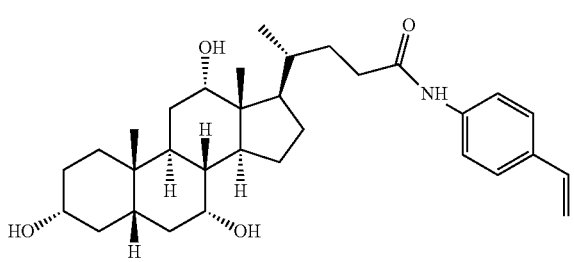

The procedure was followed as above with 4-vinyl aniline (0.42 mL, 3.5 mmol). Further purification with washing product dissolved in ethyl acetate (30 mL) with 2M HCl (30 mL) four times. The organic layer was dried over magnesium sulphate and the solvent was evaporated under reduced pressure. The product was dried at room temperature under vacuum. Proton NMR analysis showed the product contained excess 4-vinyl aniline.

Melting point: N/A $^1$H NMR (CDCl$_3$) δ ppm: 0.69 (s, 3H, Me-18) 0.90 (s, 3H, Me-19) 1.02 (d, J=6.0 Hz, 3H, Me-21) 1.0-2.43 (m, steroid structure) 2.36 (s) 2.62 (s) 3.47 (m, 1H, CH-3OH) 3.87 (s, 1H, CH-7) 3.99 (s, 1H, CH-12) 5.18 (d, J=11.5 Hz, 2H, CH$_2$) 5.67 (d, J=18.0 Hz, 2H, CH$_2$) 6.61 (dd) 7.36 (d, J=5.4 Hz, aromatic) 7.52 (d, J=8.5 Hz, aromatic)

$^{13}$C NMR (DMSO) δ 171.74 (C=O), (153.40, 139.14, 138.93, 131.73, 131.22, 128.96, 128.86, 128.17, 126.58, 126.47, 125.28, 118.85, 117.95, 112.28 aromatic ring, with excess 4-vinyl aniline), (137.30, 136.16, 112.46 C=C), 70.95 (C12), 70.40 (C3), 66.19 (C7), 60.14, (46.06, 45.69, 41.46, 41.34, 40.42, 40.09, 35.27, 35.16, 34.85, 34.35, 33.43, 31.43, 30.35, 28.53, 27.28, 26.16 steroid ring), 22.78, 22.59 (C19), 21.02, 17.11 (C21), 14.48, 12.33 (C18), 10.94.

MS (+APCI) m/z=Found 510.3570; calculated for C$_{32}$H$_{48}$N$_1$O$_4$ 510.3578; −1.5 ppm IR (KBr) ν=3429, 3296, 3101, 3044, 2929, 2868, 2364, 1672 (C=O), 1587, 1521, 1508, 1460 cm$^{-1}$

Synthesis of N-(2-dimethylaminoethyl)cholamide (21)

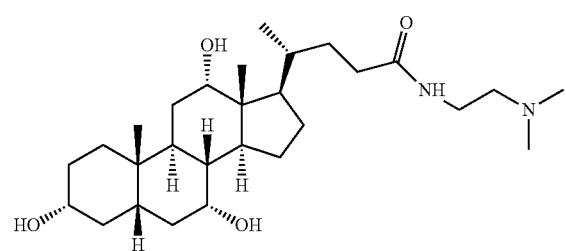

The procedure was followed as above with cholic acid (5 g, 12.2 mmol), triethylamine (2.9 mL, 28.7 mmol), ethylchloroformate (1.3 mL, 12 mmol) and dimethylethylenediamine (1.3 mL, 14.7 mmol).

Yield=3.2185 g (64%)

Melting point: 181-182.2° C.

$^1$H NMR (CDCl$_3$) δ ppm: 0.66 (s, 3H, Me-18) 0.87 (s, 3H, Me-19) 0.98 (d, J=6.0 Hz, 3H, Me-21) 1.0-2.43 (m steroid structure) 2.37 (s, 4H, 2CH$_2$) 2.62 (t, 2H, CH$_2$) 3.39 (d, J=5.7 Hz, CH$_2$ plus CH-3) 3.81 (s, 1H, CH-7) 3.94 (s, 1H, CH-12) 7.17 (s, 1H, NH)

$^{13}$C NMR (CDCl$_3$) δ ppm: 218.02, 178.14, 174.59 (C=O), 73.01, 71.80 (C12), 68.37 (C7), 57.82 (CH$_2$), (46.54, 46.49, 44.98, 44.63, 41.69, 39.73, 39.59, 35.62, 35.49, 34.87, 33.15, 31.75, 30.62, 28.30, 27.70, 26.42 steroid ring), 36.26 (CH$_3$), 23.39, 23.32, 22.58 (C19), 17.55 (C21), 14.73, 12.53 (C18)

MS (+APCI) m/z=Found 479.3835; calculated for C$_{28}$H$_{50}$N$_2$O$_4$ 479.3843 −1.7 ppm IR (KBr) ν=3484, 3250, 3074, 2925, 2865, 1715, 1633, 1551 cm$^{-1}$ Each cholic acid derivative was dissolved in either chloroform or dichloromethane along with a tenfold excess of the alkylating agent. The mixtures were left at room temperature for 4-48 hours. Upon the precipitation of the product, the solid was collected by filtration and washed with solvent, dried and purified if necessary.

Synthesis of 3-cholanamidopropyl(trimethyl)ammonium iodide (24)

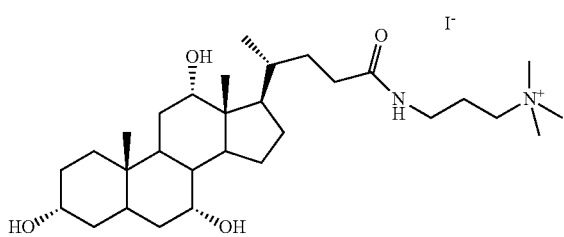 [SMILES: [I-] ; C[C@H](CCC(=O)NCCC[N+](C)(C)C)[C@H]1CCC2C3C(C[C@H](O)[C@@]21C)[C@@]1(C)CC[C@@H](O)CC1C[C@H]3O]

N-[3-(dimethylamino)propyl] cholanamide (12) (0.5 g, 1.0 mmol) was dissolved in DCM (25 mL) along with methyl iodide (1.4 mL, 4.3 mmol). The reaction was left for 48 hours where upon a yellow solid formed. The solid was collected by filtration and washed with chloroform (10 mL) before drying at room temperature under vacuum.

Yield=0.18 g (36%)

Melting point: 134.6-135.4° C.

$^1$H NMR (D$_2$O) δ ppm: 0.70 (s, 3H, Me-18) 0.90 (s, 3H, Me-19) 0.96 (d, J=Hz, 3H, Me-21) 1.0-2.43 (m, steroid structure) 3.11 (s, 9H, 3CH$_3$) 3.30 (ddt, J=17.8 Hz) 3.48 (dd, J=10.4, 5.3 Hz, 1H, CH-3) 3.89 (s, 1H, CH-7) 4.05 (s, 1H, CH-12) 7.65 (s, 1H, NH)

$^{13}$C NMR (DMSO) δ ppm: 212.03, 172.84 (C=O), 79.97, 70.95 (C12), 70.37 (C3), 66.20 (C7), 52.27 (CH$_3$), 52.18, 45.68 (CH$_2$), 40.52 (CH$_2$), (40.43, 40.18, 40.10, 35.27, 34.35, 32.33, 29.95 steroid ring), 22.97, 22.60 (19), 17.11 (C21), 12.31 (C18), 6.83.

MS (+APCI) m/z=Found 507.4150; calculated for C$_{30}$H$_{55}$N$_2$O$_4$ 507.4156; −1.3 ppm IR (KBr) ν=3387, 2929, 2862, 1700, 1642 cm$^{-1}$ Synthesis of 3-cholanamidopropyl-ethyl-dimethyl-ammonium iodide (25)

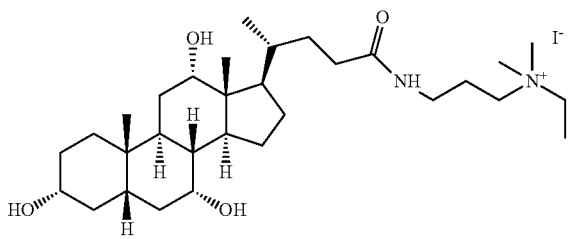

N-[3-(dimethylamino)propyl] cholanamide (12) (0.5 g, 1.0 mmol) was dissolved in DCM (20 mL) along with ethyl iodide (0.4 mL, 1.3 mmol) and methanol (1 mL). The reaction was left for 1 week before the solvent was removed under reduced pressure. The solid was washed with ether (10 mL) and chloroform (10 mL) before drying. The product was a yellow solid.

Yield=0.267 g (53%)

Melting point: 122.5-123.1° C.

$^1$H NMR (D$_2$O) δ ppm: 0.72 (s, 3H, Me-18) 0.92 (s, 3H, Me-19) 0.97 (d, 3H, Me-21) 1.0-2.43 (m, steroid structure) 3.04 (s, 6H, CH$_2$) 3.21-3.34 (m, 4H, 2CH$_2$) 3.38 (q, J=7.3 Hz, 2H, CH$_2$) 3.44-3.62 (m, 1H, CH-3) 3.89 (s, 1H, CH-7) 4.06 (s, 1H, CH-12) 7.67 (s, 1H, NH)

$^{13}$C NMR (DMSO) δ ppm: 197.83, 172.88 (C=O), 70.96 (C12), 70.37 (C3), 66.20 (C7), 60.46, 58.59 (CH$_3$), 49.59, 49.52, (45.96, 41.46, 41.38, 40.51, 40.17, 39.84, 39.51, 39.42, 39.17, 39.01, 38.84, 38.51, 35.47, 35.25, 35.15, 34.87, 34.34, 32.35, 30.35, 28.55, 27.26, 26.20 steroid ring), 45.68 (CH$_2$), 31.52 (CH$_2$), 22.77, 22.59 (C19), 22.52 (CH$_2$), 17.10 (C21), 12.31 (C18), 7.76.

MS (+APCI) m/z=Found 521.4305; calculated for C$_{31}$H$_{57}$N$_2$O$_4$ 521.4313; −1.5 ppm IR (KBr) ν=3420, 3256, 2913, 2856, 2243, 1639 (C=O) cm$^{-1}$ Synthesis of 3-cholanamidopropyl-propyl-dimethyl-ammonium iodide (26)

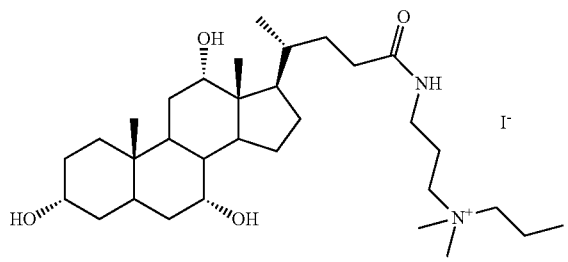 [SMILES: CCC[N+](C)(C)CCCNC(=O)CC[C@@H](C)[C@H]1CCC2C3C(C[C@H](O)[C@@]21C)[C@@]1(C)CC[C@@H](O)CC1C[C@H]3O ; [I-]]

N-[3-(dimethylamino)propyl] cholanamide (12) (0.5 g, 1.0 mmol) was dissolved in DCM (20 mL) along with 1-iodopropane (1.5 mL, 5.0 mmol) and methanol (1 mL). The reaction was left for 1 week before solvent extraction (×3) between dichloromethane (20 mL) and water (20 mL). The organic layer was dried with magnesium sulphate before being removed under reduced pressure. The product was a white solid which was dried at room temperature under vacuum.

Yield=0.233 g (46%)

Melting point: 108.1-108.9° C.

$^1$H NMR (DMSO) δ ppm: 0.57 (s, 3H, Me-18) 0.79 (s, 3H, Me-19) 0.86-0.94 (m, 37H, Me-21 plus 2CH$_2$) 1.0-2.43 (m, steroid structure) 2.94-3.28 (m, 14H) 3.61 (s, 1H, 7CH) 3.77 (s, 1H, 12CH) 3.99 (d, J=, 1H 3OH) 4.10 (d, J=, 1H, 7OH) 4.32 (d, J=4.0 Hz, 1H, 12OH) 7.88 (t, J=5.7 Hz, NH)

$^{13}$C NMR (DMSO) δ ppm: 172.92 (C=O), 70.97 (C12), 70.37 (C3), 66.20 (C7), 64.37, 61.10, 50.20, 50.16, (45.97, 35.45, 35.15, 34.86, 34.34, 32.37, 30.34, 28.53, 26.20 steroid ring), 45.68 (CH$_3$), 31.54 (CH$_2$), 27.26 (CH$_2$), 22.58 (C19), 17.10 (C21), 15.32 (CH$_3$), 12.31 (C18), 10.45 (CH$_2$).

MS (+APCI) m/z=Found 535.4461; calculated for C$_{32}$H$_{59}$N$_2$O$_4$ 535.4469; −1.6 ppm IR (KBr) ν=3396, 2935, 2865, 2246, 2124, 1706, 1645 (C=O), 1533 cm$^{-1}$

Synthesis of 3-cholanamidopropyl-butyl-dimethyl-ammonium iodide (27)

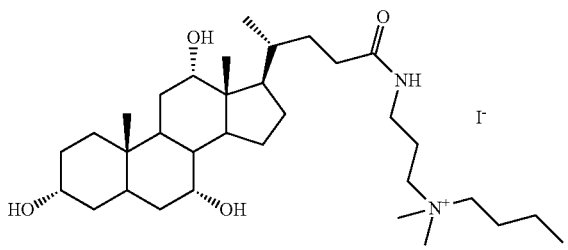 [SMILES: CCCC[N+](C)(C)CCCNC(=O)CC[C@@H](C)[C@H]1CCC2C3C(C[C@H](O)[C@@]21C)[C@@]1(C)CC[C@@H](O)CC1C[C@H]3O ; [I-]]

N-[3-(dimethylamino)propyl] cholanamide (12) (0.5 g, 1.0 mmol) was dissolved in DCM (20 mL) along with 1-iodobutane (1.2 mL, 4 mmol) and methanol (1 mL). The reaction was left for 1 week before solvent extraction (×3) between dichloromethane (20 mL) and water (20 mL). The organic layer was dried with magnesium sulphate before being removed under reduced pressure. The product was a white solid which was dried at room temperature under vacuum.

Yield=0.3115 g (62%)

Melting point: 125.8-126.4° C.

$^1$H NMR (D$_2$O) δ ppm: 0.68 (s, 3H, Me-18) 0.88 (s, H, Me-19) 0.84-1.00 (m, 5H, Me-21 plus CH$_2$) 1.0-2.43 (m, steroid structure) 3.02 (s, 6H, CH$_2$) 3.14-3.32 (m, 6H, CH$_2$) 3.47 (m, 1H, 3CH) 3.86 (s, 1H, 7CH) 4.02 (s, 1H, 12CH)

MS (+APCI) m/z=Found 549.4619; calculated for C$_{33}$H$_{61}$N$_2$O$_4$ 549.4626; −1.2 ppm IR (KBr) ν=3378, 2932, 2865, 2358, 2337, 2155, 2009, 1976, 1651, 1633 (C=O), 1539 cm$^{-1}$

Synthesis of 3-cholanamidopropyl-pentyl-dimethyl-ammonium iodide (28)

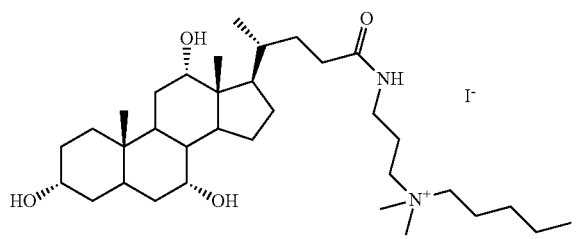 [SMILES: CCCCC[N+](C)(C)CCCNC(=O)CC[C@@H](C)[C@H]1CCC2C3C(C[C@H](O)[C@@]21C)[C@@]1(C)CC[C@@H](O)CC1C[C@H]3O ; [I-]]

N-[3-(dimethylamino)propyl] cholanamide (12) (0.5 g, 1 mmol) was dissolved in chloroform (75 mL) along with 1-iodopentane (1.5 mL) and methanol (1 mL). The reaction was left for 1 week before solvent extraction (×3) between chloroform (75 mL) and water (70 mL). The organic layer was dried with magnesium sulphate before being removed under reduced pressure. The product was a white solid which was dried at room temperature under vacuum.

Yield=0.077 g (77%)

Melting point: 107.9-108.3° C.

$^1$H NMR (Methanol-d$_4$) δ ppm: 0.67 (s 3H Me-18) 0.83-1.05 (m 10H Me-21 plus CH$_2$) 1.0-2.439 (m steroid structure) 3.04 (s 6H CH$_2$) 3.47 (m 1H 3CH) 3.76 (s 1H 7CH) 3.92 (d J=3.3 Hz 1H 12CH)

$^{13}$C NMR (DMSO) δ ppm: 170.89 (C=O), 154.50, 71.01 (C12), 70.42 (C3), 66.22 (C7), 60.58, 57.47, 57.41 (CH$_3$), 53.14, 52.55, 52.46, 48.55, 46.07, 45.02, 43.30, 41.52, 41.33, 40.93, 35.30, 35.22, 34.85, 29.49, 28.47, 28.35, 27.30, 26.17 steroid ring), 45.74 (CH$_3$), 40.50 (CH$_2$), 30.37 (CH$_2$), 34.34 (CH$_2$), 31.17 (CH$_2$), 22.79 (CH$_2$), 22.57 (C19), 20.03, 17.12 (C21), 14.51, 13.84 (CH$_2$), 12.29 (C18).

MS (+APCI) m/z=563.4767

IR (KBr) ν=3381 2929 2871 1645 (C=O) 1533 cm$^{-1}$

Synthesis of 3-cholanamidopropyl-hexyl-dimethyl-ammonium iodide (29)

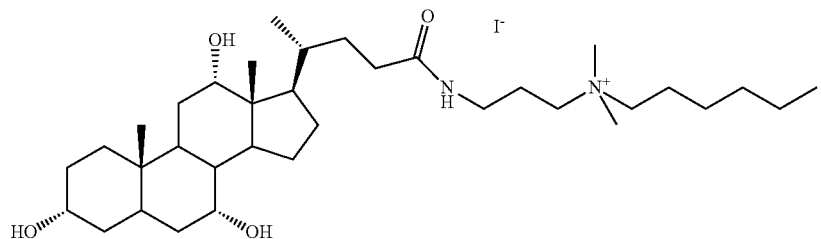 [SMILES: CCCCCC[N+](C)(C)CCCNC(=O)CC[C@@H](C)[C@H]1CCC2C3C(C[C@H](O)[C@@]21C)[C@@]1(C)CC[C@@H](O)CC1C[C@H]3O ; [I-]]

N-[3-(dimethylamino)propyl] cholanamide (12) (0.5 g, 1 mmol) was dissolved in chloroform (15 mL) along with 1-iodohexane (2.1 mL, 6.8 mmol) and methanol (1 mL). The reaction was left for 5 days before solvent was removed under reduced vacuum. The product was purified by washing with diethyl ether was collected by filtration and dried at room temperature under vacuum. The product was an orange solid.

Yield=0.34 g (68%)

Melting point: 101.7-102.3° C.

$^1$H NMR (Methanol-d$_4$) δ ppm: 0.68 (s, 3H, Me-18) 0.90 (d, J=5.6 Hz, 6H) 1.01 (d, J=5.6 Hz, 3H, Me-21) 1.0-2.43

(m, steroid structure) 1.15 (td, J=7.0, 0.8 Hz) 3.04 (s, 6H, CH₂) 3.47 (m, 1H, 3CH) 3.77 (s, 1H, 7CH) 3.92 (s, 1H, 12CH)

¹³C NMR (DMSO) δ ppm: 172.86 (C=O), 70.96 (C12), 70.37 (C3), 66.20 (C7), 62.99, 60.98, 50.12, (45.98, 35.46, 35.13, 30.05, 29.48, 28.54, 27.26, 26.20 steroid ring), 45.68 (CH₃), 34.34 (CH₂), 30.65 (CH₂), 31.55 (CH₂), 25.40, 22.59 (C19), 21.87 (CH₂), 21.59, 17.10 (C21), 13.81 (CH₃), 12.32 (C18), 9.10 (CH₂).

MS (+APCI) m/z=Found 577.4949; calculated for C₃₅H₆₅N₂O₄ 577.4939; 1.8 ppm

IR (KBr) ν=3390, 2925, 2859, 1654 (C=O) cm⁻¹

Synthesis of 3-cholanamidopropyl-benzyl-dimethyl-ammonium iodide (30)

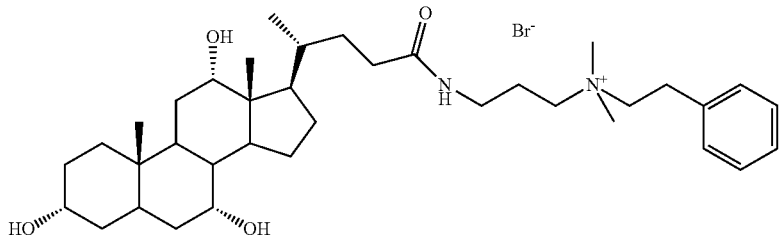 [SMILES: C[C@H](CCC(=O)NCCC[N+](C)(C)CCc1ccccc1)[C@H]1CCC2C3C(C[C@H](O)[C@@]21C)[C@@]1(C)CC[C@@H](O)CC1C[C@H]3O ; [Br-]]

N-[3-(dimethylamino)propyl] cholanamide (12) (0.5 g, 1 mmol) was dissolved in chloroform (20 mL) along with 2-phenylethyl bromide (1.36 mL, 5.4 mmol) and methanol (1 mL). The reaction was left for 24 hours before solvent was removed using a rotary evaporator. The resulting solid was washed with diethyl ether (10 mL) and dried under vacuum at room temperature. The product was a white solid.

Melting point: 103.8-105° C.

¹H NMR (CDCl₃) δ ppm: 0.58 (s, 2H, Me-18) 0.81 (s, 2H, Me-19) 0.92 (d, 3H, Me-21) 1.0-2.43 (m, steroid structure) 2.49 (p, J=1.9 Hz, 14H) 2.55-2.77 (m, 2H), 2.99 (s, 8H) 3.15-3.27 (m, 1H) 3.49 (t, J=6.6 Hz, 1H, 3CH) 3.60 (s, 1H, 7CH) 3.77 (s, 1H, 12CH) 4.05 (dd, J=22.2, 3.3 Hz, 1H, 3OH) 4.10 (d, 1H, 7OH) 4.32 (d, J=4.0 Hz, 1H, 12OH), ¹³C NMR (DMSO) δ ppm: 172.89 (C=O), (140.23, 128.25, 126.21, 125.98 aromatic ring), 70.96 (C12), 70.38 (C3), 50.13, (45.68, 35.47, 34.85, 34.83, 34.35, 32.36, 31.65, 26.20 steroid ring), 23.54 (CH₂), 22.54 (C19), 17.10 (C21), 12.32 (C18).

MS (+APCI) m/z=583.4473

IR (KBr) ν=3362, 3059, 3023, 2925, 2859, 1645 (C=O) cm⁻¹

Synthesis of 3-cholanamidopropyl-dimethyl-octadecyl-ammonium iodide (31)

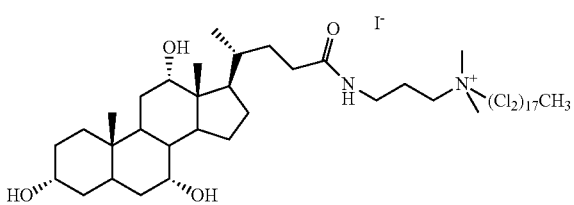

N-[3-(dimethylamino)propyl] cholanamide (12) (0.5 g, 1 mmol) was dissolved in chloroform (15 mL) along with 1-iodo-octadecane (2.4 g, 5 mmol) and methanol (1 mL). The reaction was left for 72 hours before solvent was removed using a rotary evaporator. The resulting solid was washed with diethyl ether (10 mL) before being collected by filtration and dried under vacuum at room temperature. The product was a yellow solid.

Yield=0.30 g (60%)

Melting point: 115.3-116.4° C.

¹H NMR (Methanol-d₄) δ ppm: 0.68 (s, 3H, Me-18) 0.84 (s, 3H, Me-19) 1.01 (d, 3H, Me-21) 1.0-2.43 (m, steroid structure) 1.26 (s, 9H) 2.23 (s, 7H) 3.05 (s) 3.15 (t) 3.27 (m) 3.44 (m, 1H, CH-3OH) 3.76 (s, 1H, CH-7OH) 3.92 (s, 1H, CH-12OH)

¹³C NMR (DMSO) δ ppm: 172.30 (C=O), 70.98 (C12), 66.21 (C7), (46.21, 45.70, 34.85, 34.35, 31.80, 31.27, 30.34, 29.43, 28.77, 28.51, 27.26, 26.34, 26.17 steroid ring), 22.56 (C19), 22.06, 17.04 (C21), 13.91 (CH₂), 12.29 (C18).

MS (+APCI) m/z=754.6801

IR (KBr) ν=3362, 2922, 2850, 1639 (C=O) cm⁻¹

Synthesis of 3-cholanamidopropyl-(2,2-dimethyl-propanoyloxymethyl)-dimethyl-ammonium chloride (32)

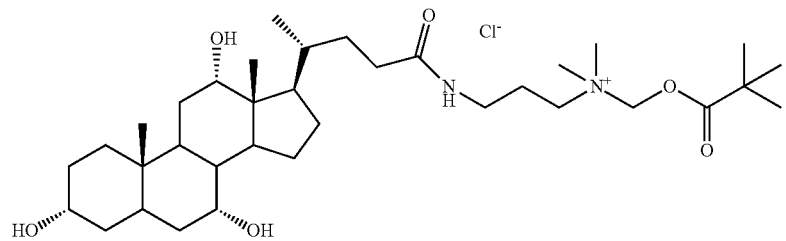 [SMILES: C[C@H](CCC(=O)NCCC[N+](C)(C)COC(=O)C(C)(C)C)[C@H]1CCC2C3C(C[C@H](O)[C@@]21C)[C@@]1(C)CC[C@@H](O)CC1C[C@H]3O ; [Cl-]]

N-[3-(dimethylamino)propyl] cholanamide (12) (0.5 g, 1 mmol) was dissolved in chloroform (20 mL) along with chloromethyl pivalate (1.44 g, 5 mmol) and methanol (1 mL). The reaction was left for 12 hours before solvent was removed using a rotary evaporator. The product was purified by washing with diethyl ether before being collected by filtraction and dried at room temperature under vacuum. The product was a white solid.

Yield=0.335 g (66%)

Melting point: 127.9-128.3° C.

$^1$H NMR (CDCl$_3$) δ ppm: 0.57 (s, 3H, Me-18) 0.80 (s, 3H, Me-19) 1.08 (d, 3H, Me-21) 1.0-2.43 (m, steroid structure) 2.70 (s) 3.05 (s) 3.36 (dd, J=15.7, 8.7 Hz, CH-3) 3.60 (s, 1H, CH-7) 4.01 (d, J=3.3 Hz, 1H, 3OH) 4.10 (d, J=4.1 Hz, 1H, 7OH) 4.34 (d, J=4.1 Hz, 1H, 12OH) 5.25 (s, 2H) 5.85 (s, 1H) 7.93 (t, J=5.7 Hz, 1H, NH)

$^{13}$C NMR (DMSO) δ 179.30 (C=O), 172.96 (C=O), 70.96 (C12), 66.20 (C7), 54.42 (CH$_3$), 47.85, (46.00, 45.70, 41.92, 34.86, 34.35, 27.24, 26.98, 26.43 steroid ring), 24.19, 22.59 (C19), 17.09 (C21), 12.31 (C18).

MS (+APCI) m/z=607.4669

IR (KBr) ν=3402, 3362, 2932, 2871, 2470, 1760, 1706, 1624 (C=O) cm$^{-1}$

Synthesis of 3-cholanamidopropyl-dimethyl-(2-phenylethyl)ammonium bromide (33)

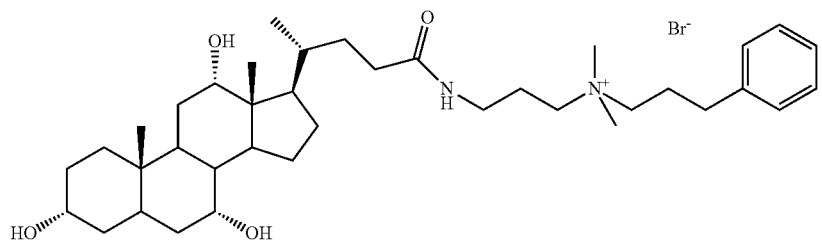 [SMILES: C[C@H](CCC(=O)NCCC[N+](C)(C)CCCc1ccccc1)[C@H]1CCC2C3C(C[C@H](O)[C@@]21C)[C@@]1(C)CC[C@@H](O)CC1C[C@H]3O ; [Br-]]

N-[3-(dimethylamino)propyl] cholanamide (12) (0.5 g, 1 mmol) was dissolved in chloroform (20 mL) along with 1-bromo-3-phenylpropane (1.52 mL, 5 mmol) and methanol (1 mL). The reaction was left for 12 hours before solvent was removed using a rotary evaporator. The product was purified by washing with diethyl ether (10 mL) was collected by filtration and dried at room temperature under vacuum. The product was a white solid.

Yield=0.4 g (80%)

Melting point: 176.8-177.4° C.

$^1$H NMR (DMSO) δ ppm: 0.58 (s, 3H, Me-18) 0.82 (s, 3H, Me-19) 0.95 (d, J=5.6 Hz, 3H, Me-21) 1.10 (d, J=7.0 Hz) 3.12 (d, J=14.5 Hz) 3.61 (m) 3.78 (m) 4.00 (d, 1H, 3OH) 4.10 (d, 1H, 7OH) 4.34 (d, 1H, 12OH) 7.28 (m, 8H, aromatic) 7.93 (m, 1H, NH)

$^{13}$C NMR (DMSO) δ: 172.24 (C=O), (133.08, 128.86, 127.54 aromatic ring), 35.10, 34.35, 22.60 (C19), 17.12 (C21), 12.31 (18).

MS (+APCI) m/z=611.4411

IR (KBr) ν=3373, 3026, 2929, 2859, 1691 (C=O), 1645 cm$^{-1}$

Synthesis of 3-cholanamidopropyl-allyl-dimethyl-ammonium;bromide (34)

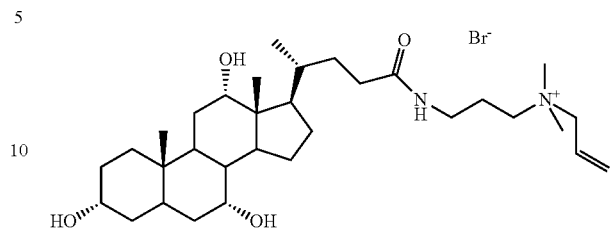

N-[3-(dimethylamino)propyl] cholanamide (12) (0.5 g, 1 mmol) was dissolved in chloroform (20 mL) along with allyl bromide (1.52 mL, 5 mmol) and methanol (1 mL). The reaction was left for 12 hours before solvent was removed using a rotary evaporator. The product was purified by washing with diethyl ether was collected by filtration and dried at room temperature under vacuum. The product was a white solid.

Yield=0.19 g (40%)

Melting point: 121.3-121.9° C.

$^1$H NMR (CDCl$_3$) δ ppm: 0.68 (s, 3H, Me-18) 0.89 (s, 3H, Me-19) 0.85-1.61 (m, 29H) 1.00 (d, 3H, Me-21) 1.0-2.43 (m, steroid structure) 3.04 3.76 (s, 1H, CH-3) 3.87-4.13 (m, 6H) 5.61-5.76 (m, 3H) 5.93-6.17 (m, 2H), 7.88 (s, 1H, NH)

$^{13}$C NMR (DMSO) δ ppm: 172.88 (C=O), 127.60 (C=C), 125.76 (C=C), 70.96 (C12), 70.37 (C3), 66.20 (C7), 65.11, 61.12, 49.73, (45.97, 45.68, 35.26, 34.35, 28.53, 27.29, 26.20 steroid ring), 31.55 (CH$_2$—Br), 25.04 (CH$_2$), 22.56 (C19), 17.11 (C21), 12.31 (C18).

MS (+APCI) m/z=Found 533.4307; calculated for C$_{32}$H$_{57}$N$_2$O$_4$ 533.4313; −1.1 ppm IR (KBr) ν=3368, 3077, 2925, 2862, 2710, 1733, 1651 (C=O), 1633, 1466 cm$^{-1}$ Synthesis of 3-cholanamidopropyl-cyclopentyl-dimethyl-ammonium bromide (35)

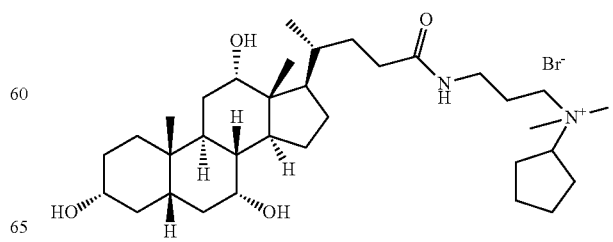

N-[3-(dimethylamino)propyl] cholanamide (12) (0.5 g, 1 mmol) was dissolved in DCM (10 mL) along with) of cyclopentyl bromide (0.9 mL, 10 mmol). The reaction was left for 72 hours where the product precipitated out. It was collected by filtration and dried at room temperature under vacuum. The product was a white solid.

Melting point: 102.6-103° C.

$^{1}$H NMR (DMSO) δ ppm: 0.57 (d, J=1.4 Hz, 3H Me-18) 0.76-0.97 (m, 6H, Me-19 and Me-21) 1.0-2.43 (m, steroid structure) 2.13 (s, dimethyl) 3.14 (s, 3H) 3.4-3.55 (m, 1H, CH-3OH) 3.60 (s 1H CH-7OH) 3.77 (s, 1H, CH-12OH) 3.94-4.18 (m, 4H) 4.32 (t, J=3.9 Hz, 1H) 5.35 (s, 1H, NH)

$^{13}$C NMR (DMSO) δ ppm: 216.00, 138.38 (C=O), 70.92 (C19), 70.38 (C21), 66.17 (C18), 60.48 (CH—Br), (45.71, 43.19, 41.39, 40.51, 40.17, 36.53, 35.28, 34.89, 34.35, 30.64, 30.37, 30.35, 30.18, 28.51, 26.19 steroid ring), 25.66, 24.51 (CH$_2$ ring), 22.59 (C19), 21.64, 16.91 (C21), 12.29 (C18).

MS (+APCI) m/z=562.4448

IR (KBr) ν=3368, 2932, 2865, 2355, 1715 (C=O), 1578, 1460 cm$^{-1}$

Synthesis of
3-cholanamidoethylyl(trimethyl)ammonium iodide
(36)

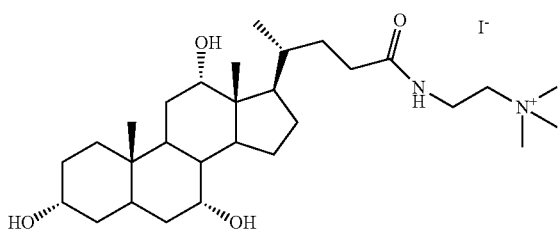 [SMILES: C[C@H](CCC(=O)NCC[N+](C)(C)C)[C@H]1CCC2C3C(C[C@H](O)[C@@]21C)[C@@]1(C)CC[C@@H](O)CC1C[C@H]3O ; [I-]]

N-[3-(dimethylamino)ethyl] cholanamide (21) (0.5 g, 1.0 mmol) was dissolved in DCM (20 mL) along with methyl iodide (0.3 mL, 2.1 mmol). The reaction was left for 12 hours where upon a solid formed and the solvent had evaporated. Diethyl ether (10 mL) was added to the flask and the solid was collected by filtration before being washed with chloroform (10 mL). The product was dried at room temperature under vacuum.

Yield=0.314 g (63%)

Melting point: 215.3-216.1° C.

$^{1}$H NMR (D$_2$O) δ ppm: 0.70 (s, 3H, Me-18) 0.90 (s, 3H, Me-19) 0.96 (d, J=Hz, 3H, Me-21) 1.0-2.43 (m, steroid structure) 3.11 (s, 9H, 3CH$_3$) 3.30 (ddt, J=17.8 Hz) 3.48 (dd, J=10.4, 5.3 Hz, 1H, CH-3) 3.89 (s, 1H, CH-7) 4.05 (s, 1H, CH-12) 7.65 (s, 1H, NH)

$^{13}$C NMR (DMSO) δ ppm: 212.03, 172.84 (C=O), 79.97, 70.95 (C12), 70.37 (C3), 66.20 (C7), 52.27 (CH$_3$), 52.18, 45.68 (CH$_2$), 40.52 (CH$_2$), (40.43, 40.18, 40.10, 35.27, 34.35, 32.33, 29.95 steroid ring), 22.97, 22.60 (19), 17.11 (C21), 12.31 (C18), 6.83.

MS (+APCI) m/z=Found 493.3991; calculated for C$_{29}$H$_{53}$N$_2$O$_4$ 493.4000; −1.8 ppm IR (KBr) ν=3423, 3241, 2935, 2862, 2252, 2118, 1663, 1618, 1539 cm$^{-1}$ Synthesis of
3-cholanamidoethylyl-ethyl-dimethyl-ammonium
iodide (37)

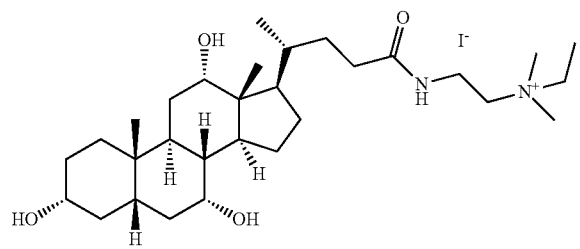

N-[3-(dimethylamino)ethyl] cholanamide (21) (0.5 g, 1.0 mmol) was dissolved in DCM (20 mL) along with ethyl iodide (0.4 mL, 1.3 mmol) and methanol (1 mL). The reaction was left for 12 hours before the solvent was removed under reduced pressure. The solid was washed with ether (10 mL) and chloroform (10 mL) before drying. The product was a yellow solid.

Yield=0.280 g (56%)

Melting point: 142.3-142.7° C.

$^{1}$H NMR (D$_2$O) δ ppm: 0.72 (s, 3H, Me-18) 0.92 (s, 3H, Me-19) 0.97 (d, 3H, Me-21) 1.0-2.43 (m, steroid structure) 3.04 (s, 6H, CH$_2$) 3.21-3.34 (m, 4H, 2CH$_2$) 3.38 (q, J=7.3 Hz, 2H, CH$_2$) 3.44-3.62 (m, 1H, CH-3) 3.89 (s, 1H, CH-7) 4.06 (s, 1H, CH-12) 7.67 (s, 1H, NH)

$^{13}$C NMR (DMSO) δ ppm: 197.83, 172.88 (C=O), 70.96 (C12), 70.37 (C3), 66.20 (C7), 60.46, 58.59 (CH$_3$), 49.59, 49.52, (45.96, 41.46, 41.38, 40.51, 40.17, 39.84, 39.51, 39.42, 39.17, 39.01, 38.84, 38.51, 35.47, 35.25, 35.15, 34.87, 34.34, 32.35, 30.35, 28.55, 27.26, 26.20 steroid ring), 45.68 (CH$_2$), 31.52 (CH$_2$), 22.77, 22.59 (C19), 22.52 (CH$_2$), 17.10 (C21), 12.31 (C18), 7.76.

MS (+APCI) m/z=Found 507.4147; calculated for C$_{30}$H$_{55}$N$_2$O$_4$ 507.4156; −1.8 ppm IR (KBr) ν=3387, 2932, 2862, 2689, 1706, 1648 (C=O), 1533 cm$^{-1}$ Synthesis of
3-cholanamidopropyl-propyl-dimethyl-ammonium
iodide (38)

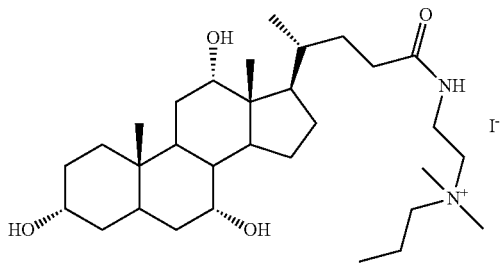 [SMILES: CCC[N+](C)(C)CCNC(=O)CC[C@@H](C)[C@H]1CCC2C3C(C[C@H](O)[C@@]21C)[C@@]1(C)CC[C@@H](O)CC1C[C@H]3O ; [I-]]

N-[3-(dimethylamino)ethyl] cholanamide (21) (0.5 g, 1.0 mmol) was dissolved in DCM (20 mL) along with 1-iodopropane (0.5 mL, 1.7 mmol) and methanol (1 mL). The reaction was left for 6 days before the solvent was removed under reduced pressure. The solid was washed with diethyl ether (10 mL) and collected by filtration. Further purification was carried out by washing the crude product with diethyl ether (2×10 mL) and chloroform (2×10 mL). The product was a white solid which was dried at room temperature under vacuum.

Yield=0.283 g (56%)
Melting point: 108.1-108.9° C.
$^1$H NMR (DMSO) δ ppm: 0.57 (s, 3H, Me-18) 0.79 (s, 3H, Me-19) 0.86-0.94 (m, 37H, Me-21 plus 2CH$_2$) 1.0-2.43 (m, steroid structure) 2.94-3.28 (m, 14H) 3.61 (s, 1H, 7CH) 3.77 (s, 1H, 12CH) 3.99 (d, J=, 1H 3OH) 4.10 (d, J=, 1H, 7OH) 4.32 (d, J=4.0 Hz, 1H, 12OH) 7.88 (t, J=5.7 Hz, NH)
$^{13}$C NMR (DMSO) δ ppm: 172.92 (C=O), 70.97 (C12), 70.37 (C3), 66.20 (C7), 64.37, 61.10, 50.20, 50.16, (45.97, 35.45, 35.15, 34.86, 34.34, 32.37, 30.34, 28.53, 26.20 steroid ring), 45.68 (CH$_3$), 31.54 (CH$_2$), 27.26 (CH$_2$), 22.58 (C19), 17.10 (C21), 15.32 (CH$_3$), 12.31 (C18), 10.45 (CH$_2$).
MS (+APCI) m/z=Found 521.4303; calculated for $C_{31}H_{57}N_2O_4$ 521.4313; −1.9 ppm
IR (KBr) ν=3390, 2935, 2862, 2243, 2121, 1651 (C=O), 1536 cm$^{-1}$ Synthesis of
3-cholanamidoethyl-butyl-dimethyl-ammonium iodide (39)

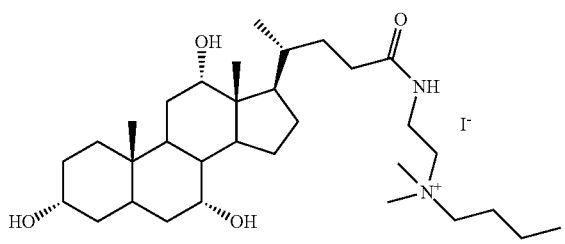 [SMILES: CCCC[N+](C)(C)CCNC(=O)CC[C@@H](C)[C@H]1CCC2C3C(C[C@H](O)[C@@]21C)[C@@]1(C)CC[C@@H](O)CC1C[C@H]3O ; [I-]]

N-[3-(dimethylamino)propyl] cholanamide (21) (0.5 g, 1.0 mmol) was dissolved in DCM (20 mL) along with 1-iodobutane (0.6 mL, 2 mmol) and methanol (1 mL). The reaction was left for 3 days where a precipitate formed. The crude product was collected by filtration and washed with chloroform (15 mL). The product was a white solid which was dried at room temperature under vacuum.

Yield=0.338 g (67%)
Melting point: 186.4-187.4° C.
$^1$H NMR (D$_2$O) δ ppm: 0.68 (s, 3H, Me-18) 0.88 (s, H, Me-19) 0.84-1.00 (m, 5H, Me-21 plus CH$_2$) 1.0-2.43 (m, steroid structure) 3.02 (s, 6H, CH$_2$) 3.14-3.32 (m, 6H, CH$_2$) 3.47 (m, 1H, 3CH) 3.86 (s, 1H, 7CH) 4.02 (s, 1H, 12CH)

MS (+APCI) m/z=Found 535.4458; calculated for $C_{32}H_{59}N_2O_4$ 535.4469; −2.1 ppm
IR (KBr) ν=3484, 3432, 3250, 3071, 2922, 2865, 1633 (C=O), 1551 cm$^{-1}$ Synthesis of
3-cholanamidoethyl-pentyl-dimethyl-ammonium iodide (40)

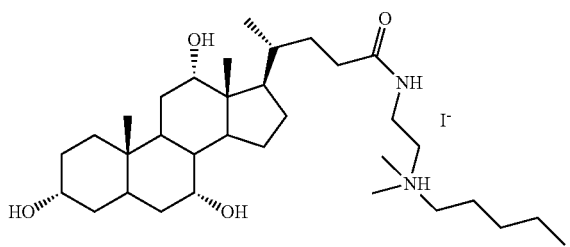

N-[3-(dimethylamino)ethyl] cholanamide (21) (0.5 g, 1 mmol) was dissolved in DCM (20 mL) along with 1-iodopentane (0.6 mL, 1.9 mmol) and methanol (1 mL). The reaction was left for 3 days where a precipitate formed. The product was collected by filtration, washed with chloroform (20 mL) and dried at room temperature under vacuum. The product was a white solid.

Yield=0.396 g (79%)
Melting point: 139.6-141.2° C.
$^1$H NMR (Methanol-d$_4$) δ ppm: 0.67 (s 3H Me-18) 0.83-1.05 (m 10H Me-21 plus CH$_2$) 1.0-2.439 (m steroid structure) 3.04 (s 6H CH$_2$) 3.47 (m 1H 3CH) 3.76 (s 1H 7CH) 3.92 (d J=3.3 Hz 1H 12CH)
$^{13}$C NMR (DMSO) δ ppm: 170.89 (C=O), 154.50, 71.01 (C12), 70.42 (C3), 66.22 (C7), 60.58, 57.47, 57.41 (CH$_3$), 53.14, 52.55, 52.46, 48.55, 46.07, 45.02, 43.30, 41.52, 41.33, 40.93, 35.30, 35.22, 34.85, 29.49, 28.47, 28.35, 27.30, 26.17 steroid ring), 45.74 (CH$_3$), 40.50 (CH$_2$), 30.37 (CH$_2$), 34.34 (CH$_2$), 31.17 (CH$_2$), 22.79 (CH$_2$), 22.57 (C19), 20.03, 17.12 (C21), 14.51, 13.84 (CH$_2$), 12.29 (C18).
MS (+APCI) m/z=Found 549.4618; calculated for $C_{33}H_{61}N_2O$ 4549.4626; −1.4 ppm
IR (KBr) ν=3484, 3250, 3071, 2925, 2868, 1627 (C=O), 1560 cm$^{-1}$ Synthesis of
3-cholanamidoethyl-hexyl-dimethyl-ammonium iodide (41)

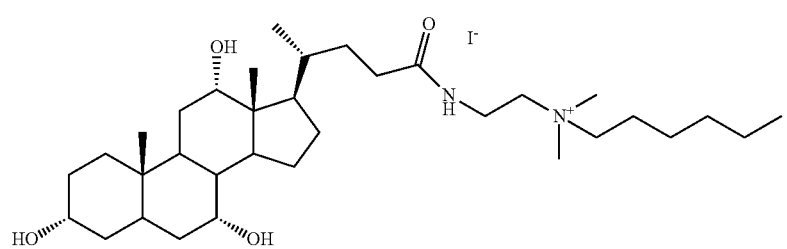 [SMILES: CCCCCC[N+](C)(C)CCNC(=O)CC[C@@H](C)[C@H]1CCC2C3C(C[C@H](O)[C@@]21C)[C@@]1(C)CC[C@@H](O)CC1C[C@H]3O ; [I-]]

N-[3-(dimethylamino)ethyl] cholanamide (21) (0.5 g, 1 mmol) was dissolved in DCM (10 mL) along with 1-iodohexane (0.7 mL, 2 mmol) and methanol (1 mL). The reaction was left for 3 days where a precipitate formed. The product was collected by filtration, washed with chloroform (20 mL) and dried at room temperature under vacuum. The product was a white solid.

Yield=0.45 g (91%)

Melting point: 104.2-104.5° C.

$^1$H NMR (Methanol-d$_4$) δ ppm: 0.68 (s, 3H, Me-18) 0.90 (d, J=5.6 Hz, 6H) 1.01 (d, J=5.6 Hz, 3H, Me-21) 1.0-2.43 (m, steroid structure) 1.15 (td, J=7.0, 0.8 Hz) 3.04 (s, 6H, CH$_2$) 3.47 (m, 1H, 3CH) 3.77 (s, 1H, 7CH) 3.92 (s, 1H, 12CH)

$^{13}$C NMR (DMSO) δ ppm: 172.86 (C=O), 70.96 (C12), 70.37 (C3), 66.20 (C7), 62.99, 60.98, 50.12, (45.98, 35.46, 35.13, 30.05, 29.48, 28.54, 27.26, 26.20 steroid ring), 45.68 (CH$_3$), 34.34 (CH$_2$), 30.65 (CH$_2$), 31.55 (CH$_2$), 25.40, 22.59 (C19), 21.87 (CH$_2$), 21.59, 17.10 (C21), 13.81 (CH$_3$), 12.32 (C18), 9.10 (CH$_2$).

MS (+APCI) m/z=Found 563.4771; calculated for $C_{34}H_{63}N_2O_4$ 563.4782; −2.0 ppm IR (KBr) ν=3393, 3238, 3056, 2925, 2853, 1703, 1651 (C=O), 1606 cm$^{-1}$ Synthesis of
3-cholanamidoethyl-allyl-dimethyl-ammonium bromide (42)

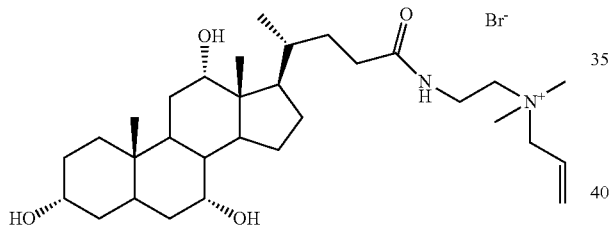

N-[3-(dimethylamino)ethyl] cholanamide (21) (0.5 g, 1 mmol) was dissolved in DCM (10 mL) along with allyl bromide (0.4 mL, 3.3 mmol) and methanol (1 mL). The reaction was left for 12 hours before solvent was removed using a rotary evaporator. The product was purified by washing with diethyl ether was collected by filtration and dried at room temperature under vacuum. The product was a white solid.

Yield=0.129 g (26%)

Melting point: 119.1-120.3° C.

$^1$H NMR (CDCl$_3$) δ ppm: 0.68 (s, 3H, Me-18) 0.89 (s, 3H, Me-19) 0.85-1.61 (m, 29H) 1.00 (d, 3H, Me-21) 1.0-2.43 (m, steroid structure) 3.04 3.76 (s, 1H, CH-3) 3.87-4.13 (m, 6H) 5.61-5.76 (m, 3H) 5.93-6.17 (m, 2H), 7.88 (s, 1H, NH)

$^{13}$C NMR (DMSO) δ ppm: 172.88 (C=O), 127.60 (C=C), 125.76 (C=C), 70.96 (C12), 70.37 (C3), 66.20 (C7), 65.11, 61.12, 49.73, (45.97, 45.68, 35.26, 34.35, 28.53, 27.29, 26.20 steroid ring), 31.55 (CH$_2$—Br), 25.04 (CH$_2$), 22.56 (C19), 17.11 (C21), 12.31 (C18).

MS (+APCI) m/z=Found 519.4146; calculated for $C_{31}H_5N_2O_4$ 519.4156; −2.0 ppm IR (KBr) ν=3362, 2929, 2862, 1700, 1645 (C=O), 1536 cm$^{-1}$ Synthesis of N-[2-(1-methylpyrrolidin-1-ium-1-yl) ethyl]cholanamide iodide (43)

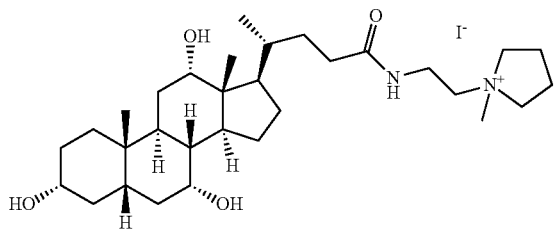

N-(2-pyrrolidin-1-ylethyl)cholanamide (10) (0.5 g, 1 mmol) was dissolved in DCM (10 mL) along with of methyl iodide (1.4 mL, 10 mmol). The reaction was left for 60 hours where the product precipitated out. It was then collected by filtration, washed with chloroform (20 mL) and dried at room temperature under vacuum. The product was a white solid.

Melting point: 140.7-141-4° C.

$^1$H NMR (DMSO) δ ppm: 0.58 (s, 3H, Me-18) 0.81 (s, 3H, Me-19) 0.93 (d, J=5.8 Hz, 3H, Me-21) 1.0-2.43 (m, steroid structure) 2.23 (s) 2.55 2.64 3.44 (1H, CH-3OH) 3.84 (s, 1H, CH-7OH) 3.96 (s, 1H, CH-12OH) 6.40 (s, 1H, NH)

$^{13}$C NMR (DMSO) δ: 173.30 (C=O), 70.96 (C12), 70.37 (C3), 66.19 (C7), 63.86 (CH$_2$), 61.67 (CH$_2$ ring), 47.44, (45.98, 45.68, 41.46, 35.09, 34.34, 33.58, 32.25, 31.40, 28.54, 27.26, 26.20 steroid ring), 41.39 (CH$_2$), 22.76 (CH$_2$ ring), 22.59 (C19), 20.91, 17.04 (C21), 12.31 (C18).

MS (+APCI) m/z=Found 519.4152; calculated for $C_{31}H_{55}N_2O$ 4519.4156; −0.8 ppm IR (KBr) ν=3390, 3274, 2922, 2862, 1651 (C=O), 1533, 1460 cm$^{-1}$ Synthesis of N-[2-(1-ethylpyrrolidin-1-ium-1-yl) ethyl]cholanamide iodide (44)

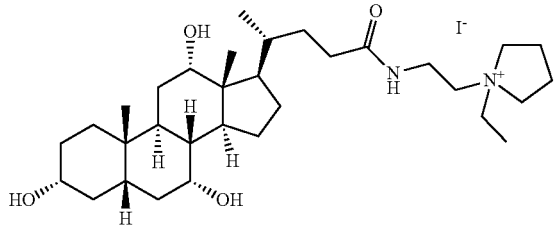

N-(2-pyrrolidin-1-ylethyl)cholanamide (10) (0.5 g, 1 mmol) was dissolved in DCM (10 mL) along with of ethyl iodide (0.4 mL, 10 mmol). The reaction was left for 60 hours where the product precipitated out. It was collected by filtration, washed with chloroform and dried at room temperature under vacuum. The product was a yellow solid.

Melting point: 120.7-121.7° C.

$^1$H NMR (DMSO) δ ppm: 0.57 (s, 3H, Me-18) 0.80 (s, 3H, Me-19) 0.92 (d, J=6.2 Hz, 3H, Me-21) 1.0-2.43 (m, steroid structure) 2.23 (d, J=12.1 Hz) 2.55 2.64 3.44 (1H, CH-3OH) 3.60 (s, 1H, CH-7OH) 3.77 (s, 1H, CH-12OH) 5.75 8.08 (s, 1H, NH)

Carbon N/A

MS (+APCI) m/z=Found 533.4302; calculated for $C_{32}H_{57}N_2O_4$ 533.4313; −2.0 ppm IR (KBr) ν=3378, 2929, 2862, 2361, 2158, 2018, 1645 (C=O), 1527 cm$^{-1}$ Synthesis of N-[2-(1-propylpyrrolidin-1-ium-1-yl)ethyl]cholanamide;iodide (45)

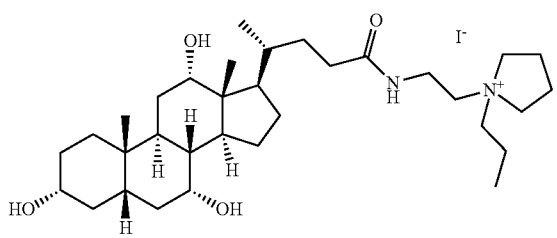

N-(2-pyrrolidin-1-ylethyl)cholanamide (10) (0.5 g, 1 mmol) was dissolved in DCM (15 mL) along with of 1-iodopropane (3 mL, 10 mmol). The reaction was left for 12 hours where the product precipitated out. It was collected by filtration, washed with chloroform and dried. The product was a yellow solid.

Yield=0.947 g

Melting point: 203.8-204.1° C.

$^1$H NMR (D$_2$O) δ ppm: 0.68 (s, 3H, Me-18) 0.80 (s, 3H, Me-19) 0.91 (d, 3H, Me-21) 1.0-2.43 (m, steroid structure) 3.18 (m) 3.49 (ddt, J=40.0, 13.4, 6.6 Hz, 8H, CH-3OH, CH$_2$) 3.87 (s, 1H, CH-7OH) 4.03 (s, 1H, CH-12OH) 7.64 (s, 1H, NH)

Carbon=N/A

MS (+APCI) m/z=Found 547.4463; calculated for C$_{33}$H$_{59}$N$_2$O$_4$ 547.4469; −1.2 ppm IR (KBr) ν=3566, 3353, 3217, 2913, 2856, 2246, 2121, 1642, 1527 cm$^{-1}$ Synthesis of N-[2-(1-hexylylpyrrolidin-1-ium-1-yl)ethyl]cholanamide iodide (48)

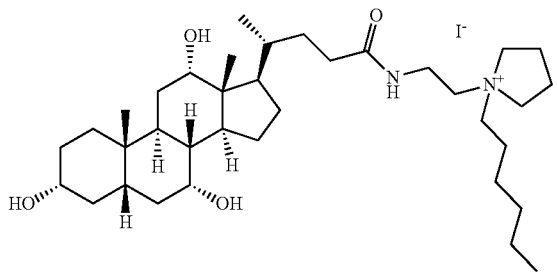

N-(2-pyrrolidin-1-ylethyl)cholanamide (10) (0.5 g, 1 mmol) was dissolved in DCM (15 mL) along with of 1-iodopentane (2 mL, 10 mmol). The reaction was left for 96 hours where the product precipitated out. It was collected by filtration, washed with chloroform (15 mL) and dried at room temperature under vacuum. The product was a yellow solid.

Yield=0.49 g (98%)

$^1$H NMR (CDCl$_3$) δ ppm: 0.58 (s, 3H, Me-18) 0.81 (s, 3H, Me-19) 0.91 (d, 3H, Me-21) 1.0-2.43 (m, steroid structure) 2.50 (p, J=1.8 HZ, 4H) 3.33 (m) 3.49 (m, 8H, CH-3OH, CH$_2$) 3.77 (s, 1H, CH-7OH) 4.32 (s, 1H, CH-12OH) 7.72 (s, 1H, NH), 8.08, 8.31

$^{13}$C NMR (DMSO) δ 173.38 (C=O), 70.96 (C12), 70.37 (C3), 70.30, 66.19 (C7), 62.48, 58.76, 56.74 (CH$_2$ ring), (45.95, 45.69, 40.48, 40.15, 39.81, 39.48, 39.15, 38.81, 38.48, 35.09, 34.34, 32.22, 31.36, 30.71, 28.54, 27.25, 26.21 steroid ring), 25.43 (CH$_2$ ring), 22.59 (C19), 21.91 (CH$_2$), 21.15, 17.04 (C21), 13.82 (CH$_3$), 12.29 (C18).

MS (+APCI) m/z=589.4926

IR (KBr) ν=3466, 3362, 3186, 3044, 2953, 2922, 1706, 1660, 1624 (C=O), 1530 cm$^{-1}$

Synthesis of N-[2-(1-allylpyrrolidin-1-ium-1-yl)ethyl]cholanamide bromide (49)

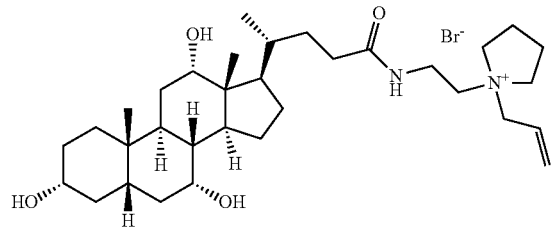

N-(2-pyrrolidin-1-ylethyl)cholanamide (10) (0.5 g, 1 mmol) was dissolved in chloroform (20 mL) along with allylbromide (1.2 mL, 10 mmol). The reaction was left for 96 hours where the product precipitated out. It was collected by filtration, washed with chloroform (20 mL) and dried at room temperature under vacuum. The product was a white solid.

Yield=0.59 g (60%)

Melting point: 186.5-186.9° C.

$^1$H NMR (DMSO) δ ppm: 0.59 (s, 3H, Me-18) 0.88 (s, 3H, Me-19) 0.94 (d, 3H, Me-21) 1.0-2.43 (m, steroid structure) 2.07 (m) 2.23 (d, J=12.1 Hz, CH$_2$) 2.55 2.64 3.52 (m, 3H, CH-3OH+CH$_2$) 3.61 (s, 1H, CH-7OH) 3.79 (s, 1H, CH-12OH) 4.00 (d, 2H, CH$_2$ allyl bromide) 5.66 (t, 2H, allyl bromide) 6.08 (m, 1H, allyl bromide) 8.13 (t, 1H, NH) 8.32 (s, 1H)

$^{13}$C NMR (DMSO) δ ppm: 173.37 (C=O), 127.23 (C=C), 126.28 (C=C), 79.17, 70.94 (C12), 70.36 (C3), 66.18 (C3), 61.74, 60.54, 57.71 (CH$_2$), (45.94, 45.68, 40.48, 40.15, 40.07, 39.82, 39.73, 39.48, 39.15, 38.81, 38.48, 34.34, 33.11, 31.39, 30.35, 28.54, 28.53, 27.29, 26.20 steroid ring), 32.18 (CH$_2$), 22.60 (C19), 21.16, 17.03 (C21), 12.30 (C18).

MS (+APCI) m/z=Found 545.4306; calculated for C$_{33}$H$_{57}$N$_2$O$_4$ 545.4313; −1.3 ppm IR (KBr) ν=3472, 3365, 3211, 3050, 2922, 2859, 2458, 2042, 1630 (C=O), 1542 cm$^{-1}$ Synthesis of N-[2-(1-benzylpyrrolidin-1-ium-1-yl)ethyl]cholanamide bromide (50)

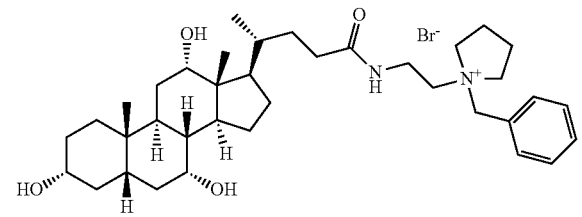

N-(2-pyrrolidin-1-ylethyl)cholanamide (10) (0.5 g, 1 mmol) was dissolved in DCM (15 mL0 along with benzyl bromide (1.2 mL, 10 mmol). The reaction was left for 48 hours where the product precipitated out. It was collected by filtration, washed with chloroform (15 mL) and dried at room temperature under vacuum. The product was a yellow solid.

Yield=0.301 g (30%)

Melting point: 165.7-165.9° C.

$^1$H NMR (D$_2$O) δ ppm: 0.56 (s, 3H, Me-18) 0.87 (s, 3H, Me-19) 0.92 (d, 3H, Me-21) 1.0-2.43 (m, steroid structure) 2.19 (s) 2.23 (d, J=12.1 Hz, CH$_2$) 3.37-3.68 (m, 6H, CH-3OH+CH$_2$) 3.75 (s, 1H, CH-7OH) 3.98 (s, 1H, CH-12OH) 7.38 (s, 1H, NH) 7.54 (m, aromatic)

$^{13}$C NMR (DMSO) δ ppm: 173.43 (C=O), (132.61, 129.04, 128.41 aromatic ring), 60.89 (CH$_2$), 60.86 (CH$_2$), (45.69, 35.25, 35.10, 34.94, 34.67, 34.34 steroid ring), 22.59 (C19), 20.86, 17.03 (C21), 12.28 (C18).

MS (+APCI) m/z=595.4461

IR (KBr) ν=3368, 3053, 2922, 2862, 2361, 1788, 1706, 1648 (C=O), 1536 cm$^{-1}$

Synthesis of N-[2-[1-(3-phenylpropyl)pyrrolidin-1-ium-1-yl]ethyl]cholanamide bromide (51)

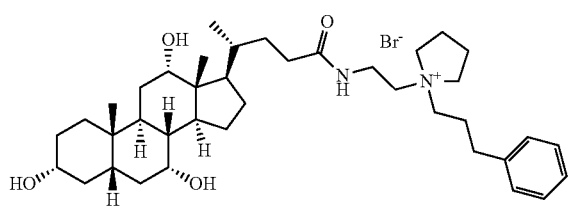

N-(2-pyrrolidin-1-ylethyl)cholanamide (10) (0.5 g, 1 mmol) was dissolved in DCM (15 mL) along with 1-bromo-3-phenylpropane (2 mL, 10 mmol). The reaction was left for 12 hours where the product precipitated out. It was collected by filtration, washed with chloroform (10 mL) and dried at room temperature under vacuum. The product was a yellow solid.

Yield=0.986 g (98%)

Melting point: 140.8-141.3° C.

$^1$H NMR (DMSO) δ ppm: 0.57 (s, 3H, Me-18) 0.77 (s, 3H, Me-19) 0.92 (d, J=5.9 Hz, 3H, Me-21) 1.0-2.43 (m, steroid structure) 2.68, (dt, J=10.9, 7.4 Hz, 2H, CH$_2$) 3.16-3.58 (m, 9H, CH-3OH, CH$_2$) 3.60 (s, 1H, CH-7OH) 3.77 (s, 1H, CH-12OH) 7.12-7.36 (m, 4H, aromatic) 8.11 (t, J=5.5 Hz, 1H, NH)

$^{13}$C NMR (DMSO) δ ppm: 173.32 (C=O), (140.52, 128.37, 128.37, 128.33, 125.98 aromatic ring), 79.15, 70.97 (C12), 70.38 (C3), 66.20 (C7), 63.84 (CH$_2$), 61.68 (CH$_2$), 47.42, (45.98, 45.69, 45.68, 40.48, 40.14, 39.81, 39.48, 39.14, 38.81, 38.47, 35.10, 34.86, 34.35, 33.85, 33.58, 33.36, 32.25, 31.39, 30.34, 28.53, 27.27, 26.20 steroid ring), 34.34 (CH$_2$), 22.59 (C19), 20.90, 17.04 (C21), 12.30 (C18).

MS (+APCI) m/z=Found 519.4150; expected 623.478 (MI− CH$_2$CH$_2$C$_6$H$_6$)

IR (KBr) ν=3387, 3256, 3068, 3026, 2929, 2868, 1651, 1624 (C=O), 1533 cm$^{-1}$

Synthesis of [1-(2-cholanamidoethyl)pyrrolidin-1-ium-1-yl]methyl 2,2-dimethylpropanoate chloride (52)

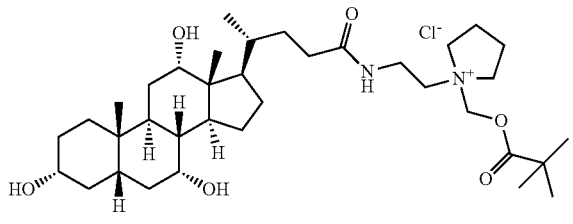

N-(2-pyrrolidin-1-ylethyl)cholanamide (10) (0.5 g, 1 mmol) was dissolved in DCM (10 mL) along with chloromethyl pivalate (1.4 mL, 10 mmol). The reaction was left for 72 hours where the product precipitated out. It was collected by filtration, washed with chloroform and (15 mL) dried at room temperature under vacuum. The product was a yellow solid.

Yield=0.335 g (34%)

Melting point: 121.2-121.8° C.

$^1$H NMR (DMSO) δ ppm: 0.68 (s 3H Me-18) 0.80 (s 3H Me-19) 0.91 (d 3H Me-21) 1.0-2.439 (m steroid structure) 3.38 (t J=9.1 Hz 1H CH-3) 3.87 (s 1H CH-7OH) 4.03 (s 1H CH-12OH) 8.66 (s 1H NH) 11.39 (s 1H)

$^{13}$C NMR (DMSO) δ 206.43, 179.27, 175.20 (C=O), 173.36, 173.14, 77.70, 70.93 (C12), 70.37 (C3), 69.58, 66.19 (C7), 60.88, 57.80, 53.07 (CH$_2$), 52.88 (CH$_2$ ring), (45.71, 37.66, 35.16, 34.85, 34.34, 33.32, 33.29, 32.16, 31.29, 30.65, 30.65, 28.50, 26.97, 26.97, 26.88, 26.42, 26.31, 26.20 steroid ring), 22.57 (C19), 21.81 (CH$_2$ ring), 17.07 (C21), 12.28 (C18).

MS (+APCI) m/z=619.4647

IR (KBr) ν=3368, 2929, 2874, 2607, 2476, 2249, 2118, 1754, 1709, 1651 (C=O), 1539 cm$^{-1}$

Synthesis of N-(1-methyl-1-phenyl-piperidin-1-ium-4-yl)cholanamide iodide (53)

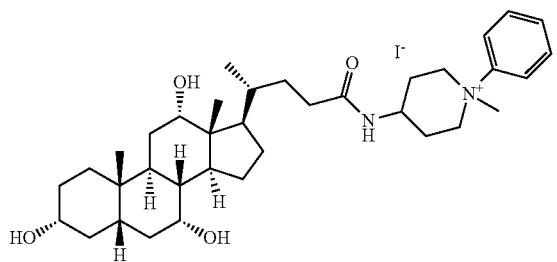

N-(1-phenyl-4-piperidyl) cholanamide (13) (0.5 g, 1 mmol) was dissolved in DCM (15 mL) along with methyl iodide (1.4 mL, 10 mmol). The reaction was left for 72 hours where the product precipitated out. It was collected by filtration, washed with DCM (20 mL) and dried at room temperature under vacuum. The product was a yellow solid.

Yield=0.7 g (70%)

Melting point: 165.8-166.7° C.

$^1$H NMR (D$_2$O) δ ppm: 0.58 (s, 3H, Me-18) 0.79 (s, 3H, Me-19) 0.92 (d, 3H, Me-21) 1.0-2.43 (m, steroid structure) 2.82-3.18 (m, 7H) 3.43 (m, 1H, CH-3) 3.60 (s, 1H, CH-7

3.78 (s, 1H, CH-12) 4.38-4.54 (m, 2H, CH$_2$) 4.60 (m, 2H, CH$_2$) 7.53 (m, 5H, aromatic) 7.79-7.90 (m, 1H, NH)

$^{13}$C NMR (DMSO) δ ppm: 172.24 (C=O), (133.08, 128.86, 127.54 aromatic ring), 35.10, 34.35, 22.60 (C19), 17.12 (C21), 12.31 (C18).

MS (+APCI) m/z=Found 595.4464; calculated for C$_{36}$H$_{57}$N$_2$O$_4$ 595.4469; 0.84 ppm IR (KBr) ν=3396, 2925, 2862, 2355, 1648 (C=O), 1533 cm$^{-1}$ Synthesis of N-(1-propyl-1-phenyl-piperidin-1-ium-4-yl)cholanamide iodide (54)

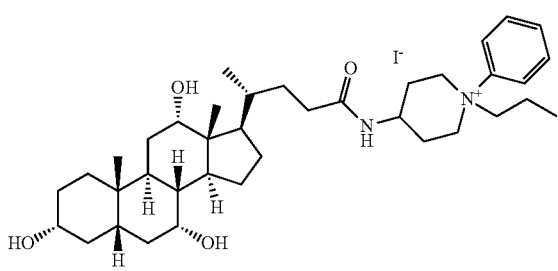

N-(1-phenyl-4-piperidyl) cholanamide (13) (0.5 g, 1 mmol) was dissolved in DCM (15 mL) along with methyl iodide (1.5 mL, 10 mmol). The reaction was left for 72 hours where the product precipitated out. It was collected by filtration, washed with DCM (15 mL) and dried at room temperature under vacuum. The product was a yellow solid.

Yield=0.7 g (70%)

Melting point: 113-113.8° C.

$^1$H NMR (DMSO) δ ppm: 0.58 (d J=4.1 Hz 3H Me-18) 0.80 (s 3H Me-19) 0.91 (m 9H Me-21+2CH$_3$) 1.0-2.439 (m steroid structure) 2.08 (s CH$_2$) 3.01-3.33 (m 9H CH$_2$) 3.61 (s 1H CH-7OH) 3.78 (s 1H CH-12OH) 3.92-4.11 (m 2H) 4.60 (d J=10.3 Hz 1H) 7.42-7.62 (m 6H aromatic ring)

Carbon=N/A

MS (+APCI) m/z=Found 651.5086; expected 609.4625 (MI+ 52)

IR (KBr) ν=3393, 2932, 2862, 2361, 2155, 2018, 1642 (C=O), 1533 cm$^{-1}$

Synthesis of N-(1-hexyl-1-phenyl-piperidin-1-ium-4-yl)cholanamide iodide (57)

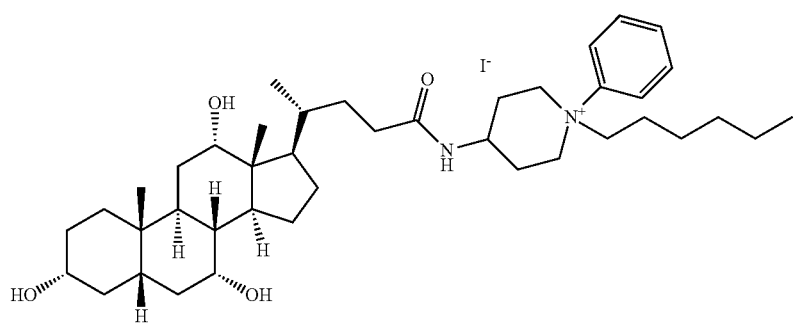

N-(1-phenyl-4-piperidyl) cholanamide (13)(0.5 g, 1 mmol) was dissolved in DCM (15 mL) along with 1-iodohexane (1.5 mL, 10 mmol). The reaction was left for 120 hours where the product did not precipitate. The solvent was removed under vacuum and the product was sonicated then washed with diethyl ether (10 mL). The product was dried at room temperature under vacuum and it a yellow solid.

Yield=0.55 g (55%)

Melting point: 126.4-127.8° C.

$^1$H NMR (CDCl$_3$) δ ppm: 0.66 (s, 3H, Me-18) 0.89 (s, 3H, Me-19) 0.79 (d, Me-21) 1.0-2.43 (m, steroid structure) 2.04 (s) 2.83 (m) 3.47 (m, 1H, CH-3) 3.56 (m, CH$_2$) 3.81 (s, 1H, CH-7) 3.94 (s, 1H, CH-12) 6.06 (d, J=7.8 Hz, 1H, NH) 7.32 (q, J=4.3, 3.7 Hz, 6H, aromatic)

$^{13}$C NMR (DMSO) δ ppm: 206.44, 171.82 (C=O), (128.73, 128.16, 126.95 aromatic ring), 70.97 (C12), 70.46 (C3), 66.20 (C7), 51.90 (CH$_2$), (46.11, 45.69, 40.49, 40.16, 35.30, 34.86, 34.35, 34.35, 32.56, 31.72, 30.66, 29.68, 28.53, 27.30, 26.18 steroid ring), 22.59 (C19), 17.11 (C21), 12.31 (C18).

MS (+APCI) m/z=Found 665.5257; calculated for C$_{41}$H$_{67}$N$_2$O$_4$ 665.5252; 0.77 ppm IR (KBr) ν=3372, 3296, 3056, 3032, 2932, 2862, 2364, 1642 (C=O), 1530 cm$^{-1}$ Synthesis of N-(1-benzyl-1-phenyl-piperidin-1-ium-4-yl)cholanamide (58)

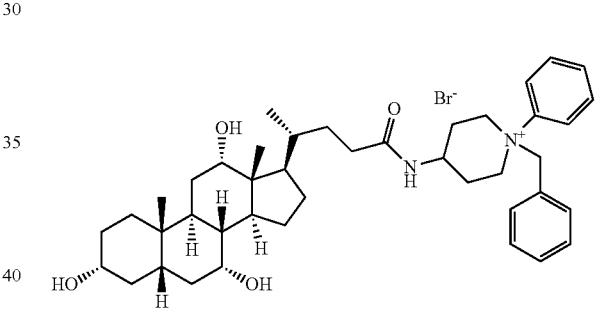

N-(1-phenyl-4-piperidyl) cholanamide (13) (0.5 g, 1 mmol) was dissolved in DCM (15 mL) along with benzyl bromide (1.5 mL, 10 mmol). The reaction was left for 12 days where the product precipitated. The product washed with diethyl ether (10 mL). The product was dried at room temperature under vacuum and it a peach solid.

Yield=0.1839 g (18%)

Melting point: 150.3-150.9° C.

$^1$H NMR (MeOD) δ ppm: 0.68 (s, 3H, Me-18) 0.90 (s, 3H, Me-19) 0.98 (d, 3H, Me-21) 1.0-2.43 (m, steroid structure) 3.68 (m, 1H, CH-3) 3.78 (s, 1H, CH-7) 3.92 (s, 1H, CH-12) 4.49 (s, 2H, CH$_2$) 7.19-7.67 (m, 11H, aromatics)

$^{13}$C NMR (DMSO) δ ppm: (133.56, 133.08, 130.33, 129.23, 127.46, 127.12, 126.37 aromatic ring), 70.96 (C12), 45.69, 34.35 (CH$_2$), 27.31, 24.50, 22.59 (C19), 17.04 (C21), 12.30 (C18), 5.85, 1.58.

MS (+APCI) m/z=Found 671.4770; expected 657.4625 (MI+CH$_3$)

IR (KBr) ν=3411, 3329, 3062, 2929, 2859, 2671, 2355, 1654 (C=O), 1536, 1493 cm$^{-1}$

Synthesis of (4-cholanamido-1-phenyl-piperidin-1-ium-1-yl)methyl 2,2-dimethylpropanoate chloride (59)

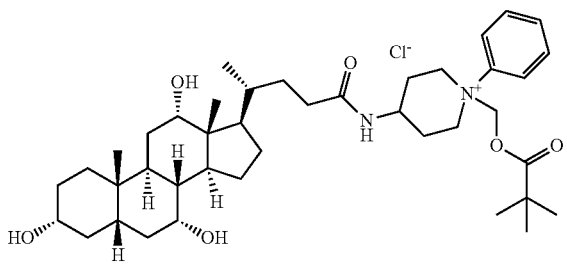

N-(1-phenyl-4-piperidyl) cholanamide (13) (0.5 g, 1 mmol) was dissolved in chloroform (15 mL) along with of chloromethyl pivalate (1.4 mL, 10 mmol). The reaction was left for 12 days where the product did not precipitate. The solvent was taken off under vacuum and the product sonicated and washed with diethyl ether (10 mL). The product was dried at room temperature under vacuum and it a yellow solid.

Yield=0.5215 g (52%)

Melting point: 135.9-137° C.

$^1$H NMR (MeOD) δ ppm: 0.70 (s, 3H, Me-18) 0.92 (s, 3H, Me-19) 1.02 (d, 3H, Me-21) 1.0-2.439 (m, steroid structure) 2.99 (d, J=11.4 Hz, 1H) 3.78 (s, 1H, CH-7) 3.97 (s, 1H, CH-12) 5.75 (s, 2H, O—CH$_2$—Cl) 7.24-7.45 (m, 2H, aromatic) 7.55 (m, 1H, NH)

$^{13}$C NMR (DMSO) δ ppm: 206.44 (C=O), 175.60 (C=O), 128.69, 69.59 (CH$_2$),) 45.69, 35.12, 34.35, 30.66, 26.97, 26.32 steroid ring), 22.59 (C19), 17.11 (C21), 12.30 (C18).

MS (+APCI) m/z=Found 695.4994; calculated for C$_{41}$H$_{65}$N$_2$O 6695.4993; 0.143 ppm IR (KBr) ν=3365, 3065, 2935, 2865, 2631, 2525, 2361, 1751, 1642 (C=O), 1542 cm$^{-1}$ Synthesis of N-[1-phenyl-1-(3-phenylpropyl)piperidin-1-ium-4-yl]cholanamide bromide (60)

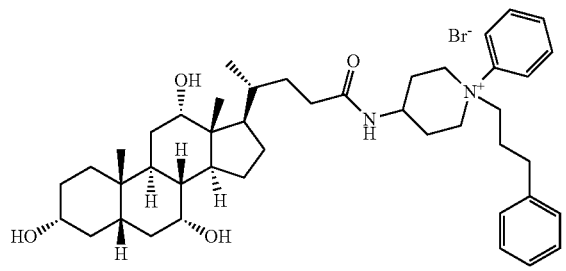

N-(1-phenyl-4-piperidyl) cholanamide (13) (0.5 g, 1 mmol) was dissolved in chloroform (15 mL) along with 1-bromo-3-phenylpropane (1.3 mL, 10 mmol). The reaction was left for 12 days where the product did not precipitate. The solvent was taken off under vacuum and the product sonicated and washed with diethyl ether (10 mL). The product was dried at room temperature under vacuum and it a yellow solid.

Yield=0.79 g (80%)

Melting point: 126.1-126.7° C.

$^1$H NMR (MeOD) δ ppm: 0.69 (s, 3H, Me-18) 0.91 (s, 3H, Me-19) 0.98 (d, 3H, Me-21) 1.0-2.43 (m, steroid structure) 3.43 (m) 3.66 (m, 1H, CH-3) 3.79 (s, 1H, CH-7) 3.94 (s, 1H, CH-12) 7.09-7.41 (m, 7H, aromatic)

$^{13}$C NMR (DMSO) δ ppm: (140.52, 128.85, 128.43, 128.37, 128.33, 125.98 aromatic ring), 70.99 C12), 70.38 (C3), 66.20 (C7), (45.95, 45.69, 45.69, 40.49, 40.15, 35.27, 34.89, 33.36, 31.62, 30.38, 28.52, 27.31, 26.19 steroid ring), 34.61 (CH$_2$), 34.36 (CH$_2$), 33.86 (CH$_2$), 22.59 (C19), 17.12 (C21), 12.31 (C18).

MS (+APCI) m/z=Found 699.5087; calculated for C$_{44}$H$_{65}$N$_2$O$_4$ 695.5095; 1.143 ppm IR (KBr) ν=3375, 3023, 2932, 2859, 1642 (C=O), 1536 cm$^{-1}$ Synthesis of N-(1-allyl-1-phenyl-piperidin-1-ium-4-yl)cholanamide bromide (61)

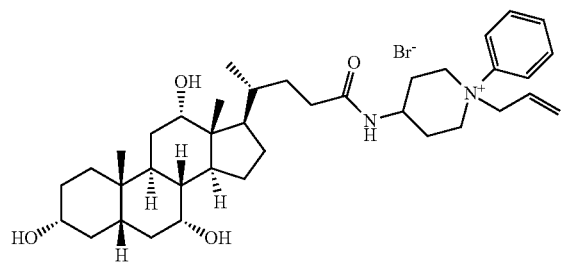

N-(1-phenyl-4-piperidyl) cholanamide (13) (0.5 g, 1 mmol) was dissolved in DCM (15 mL) along with allyl bromide (1.2 mL, 10 mmol). The reaction was left for 4 days where the product precipitated then washed with DCM (25 mL). The product was dried at room temperature under vacuum and to give an orange solid.

Yield=0.242 g (24%)

Melting point: 161.4-161.7° C.

¹H NMR (CDCl₃) δ ppm: 0.58 (d, J=3.6 Hz, 2H, Me-18) 0.81 (s, 2H, Me-19) 0.93 (d, J=5.8 Hz 3H, Me-21) 1.0-2.43 (m steroid structure) 3.18, 3.61 (s, 1H, CH-3), 3.78 (s 1H CH-7), 3.95 (dd, J=16.7, 9.8 Hz 1H CH-12) 4.08 (s) 4.31 (s 2HCH₂) 4.55-4.68 (m C=CH) 5.61-5.83 (m C=CH) 7.42-7.62 (m 6H aromatic ring)

¹³C NMR (DMSO) δ ppm: 187.15 (C=O), 133.09 (C=C), (131.49, 130.30, 128.97, 127.16 aromatic ring), 92.56 (C=C), 70.96 (C12), 70.37 (C3), 66.19 (C7), 55.64 (CH₂), (46.01, 41.48, 40.50, 40.16, 39.83, 39.49, 39.15, 38.82, 38.74, 38.50, 37.34, 35.27, 30.66, 28.56 steroid ring), 22.59 (C19), 17.13 (C21), 12.30 (C18).

MS (+APCI) m/z=Found 621.4620; calculated for C₃₈H₅₉N₂O₄ 621.4626; 0.96 ppm

IR (KBr) ν=3378, 3056, 2935, 2856, 2552, 2358, 1639 (C=O), 1533 cm⁻¹

Synthesis of 3α, 7, 12α-triacrylate cholic acid methyl ester (62)

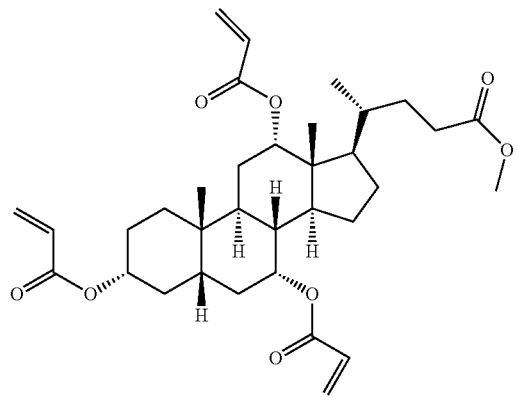

Methyl cholate (4.22 g, 10 mmol) was dissolved in dry chloroform (30 mL). Triethylamine (2.23 mL, 16 mmol) was added and the flask was cooled to ice temperature. Acryloyl chloride (1.3 mL, 15 mmol) in chloroform (10 mL) was dripped in over 30 minutes. The mixture was protected from the light and left at room temperature overnight. More acryloyl chloride (1.3 mL, 15 mmol) in dry chloroform (10 mL) was dripped in over 30 minutes and the reaction was left for 6 hours at room temperature. The flask was maintained at −20° C. for 5 days. More acryoyl chloride (1.5 mL) was added. The reaction was left for 24 hours at room temperature. The solvent was removed using a rotary evaporator (the temperature was set to 30° C.) to produce a white solid. Ethyl acetate (50 mL) was added and the solid (salt) was collected by filtration. The ethyl acetate was removed on the rotary evaporator to leave a yellow oil. Flask column chromatography using 95% DCM/5% ethyl acetate was used to purify the product, increasing to 9/1 ratio then 3/1 ratio. The solvents were removed by rotary evaporation before the product was dried at room temperature under vacuum.

Yield=0.2176 g (5%)

¹H NMR (CDCl₃) δ ppm: 0.75 (s 2H Me-18) 0.83 (s 2H Me-19) 0.94 (d 3H Me-21) 1-2.43 (steroid structure) 2.67-2.91 (m 2H) 3.60-3.86 (m 1H) 4.63 (m 1H CH-3) 5.03 (s 1H CH-7) 5.19 (s 1H CH-12) 5.72-5.97 (m 2H C=CH) 5.99-6.52 (m, 3H C=CH)

¹³C NMR (CDCl₃) δ ppm: 174.48 (C=O), 169.70 (C=O), 169.38 (C=O), 169.20 (C=O), 165.67 (C=O excess), 165.46 (C=O excess), 165.38 (C=O excess), 165.29, 165.23, 136.42 (C=C), 130.55 (C=C), 130.42, 130.26, 130.18, 129.12, 129.00, 75.43, 74.62, 74.08, 73.92, 70.94 (C12), 70.85 (C3), 51.48, (47.44, 45.23, 45.12, 43.40, 43.32, 43.22, 40.84, 40.74, 39.32, 39.20, 39.14, 38.22, 38.00, 37.87, 34.75, 34.62, 34.55, 34.43, 34.35, 31.29, 30.91, 30.85, 30.74, 28.82, 28.60, 27.17, 26.74, 26.65 steroid ring), 25.46, 25.16, 22.84, 22.5 (C19), 22.34, 17.53 (C21), 17.45, 12.18 (C18), 12.08.

MS (+APCI) m/z=Found 602.1935; expected 584.3349 (MI+CH₃+3H)

IR (KBr) ν=2947, 271, 1715, 1633 (C=O), 1612, 1469 cm⁻¹

Synthesis of 3α,12α diacroylate-7αhydroxycholic acid (63)

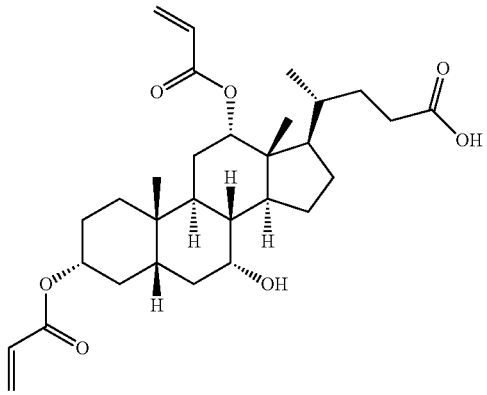

This product was collected by column chromatography of the previous product (3α,7α,12α-triacrylate cholic acid methyl ester).

Yield=0.7744 g (18%)

¹H NMR (CDCl₃) δ ppm: 0.68 (s 2H Me-18) 0.84 (s 2H Me-19) 0.95 (d 3H Me-21) 1-2.43 (Steroid structure) 2.66-2.93 (m 1H) 3.61-3.93 (s 3H CH₃) 4.12 (q, J=7.1 Hz, 1H ethyl acetate), 4.64 (tt, J=10.7, 6.5 Hz, 1H CH-3) 4.99 (s 1H CH-7) 5.18 (s 1H CH-12) 5.34 (m 1H) 5.70-5.93 (m 1H C=CH) 5.98-6.52 (m 2H C=CH)

¹³C NMR (CDCl₃) δ ppm: 174.55 (C=O), (169.68, 169.57, 165.78, 165.71, 165.57, 163.18 C=O, including excess acyloyl chloride), (130.66, 130.54, 130.30, 130.19, 130.08, 129.12, 129.00, 128.87 C=C, including excess acyloyl chloride), 75.63, 74.40, 74.28, 74.17, 72.57, 71.79, 71.02 (C12), 67.93 (C7), 60.36, 51.46, 47.46, 47.11, (46.56, 45.20, 45.06, 43.55, 43.40, 42.08, 42.02, 41.18, 41.12, 40.90, 40.84, 39.23, 38.23, 38.10, 35.23, 35.16, 34.96, 34.73, 34.61, 34.52, 34.34, 31.31, 30.98, 30.81, 28.60, 28.17, 28.10, 27.69, 27.51, 27.24, 26.64 steroid ring), 25.51, 25.36, 22.90, 22.53 (C19), 17.41 (C21), 17.32, 12.50, 12.26 (C18), 12.19.

MS (+APCI) m/z=Found 548.1638; expected 531.3322 (MI+CH₃+2H)

IR (KBr) ν=35 26 2944, 2871, 1715, 1639 (C=O), 1612, 1469 cm-1

Synthesis of 3α acetate-7α,12α dihydroxy cholic acid (64)

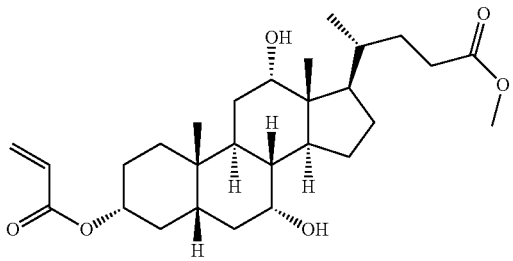

This product was collected by column chromatography of the product 3α,7α,12α-triacrylate cholic acid methyl ester. Yield=0.0232 g $^1$H NMR (CDCl$_3$) δ ppm: 0.70 (s 3H Me-18) 0.82 (s 3H Me-19) 0.94 (d 3H Me-21) 1-2.43 (steroid structure) 3.67 (s 3H CH$_3$) 3.87 (s 1H CH-7) 4.11 (s 1H CH-12) 5.78 (dd J=10.3, 1.7 Hz, 1H C=CH) 6.07 (dd J=17.3, 10.3 Hz 1H C=CH) 6.37 (dd J=17.3, 1.7 Hz, 1H)

$^{13}$C NMR (CDCl$_3$) δ ppm: 217.85, 216.22, 215.83, 215.45, 214.86, 214.47, 173.94, 73.08, 71.85 (C12), 68.27 (C7), 56.87, (46.52, 45.30, 41.74, 41.49, 40.08, 39.58, 38.83, 35.37, 34.80, 33.50, 33.13, 31.74, 30.41, 29.10, 28.16, 27.62, 26.43, 26.10 steroid ring), 25.01, 23.32, 22.69, 22.51 (C19), 17.57 (C21), 14.17, 12.50 (C18), 11.48.

MS (+APCI) m/z=Found 494.16; expected 476.3138 (MI+CH$_3$+3H)

IR (KBr) ν=3375, 2959, 2932, 2865, 1712, 1630 (C=O), 1618, 1533 cm$^{-1}$

Synthesis of 3α methacrylate 7α,12α dihydroxyl cholic acid methyl ester (65)

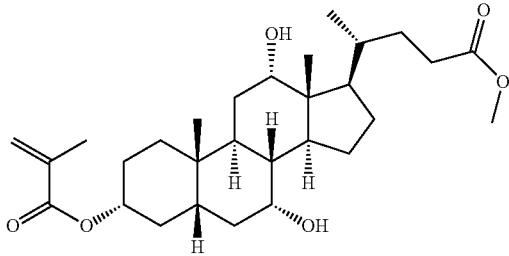

Methyl cholate (4.22 g, 10 mmol) was dissolved in dry chloroform (30 mL). Triethylamine (2.23 mL, 16 mmol) was added and the flask was put on ice. Methacryloyl chloride (1.45 mL, 15 mmol) in chloroform (10 mL) was dripped in over 30 minutes. The mixture was protected from the light and left at room temperature overnight. The solvent was removed using a rotary evaporator (the temperature was set to 30° C.) to produce a white solid. Ethyl acetate (50 mL) was added and the solid (salt) was collected by filtration. The ethyl acetate was removed on the rotary evaporator to leave a white solid. Flask column chromatography using 75% DCM/25% ethyl acetate was used to purify the product. The solvents were removed by rotary evaporation before the product was dried at room temperature under vacuum.

$^1$H NMR (CDCl$_3$) δ ppm: 0.70 (s 3H Me-18) 0.83 (s 3H Me-19) 0.98 (d 3H Me-21) 1-2.43 (steroid structure) 3.77 (s 3H CH$_3$) 3.82 (d, J=26.9 Hz 1H CH-7) 4.10 (s 1H CH-12) 4.63 (tt J=11.2, 4.4 Hz, 1H CH-3) 5.5 (m 1H C=CH) 5.83 (m 1H C=CH) 6.07 (s 1H) 6.25 (s 1H)

$^{13}$C NMR (CDCl$_3$) δ ppm: 218.61, 174.68 (C=O), 167.10 (C=O), 136.92 (C), 124.92 (C=C), 74.54, 72.92 (C12), 68.26 (C7), 51.52, 47.26, (46.57, 42.15, 41.23, 39.57, 35.22, 35.13, 34.90, 34.71, 34.42, 31.05, 30.89, 28.44, 27.42, 26.83, 26.69 steroid ring), 23.14, 22.57 (C19), 18.35 (CH$_3$), 17.37 (C21), 12.57 (C18).

MS (+APCI) m/z=Found 535.3181; expected 476 (MI+CH$_3$CN+H$_2$O)

IR (KBr) ν=3599, 3544, 2971, 2935, 2865, 1733, 1703, 1639 (C=O), 1469 cm$^{-1}$

Synthesis of N-[2-[1-[(4-vinylphenyl)methyl]pyrrolidin-1-ium-1-yl]ethyl]cholanamide chloride (69)

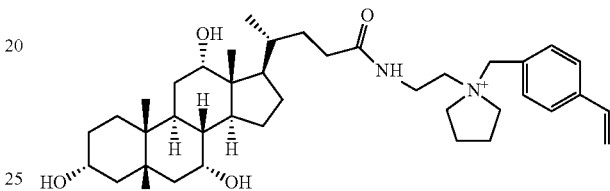

N-(2-pyrrolidin-1-ylethyl) cholanamide (10) (0.35 g, 0.7 mmol) was dissolved in chloroform (10 mL). Vinyl benzyl (0.5 mL, 3.5 mmol) chloride was added. The reaction was protected from the light and left to stir overnight. The reaction was heated under reflux for 24 hours. The solvent was removed under reduced pressure before the product was dried at room temperature under vacuum.

$^1$H NMR (CDCl$_3$) δ ppm: 0.58 (s 3H Me-18) 0.84 (s 3H Me-19) 0.93 (d 3H Me-21) 1-2.43 (steroid ring) 3.11-3.24 (m, 8H 2CH$_2$), 3.60 (m, 1H CH-3), 3.77 (s, 1H CH-7), 3.95 (m, 1H CH-12), 4.35 (d, J=4.0 Hz, 2H CH$_2$), 4.54 (s, 2H CH$_2$), 5.38 (d, J=10.9 Hz, 1H C=CH), 5.96 (d, J=17.6 Hz, 1H C=CH), 6.80 (dd, J=17.7, 11.0 Hz, 1H), 8.23 (d, J=5.2 Hz, 1H NH).

$^{13}$C NMR (DMSO) δ ppm: 173.40 (C=O), (145.12, 138.80, 132.94, 127.83, 126.57, 104.54 aromatic ring), 135.74 (C=C), 116.15 (C=C), 79.52, 78.99, 78.46, 70.94 (C12), 70.39 (C3), 67.05, 66.21 (C7), 61.14, 60.78, 57.11 (CH$_2$), 48.55, (45.95, 45.72, 41.48, 41.38, 40.50, 40.42, 40.17, 35.28, 35.13, 34.86, 34.34, 33.10, 32.23, 31.42, 28.51, 27.30, 26.19 steroid ring), 22.58 (C19), 20.86, 17.05 (C21), 14.56, 12.27 (C18).

MS (+APCI) m/z=621.4614

IR (KBr) ν=3350, 3059, 2932, 2862, 1703, 1651 (C=O), 1533 cm$^{-1}$

Synthesis of 3-acetamidopropyl-dimethyl-[(4-vinylphenyl)methyl]ammonium chloride (70)

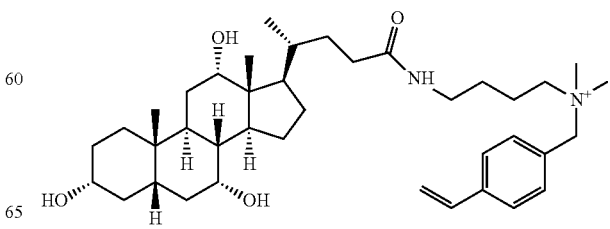

N-[3-dimethylamino) propyl] cholanamide (12) (0.35 g, 0.7 mmol) was dissolved in chloroform (10 mL). Vinyl benzyl chloride (0.5 mL, 3.5 mmol) was added. The reaction was protected from the light and left to stir overnight. The reaction was heated under reflux for 24 hours. The product precipitated out, collected by filtration and washed with petrol 40-60 (30 mL). Product not pure.

$^1$H NMR (CDCl$_3$) δ ppm: 0.65 (s 3H Me-18) 0.87 (s 3H Me-19) 0.95 (d 3H Me-21) 1-2.43 (steroid structure) 3.49 (s, 1H CH-12), 3.69 (d, J=19.8 Hz, 1H CH-7), 3.90 (s, 1H CH-3), 5.38 (dd, J=11.0, 5.9 Hz, 1H CH=CH), 5.83 (dd, J=17.7, 4.8 Hz, 1H CH=CH), 6.71 (dd, J=17.6, 10.9 Hz, 1H), 7.30-7.63 (m, 4H aromatic ring), 8.49 (s, 1H NH)

$^{13}$C NMR (DMSO) δ ppm: 172.97 (C=O), (138.80, 135.76, 133.21, 127.38, 126.40 aromatic ring), 116.09 (C=C), 79.52, 78.99, 78.46, 70.97 (C12), 70.39 (C3), 66.20 (C7), 65.85, 61.35, 59.67 (CH$_3$), 49.22, 48.55, (45.92, 41.48, 41.36, 40.51, 40.18, 35.51, 35.27, 35.18, 34.87, 34.35, 32.31, 28.51, 27.28, 26.20 steroid ring), 45.70 (CH$_3$), 31.50 (CH$_2$), 22.79, 22.68, 22.58 (C19), 17.11 (C21), 14.61, 12.29 (C18).

MS (+APCI) m/z=609.4619

IR (KBr) ν=3347, 2929, 2862, 1775, 1694, 1627 (C=O), 1551 cm$^{-1}$

Synthesis of N-[1-phenyl-1-[(4-vinylphenyl)methyl] piperidin-1-ium-4-yl]cholanamide chloride (71)

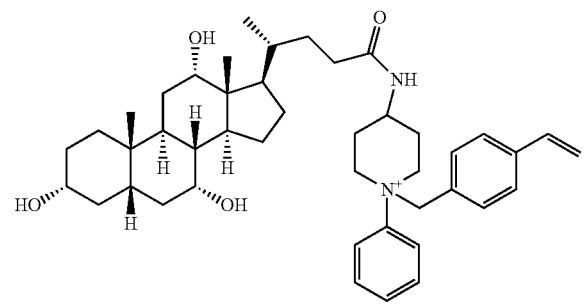

N-(1-phenyl-4-piperidyl) cholanamide (13) (1.5 g, 3.5 mmol) was dissolved in DCM (20 mL). Vinyl benzyl chloride (1.5 mL, 10.5 mmol) was added. The reaction was protected from the light and left to stir overnight. The reaction was heated under reflux for 24 hours. The product precipitated out, which was then collected by filtration and washed with petrol 40-60 (30 mL). Further purification by solvent extraction (×3) between petrol 40-60 (10 mL) and methanol (10 mL) left a white solid.

$^1$H NMR (CDCl$_3$) δ ppm: 0.57 (s32H Me-18) 0.88 (s 3H Me-19) 0.98 (d 3H Me-21) 1-2.43 (steroid structure) 3.18 (tt, J=14.7, 7.3 Hz, 7H CH$_2$ ring), 3.61 (d, J=3.7 Hz, 1H CH-3), 3.77 (d, J=3.6 Hz, 1H CH-7), 4.04 (d, J=3.2 Hz, 1H CH-12), 4.14 (d, J=3.3 Hz, 1H C3-OH), 4.36 (d, J=4.0 Hz, 1H C7-OH), 4.53 (s, 1H C12-OH), 5.38 (d, J=10.9 Hz, 1H CH=CH), 5.95 (d, J=17.7 Hz, 1H CH=CH), 6.79 (dd, J=17.6, 11.0 Hz, 1H), 7.73-7.43 (m, 4H aromatic ring), 8.07 (t, J=5.7 Hz, 1H NH).

$^{13}$C NMR (DMSO) δ ppm: 172.94 (C=O), (138.80, 135.78, 133.22, 127.43, 126.42, aromatic ring), 116.15 (C=C), 70.95 (C12), 70.37 (C3), 66.19 (C7), 65.83, 61.33, 49.24, (45.94, 45.70, 41.48, 41.36, 40.51, 40.17, 35.50, 35.28, 35.19, 34.87, 34.35, 32.32, 31.51, 30.25, 28.54, 27.29, 26.20 steroid ring), 22.79, 22.67, 22.60 (C19), 17.12 (C21), 12.31 (C18).

MS (+APCI) m/z=Found 609.4612; expected 683.4782 (MI-73) MI−(vbc+propane)

IR (KBr) ν=3356, 2925, 2862, 2164, 1648 (C=O), 1548 cm$^{-1}$

Synthesis of N-Boc-1,4-butanediamine (72)

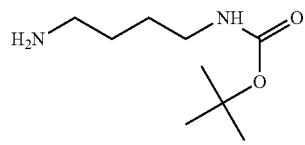

1,4-diaminobutane (1 mL, 12.94 mmol) was dissolved in DCM (20 mL) and put on ice. Di-tert-butyl dicarbonate (0.3 g, 1.29 mmol) in DCM (5 mL) was dripped in over 50 minutes. The reaction was left at ice temperature for 12 hours. The reaction was washed with water (100 mL) followed by brine (100 mL), before being dried with magnesium sulphate. The solvent was removed under vacuum to leave a yellow solid.

Yield=0.087 g (8.7%)

$^1$H NMR (CDCl$_3$) δ ppm: 1.40-1.61 (m 12H) 3.13 (q J=6.1 Hz 2H) 4.55 (s 1H)

$^{13}$C NMR (DMSO) δ ppm: 155.57 (C=O), 77.26 (C), 28.36 (CH$_3$), 28.21, 27.29, 26.93, 26.86.

MS (+APCI) m/z=Found 289.2126; expected 188. Diamer produced.

IR (KBr) ν=3372 2983 2941 2847 1681 (C=O) 1521 cm$^{-1}$

Polymerisation of N-(4-cholanamidobutyl)-2-methyl-prop-2-enamide

N-(4-cholanamidobutyl)-2-methyl-prop-2-enamide (75) (0.6 g, 0.96 mmol) was dissolved in methanol (7 mL). Styrene (2.4 mL, 23.04 mmol) was added along with a small amount of AIBN. The boiling tube was purged with argon 3 times and put into an oil bath at 60° C. for 48 hours. The white solid precipitate was collected by filtration, dissolved into chloroform and dripped onto stirring methanol (50 mL) for purification. The polymer was collected by filtration, washed with methanol (30 mL) and dried at room temperature under vacuum.

Polymerisation of 3α,12α diacroylate-7αhydroxycholic acid

3α,12α diacroylate-7αhydroxycholic acid (63) (0.175 g) was dissolved in toluene (2.5 mL). AIBN (0.1 g) was added, along with EGDMA (0.82 mL). 1000 of the solution was pipetted out into a 96 well plate and a PTFE-lined cover was clamped across the top of the plate to seal the wells. It was place in at oven set at 60° C. for 12 hours. The products were white discs.

Polymerisation of methacrylate 7α,12α dihydroxyl cholic acid

Methacrylate 7α,12α dihydroxyl cholic acid (65) (0.2 g) was dissolved in toluene (3.5 mL). AIBN (0.1 g) was added, along with EGDMA (0.8 mL). 1000 of the solution was pipetted out into a 96 well plate and clamped. It was place in at oven set at 60° C. for 12 hours. The products were white discs.

Polymerisation of 3α hydroxyl 7α,12α diacetate methyl cholate

3α hydroxyl 7α,12α diacetate methyl cholate (77) (0.5 g) was added to a round bottomed flask along with bis[acetylacetonato]copper (0.02 g) and vinyl benzyl chloride (2 mL). The reaction was heated to 120° C. for 4.5 hours. The crude product was purified using column chromatography with petrol 60-80, slowly increasing the amount of ethyl acetate (0-100%). The solvents were removed under reduced pressure and the polymer was dried at room temperature under vacuum.

Polymerisation of 3-acetamidopropyl-dimethyl-[(4-vinylphenyl)methyl]ammonium chloride (70)

3-acetamidopropyl-dimethyl-[(4-vinylphenyl)methyl] ammonium chloride (70) (0.5 g) was dissolved in ethanol (4 mL). Styrene (3.9 mL) was added along with AIBN (100 mg). The reaction was degassed and heated to 65° C. for 12 hours where a white solid precipitated out. It was purified by dissolving in chloroform (20 mL) and dripping into stirring methanol (100 mL). The product was collected by filtration and dried at room temperature under vacuum to give a white solid.

Proton NMR analysis shows very little incorporation of N-[3-(dimethylamino)propyl]cholanamide (12) into the polymer.

3-acetamidopropyl-dimethyl-[(4-vinylphenyl)methyl] ammonium chloride (70)(0.25 g) was dissolved in ethanol (4 mL) along with AIBN (100 mg). Tert-butyl methacrylate (0.23 mL) was added. The mixture was degassed which argon and heated to 60° C. for 4 days. The solution was purified by dripping onto ethyl acetate (75 mL) to give a white powdery solid which was dried at room temperature under vacuum.

Proton NMR analysis showed that no polymerisation had taken place.

3-acetamidopropyl-dimethyl-[(4-vinylphenyl)methyl] ammonium chloride (70) (0.25 g) was suspended in propan-2-ol (6 mL) along with AIBN (100 mg). The mixture was degassed and heated to 70° C. for 5 days. The white, cloudy solution was collected by filtration to give a off white solid which was dried at room temperature under vacuum.

No NMR analysis could be undertaken of this polymer due to its insolubility.

Polymerisation of Synthesis of N-[1-phenyl-1-[(4-vinylphenyl)methyl]piperidin-1-ium-4-yl]cholanamide chloride (71)

Synthesis of N-[1-phenyl-1-[(4-vinylphenyl)methyl]piperidin-1-ium-4-yl]cholanamide chloride (70) (0.3 g) was dissolved in proan-2-ol (8 mL) along with AIBN (100 mg). The mixture was degassed with argon and heated to 70° C. for 6 days. An white solid precipitated out, which was collected by filtration and dried at room temperature under vacuum.

Proton NMR analysis shows a very short chained polymer was synthesised.

Synthesis of 4-benzylbenzoyl chloride (96)

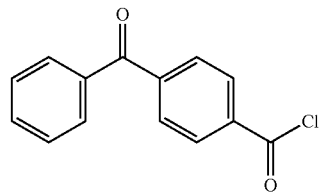 [SMILES: O=C(Cl)c1ccc(C(=O)c2ccccc2)cc1]

4-benzyl benzoic acid (1 g, 4.42 mmol) was added to a dry flask along with thionyl chloride (3 mL), DMF (0.5 mL) and toluene (13 mL). The flask was heated under reflux for 5 days. The solvent was removed under reduced pressure and the product was re-dissolved in toluene (5 mL) twice and the solvent removed. The product was dried under vacuum at room temperature under vacuum to give a white solid.

Yield=1.03 g $^1$H NMR (CDCl$_3$) δ ppm: 8.56, 8.54, 8.29, 8.24, 8.24, 8.23, 8.21, 8.20, 8.20, 8.19, 8.18, 7.93, 7.90, 7.89, 7.88, 7.87, 7.86, 7.86, 7.85, 7.84, 7.82, 7.81, 7.80, 7.80, 7.78, 7.78, 7.77, 7.67, 7.66, 7.65, 7.64, 7.63, 7.62, 7.62, 7.61, 7.60, 7.60, 7.59, 7.58, 7.54, 7.53, 7.52, 7.50, 7.50, 7.49, 7.48, 7.47, 7.47, 7.24, 6.82, 3.95, 3.47, 3.33, 2.15, 1.79, 0.217.83-7.73 (m, 2H), 7.96-7.80 (m, 2H), 8.30-8.13 (m, 2H), $^1$H NMR (250 MHz, Chloroform-d) δ 7.69-7.56 (m, 1H), 7.50 (tt, J=6.6, 1.5 Hz, 2H).

MS (+APCI) m/z=Found 245.0366; calculated for C$_{14}$H$_{10}$Cl$_1$O$_2$ 245.0364; 0.9 ppm

Synthesis of N-(4-benzoylphenyl)formamide cholate (98)

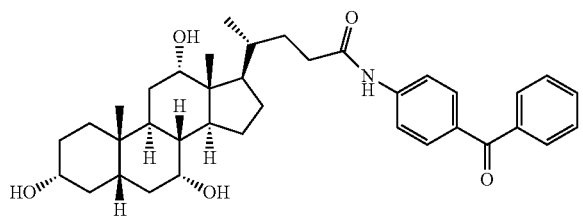

Cholic acid (0.5 g, 1.2 mmol) was dissolved in THF (30 mL) along with triethylamine (2.9 mL, 0.3 mmol). The solution was put on ice for 10 minutes before ethylchloroformate (0.13 mL, 0.013 mmol) was dripped in over 10 minutes. The solution was allowed to react for two hours at room temperature. 4-aminobenzophenone (0.23 g, 1.2 mmol) was added and left to react for 3 hours. The reaction was quenched with water (30 mL). The mixture was washed with water (3×30 mL). The organic layer was dried over magnesium sulphate and the solvent was evaporated under reduced pressure. Solvent extraction between water and ethyl acetate was preformed 3 times before the organic layer was removed under reduced pressure. The product was dried at room temperature under vacuum.

MS (+APCI) m/z=Found 588.3680; calculated for C$_{37}$H$_{50}$N$_1$O$_5$ 588.3684; −0.6 ppm

Synthesis of methyl lithocholate (99)

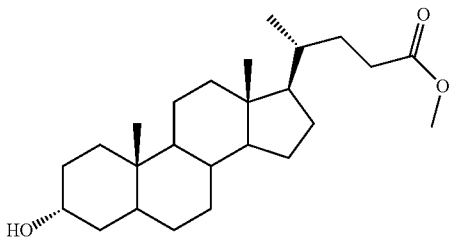 [SMILES: COC(=O)CC[C@@H](C)[C@H]1CCC2C3CCC4C[C@H](O)CC[C@]4(C)C3CC[C@@]21C]

Lithocholic acid (5.0 g, 0.01329 mol) was added to methanol (90 mL) to produce a suspension. Acetyl chloride (0.5 mL, 0.006 mol) was then added. The solution was heated and stirred at 80° C. for 40 minutes as a homogeneous solution, then allowed to cool overnight in an ice bath. This was added to water (150 mL) and the resulting precipitate was collected by filtration, washed with water (3×20 mL) and dried under vacuum.

Yield; 5 g, 0.01328 mol, 96.5%.

Melting point: 75-76° C.

$^1$H NMR (250 MHz) δ=0.66 (s, 3H, 18-CH$_3$), 0.94 (s, 3H, 19-CH$_3$), 3.65 (m, 1H, 3-CH), 3.69 (s, 3H, O—CH$_3$) ppm.

$^{13}$C NMR (62.9 MHz) δ=12.0 (CH$_3$, C18), 18.6 (CH$_3$, C21), 20.8 (CH$_2$, C11), 23.7 (CH$_3$, C19), 24.2 (CH$_2$, C15), 26.4 (CH$_2$, C7), 27.2 (CH$_2$, C6), 28.2 (CH$_2$, C16), 30.5 (CH$_2$, C2), 30.9 (CH$_2$, C22), 31.0 (CH$_2$, C23), 34.5 (C, C10), 35.3 (CH, C20), 35.4 (CH$_2$, C1), 35.8 (CH, C8), 36.4 (CH$_2$, C4), 40.1 (CH$_2$, C12), 40.4 (CH, C9), 42.0 (CH, C5), 42.7 (C, C13), 51.5 (O—CH$_3$) 55.9 (CH, C17), 56.5 (CH, C14), 71.9 (CH, C3), 174.8 (CO, C24) ppm.

IR; 3347 (OH stretch), 2937 (C—H), 2859 (O—CH$_3$), 1733 (C=O), 1640, 1436, 1206, 1043 (R$_2$CH—OH) cm$^{-1}$.

Synthesis of methyl deoxycholate (100)

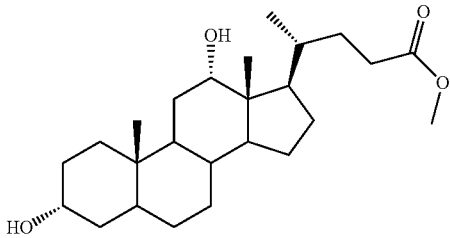 [SMILES: COC(=O)CC[C@@H](C)[C@H]1CCC2C3CCC4C[C@H](O)CC[C@]4(C)C3C[C@H](O)[C@@]21C]

Deoxycholic acid (5.0 g 0.01 mol) was dissolved in methanol (30 mL) and treated with acetyl chloride (0.5 mL, 0.006 mol). The solution was heated and stirred at 80° C. for 40 minutes then allowed to cool overnight in an ice bath. The resultant crystals were collected by vacuum filtration to produce a white crystalline powder. This was washed with water (2×20 mL) and dried under vacuum.

Yield; 1.81 g, 0.004 mol, 35%.

Melting point: 70-72° C.

$^1$H NMR (250 MHz) δ=0.68 (s, 3H, 18-CH$_3$), 0.91 (s, 3H, 19-CH$_3$), 3.60 (m, 1H, 3-CH), 3.67 (s, 3H, O—CH$_3$), 3.99 (s, 1H, 12-CH) ppm.

$^{13}$C NMR (62.9 MHz) δ=12.8 (CH$_3$, C18), 17.3 (CH$_3$, C21), 23.2 (CH$_3$, C19), 26.6 (CH$_2$, C15), 26.1 (CH$_2$, C7), 27.1 (CH$_2$, C6), 27.4 (CH$_2$, C16), 28.7 (CH$_2$, C11), 30.5 (CH$_2$, C2), 30.9 (CH$_2$, C23), 31.1 (CH$_2$, C22), 33.7 (CH, C9), 34.1 (C, C10), 35.1 (CH$_2$, C1), 35.2 (CH, C20), 36.0 (CH$_2$, C4), 36.4 (CH, C8), 42.0 (CH, C5), 46.5 (C, C13), 47.3 (CH, C17), 48.3 (CH, C14), 51.5 (O—CH$_3$) 71.8 (CH, C3), 73.1 (CH$_2$, C12), 174.7 (CO, C24) ppm.

IR; 3474 (OH stretch) 2985 (C—H), 2852 (O—CH$_3$), 1743 (C=O), 1450, 1380, 1040 (R$_2$CH—OH) cm$^{-1}$.

$^{13}$C NMR (62.9 MHz) δ=12.0 (CH$_3$, C18), 18.2 (CH$_3$, C21), 20.8 (CH$_2$) 23.3 (CH$_3$, C19), 24.2 (CH$_2$, C15), 26.4 (CH$_2$, C7), 27.1 (CH$_2$, C6), 28.2 (CH$_2$, C16), 30.5 (CH$_2$, C11), 30.9 (CH$_2$, C2), 31.1 (CH$_2$, C23), 34.5 (CH, C9), 35.3 (C, C10), 35.8 (CH$_2$, C1), 36.4 (CH, C20), 40.1 (CH, C5), 40.4 (C, C13), 55.9 (CH$_2$), 56.5 (CH$_2$), 61.3 (CH$_2$) 65.9 (CH, C3), 71.8 (CH$_2$, C12), 174.7 (CO, C24) ppm.

IR=3509 (OH), 3309 (OH), 2925 (alkyl), 2857 (alkyl), 1718 (C=O), 1449, 1356, 1292, 1189.78 (C=O ester stretch), 1027.73 (R$_2$CH—OH) cm$^{-1}$.

MS (+ESI) m/z=Found 454.3527 (M+H)$^+$; calculated for C$_{26}$H$_{48}$NO$_5$ 454.3527; 0.0 ppm.

Synthesis of (4R)—N-(2-dimethylaminoethyl)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]pentanamide (101)

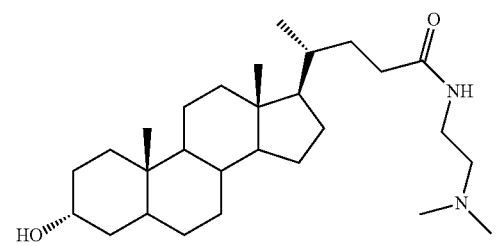 [SMILES: C[C@H](CCC(=O)NCCN(C)C)[C@H]1CCC2C3CCC4C[C@H](O)CC[C@]4(C)C3CC[C@@]21C]

A mixture of lithocholic acid (1.0 g 0.005 mol) and N, N'-dimethylethylenediamine (0.16 mL 0.001 mol) was dissolved in toluene (20 mL). The solution was heated at reflux for 24 hours. More N, N'-dimethylethylenediamine (0.32 mL 0.003 mol) of was added and the mixture was heated at reflux for 24 h. Water (100 mL) was added to the solution. The resulting precipitate was collected by vacuum filtration and the crude product was recrystallized from ethyl acetate to produce a white powder.

Yield 0.85 g, 0.001 mol, 69%.

$^1$H NMR (250 MHz) CDCl$_3$ δ=0.64 (s, 3H, 18-CH$_3$), 0.92 (s, 3H, 19-CH$_3$), 2.21 (s, 6H, 2×CH$_3$), 2.42 (t, 2H CH$_2$ J=5.0) 3.34 (q, 2H, CH$_2$, J=7.5), 3.63 (m, 1H, 3-CH), 6.20 (broad s, 1H, NH) ppm.

$^{13}$C NMR (62.9 MHz) δ=12.0 (CH$_3$, C18), 18.3 (CH$_3$, C21), 20.8 (CH$_2$, C11), 23.3 (CH$_3$, C19), 24.2 (CH$_2$, C15), 26.4 (CH$_2$, C7), 27.2 (CH$_2$, C6), 28.2 (CH$_2$, C16), 30.5 (CH$_2$, C2), 31.7 (CH$_2$, C22), 33.5 (CH$_2$, C23), 34.5 (C, C10), 35.3 (CH, C20), 35.5 (CH$_2$, C1), 35.8 (CH, C8), 36.4 (CH$_2$, C4), 36.6 (CH$_2$) 40.2 (CH$_2$, C12), 40.4 (CH, C9), 42.1 (CH, C5), 42.7 (C, C13), 45.1 (CH$_3$) 56.0 (CH, C17), 56.5 (CH, C14), 57.9 (CH$_2$) 71.8 (CH, C3), 173.7 (CO, C24) ppm.

IR; 3377 (OH), 3293 (NH) 2929 (C—H), 2870 (C—H), 1646 (C=O), 1543, 1445 cm$^{-1}$.

MS (+ESI) m/z=Found 447.3943 (M+H)$^+$; calculated for C$_{28}$H$_{51}$N$_2$O$_2$ 447.3945; 0.5 ppm.

Synthesis of (4R)-4-[(3R,10S,12S,13R,17R)-3,12-dihydroxy-10,13-dimethyl-2,3,4,5,6,7,8,9,11,12,14,15,16,17-tetradecahydro-1H-cyclopenta[a]phenanthren-17-yl]-N-(2-dimethylaminoethyl)pentanamide (102)

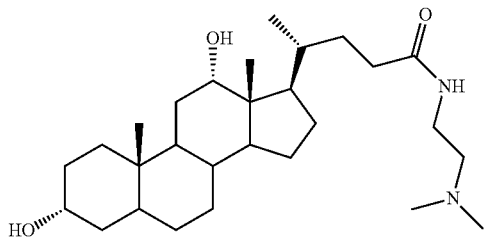 [SMILES: C[C@H](CCC(=O)NCCN(C)C)[C@H]1CCC2C3CCC4C[C@H](O)CC[C@]4(C)C3C[C@H](O)[C@@]21C]

A mixture of deoxycholic acid (1.0 g 0.002 mol) and N,N'-dimethylethylenediamine (0.16 mL 0.001 mol) was dissolved in toluene (20 mL). The solution was heated at reflux for 24 hours. More N, N'-dimethylethylenediamine (0.16 mL 0.001 mol) was added and the reaction mixture was heated at reflux for a further 24 hours. The solvent was then evaporated under reduced pressure. The residue was triturated with hot water (~10 mL) and washed with water (3×20 mL), then dried under vacuum.

Yield 0.310 g, 0.0006 mol, 24%.

$^1$H NMR (CDCl$_3$) (250 MHz) δ=0.68 (s, 3H, 18-CH$_3$), 0.91 (s, 3H, 19-CH$_3$), 1.01 (d, 3H, 21-CH$_3$, J=6.5), 2.26 (s, 6H, 2×CH$_3$), 2.46 (t, 2H, CH$_2$, J=5.0), 3.34 (t, 2H, CH$_2$, J=5.0), 3.61 (m, 1H, 3-CH), 3.97 (broad singlet, 1H, 12-CH), 6.44 (broad singlet, 1H, NH) ppm.

$^{13}$C NMR (62.9 MHz) δ=12.7 (CH$_3$, C18), 17.5 (CH$_3$, C21), 23.1 (CH$_3$, C19), 23.6 (CH$_2$, C15), 26.1 (CH$_2$, C7), 27.1 (CH$_2$, C6), 27.8 (CH$_2$, C16), 28.5 (CH$_2$, C11), 30.5 (CH$_2$, C2), 31.6 (CH$_2$, C23), 33.3 (CH$_2$, C22), 33.6 (CH, C9), 34.1 (C, C10), 35.2 (CH$_2$, C1), 36.0 (CH, C20), 36.4 (CH$_2$, C4), 42.0 (CH, C5), 44.9 (C, C13), 46.5 (CH$_3$) 47.3 (CH, C17), 48.2 (CH, C14), 57.9 (CH$_3$) 71.7 (CH, C3), 73.0 (CH$_2$, C12), 172.7 (CO, C24) ppm.

IR=3305, (OH), 2929 (alkyl), 2861 (alkyl), 1720 (C=O), 1044 (R$_2$CH—OH) cm$^{-1}$ MS (+ESI) m/z=Found 463.3888 (M+H)$^+$; calculated for C$_{28}$H$_{51}$N$_2$O$_3$ 463.3894; 1.3 ppm.

Synthesis of (4R)—N-[3-(dimethylamino)propyl]-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]pentanamide (103)

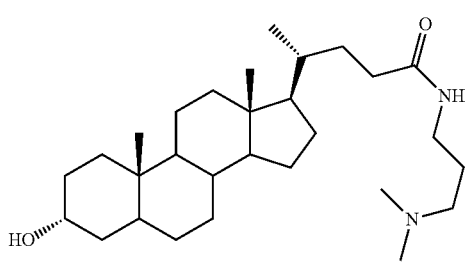 [SMILES: C[C@H](CCC(=O)NCCCN(C)C)[C@H]1CCC2C3CCC4C[C@H](O)CC[C@]4(C)C3CC[C@@]21C]

A mixture of methyl lithocholate (0.5 g 0.001 mol) and 3-dimethyl-propylamine (3 mL, 0.02 mol) was heated and stirred at 140° C. for 24 hours in an argon environment. Ice water (3 mL) was added to the material and left to stir for two hours at room temperature. The resulting solid was then collected by filtration washed with water (3×20 mL) and left to dry overnight under vacuum to produce off brown crystals. Yield, 0.41 g, 0.0008 mol, 69%.

Melting point: 177.0-178.3° C.

$^1$H NMR CDCl$_3$ (250 MHz) δ=0.61 (s, 3H, 18-CH$_3$) 0.89 (d, 3H, 19-CH$_3$) 1.57 (s, 3H, 21-CH$_3$) 2.22 (s, 6H, 2×CH$_3$) 2.36 (t, 2H, CH$_2$, J=6.3) 3.30 (t, 2H, CH$_2$, J=5.6) 3.59 (m, 1H, 3-CH) 6.95 (s, 1H, NH) ppm.

$^{13}$C NMR (62.9 MHz) δ=12.0 (CH$_3$, C18), 18.3 (CH$_3$, C21), 20.8 (CH$_2$, C11), 23.3 (CH$_3$, C19), 24.2 (CH$_2$, C15), 24.3 (CH$_2$, C7), 26.4 (CH$_2$), 27.1 (CH$_2$, C6), 28.2 (CH$_2$, C16), 30.5 (CH$_2$, C2), 31.7 (CH$_2$, C22) 34.5 (C, C10), 35.3 (CH, C20), 35.5 (CH$_2$, C1), 35.8 (CH, C8), 36.4 (CH$_2$, C4), 40.1 (CH$_2$, C12), 40.3 (CH, C9), 42.0 (CH, C5), 42.7 (C, C13), 43.0 (CH$_3$) 55.3 (CH, C17), 55.9 (CH, C14), 56.4 (CH$_2$) 71.9 (CH, C3), 174.9 (CO, C24) ppm.

IR=3310-3318 (OH—NH), 2730 (alkyl), 2859 (alkyl), 2946 (alkyl), 1648 (C=O), 1047 (CH—OH) cm$^{-1}$.

MS (ES+APCI) m/z=Found 461.4105 (M+H)$^+$; calculated for C$_{29}$H$_{53}$N$_2$O$_2$ 461.4107; 0.4 ppm.

Synthesis of (4R)-4-[(3R,10S,12S,13R,17R)-3,12-dihydroxy-10,13-dimethyl-2,3,4,5,6,7,8,9,11,12,14,15,16,17-tetradecahydro-1H-cyclopenta[a]phenanthren-17-yl]-N-[3-(dimethylamino)propyl]pentanamide (104)

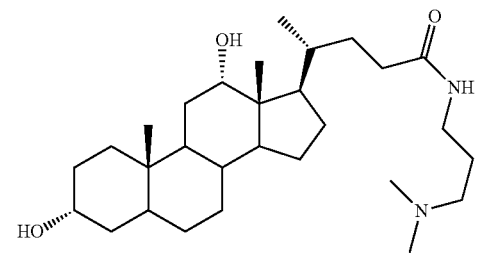 [SMILES: C[C@H](CCC(=O)NCCCN(C)C)[C@H]1CCC2C3CCC4C[C@H](O)CC[C@]4(C)C3C[C@H](O)[C@@]21C]

A mixture of methyl deoxycholate (0.5 g 0.002 mol) and 3-dimethyl-1-propylamine (3.63 mL 0.03 mol) were added together and heated to 100° C. for 5 days then allowed to cool to ambient room temperature. Ice water (40 mL) was then added and left to stir for 2 hours and the precipitate collected by vacuum filtration, washed with water (3×20 mL) and dried under vacuum.

Yield, 0.41 g, 0.0008 mol, 73%.

Melting point: 123-127° C.

$^1$H NMR (CDCl$_3$) (250 MHz) δ=0.64 (s, 3H, 18-CH$_3$), 0.92 (s, 3H, 19-CH$_3$), 2.23 (s, 6H, 2×CH$_3$), 2.42 (t, 2H, CH$_2$, J=5.0), 3.325 (q, 2H, CH$_2$, J=7.5), 3.63 (m, 1H, 3-CH), 6.21 (broad singlet, 1H, NH) ppm.

$^{13}$C NMR (62.9 MHz) δ=12.0 (CH$_3$, C18), 18.3 (CH$_3$, C21), 20.8 (CH$_2$, C11), 23.3 (CH$_3$, C19), 24.2 (CH$_2$, C15), 26.4 (CH$_2$, C7), 27.2 (CH$_2$, C6), 28.2 (CH$_2$, C16), 30.5 (CH$_2$, C2), 31.7 (CH$_2$, C22), 33.5 (CH$_2$, C23), 34.5 (C, C10), 35.3 (CH, C20), 35.5 (CH$_2$, C1), 35.8 (CH, C8), 36.4 (CH$_2$, C4), 36.6 (CH$_2$), 40.2 (CH$_2$, C12), 40.4 (CH, C9), 42.1 (CH, C5), 42.7 (C, C13), 45.1 (CH$_2$), 56.0 (CH, C17), 56.5 (CH$_2$), 57.9 (CH, C14), 71.8 (CH, C3), 173.7 (CO, C24) ppm.

IR=3376 (NH and OH), 2938 (alkyl), 2861 (alkyl), 1643 (C=O), 1544, 1444, 1378, 1045 (R$_2$CH—OH) cm$^{-1}$.

MS (+ES APCI) m/z=Found 447.3943 (M+H)+; calculated for $C_{28}H_{51}N_2O_2$ 447.3943; 0.5 ppm.

Synthesis of 1-(4-butylpiperazin-1-yl)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]pentan-1-one (105)

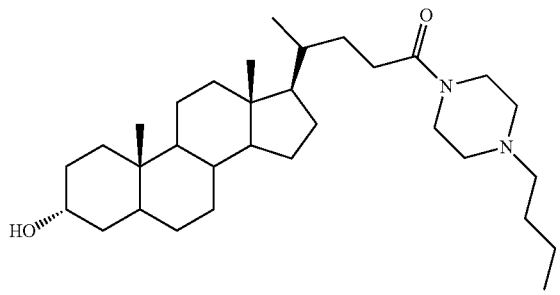 [SMILES: CCCCN1CCN(C(=O)CCC(C)[C@H]2CCC3C4CCC5C[C@H](O)CC[C@]5(C)C4CC[C@@]32C)CC1]

Following a modified method (Fini et al., 1992), lithocholic acid (0.5 g 0.001 mol) was dissolved in tetrahydrofuran (20 mL) with triethylamine (0.4 mL 0.002 mol). The solution was cooled for 10 minutes in cold water. Ethyl chloroformate (0.2 mL 0.001 mol) was then added dropwise over a ten minute period. Once added, the cold water was removed and the solution was stirred for 2 hours. After 2 hours, solvent removed under reduced pressure then re-dissolved in dichloromethane and washed with water then 1-butylpiperazine (0.25 mL 0.001 mol) was added and the solution was stirred for 24 hours. Water (50 mL) was then added and the solution extracted with ethyl acetate (3×50 mL). The organic layers were combined and washed with saturated sodium hydrogen carbonate solution (3×50 mL). The organic layer was dried over magnesium sulphate. Solvent was evaporated under reduced pressure.

Yield; 0.16 g, 0.0003 mol, 23.5%.

Melting point: 172.7-173.1° C.

$^1$H NMR (CDCl$_3$) (250 MHz) δ=0.61 (s, 3H, 18-CH$_3$), 0.88 (s, 3H, 19-CH$_3$), 1.34 (m, 4H, CH$_2$), 2.35 (m, 6H, CH$_2$), 3.45 (broad singlet, 2H, CH$_2$), 3.60 (broad singlet, 2H, CH$_2$) ppm.

$^{13}$C NMR (62.9 MHz) δ=12.0 (CH$_3$, C18), 14.0 (CH$_3$), 18.5 (CH$_3$, C21), 20.6 (CH$_2$, C11), 20.8 (CH$_2$) 23.3 (CH$_3$, C19), 24.2 (CH$_2$, C15), 26.4 (CH$_2$, C7), 27.2 (CH$_2$, C6), 28.2 (CH$_2$, C16), 28.8 (CH$_2$), 30.2 (CH$_2$, C2), 30.5 (CH$_2$, C22), 31.4 (CH$_2$, C23), 34.5 (C, C10), 35.3 (CH, C20), 35.6 (CH$_2$, C1), 35.8 (CH, C8), 36.4 (CH$_2$, C4), 40.1 (CH$_2$, C12), 40.4 (CH, C9), 41.4 (CH, C5), 42.1 (C, C13), 42.8 (CH$_2$), 45.6 (CH$_2$), 52.9 (CH$_2$), 53.4 (CH$_2$), 53.4 (CH$_2$), 56.0 (CH, C17), 56.5 (CH, C14), 58.3 (CH$_2$), 71.7 (CH, C3), 172.1 (CO, C24) ppm.

IR=3381, (OH), 2916 (alkyl), 2852 (alkyl), 1616 (C=O), 1437, 1253, 1036 (R$_2$CH—OH) cm$^{-1}$.

MS (+ESI) m/z=Found 501.4409 (M+H)+; calculated for $C_{32}H_{57}N_2O_2$ 501.4409; 1.1 ppm.

Synthesis of (4R)-1-(4-butylpiperazin-1-yl)-4-[(3R,10S,12S,13R,17R)-3,12-dihydroxy-10,13-dimethyl-2,3,4,5,6,7,8,9,11,12,14,15,16,17-tetradecahydro-1H-cyclopenta[a]phenanthren-17-yl]pentan-1-one (106)

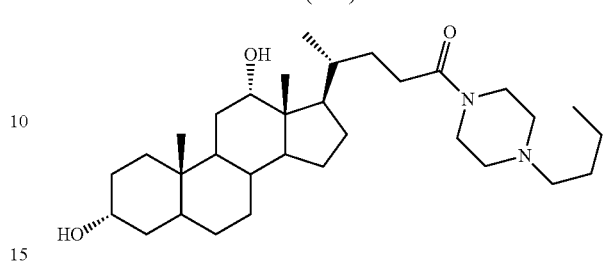

Deoxycholic acid (0.5 g 0.001 mol) was dissolved in tetrahydrofuran (20 mL) with triethylamine (0.4 mL 0.001 mol). The solution was cooled for 10 minutes in cold water. Ethyl chloroformate (0.2 mL 0.001 mol) was then added dropwise over a ten minute period. Once added, the cold water was removed and the solution was stirred for 2 hours. After 2 hours, solvent removed under reduced pressure then re-dissolved in dichloromethane and washed with water then 1-butylpiperazine (0.25 mL 0.001 mol) was added and the solution was stirred for 24 hours. Water (50 mL) was then added and the solution extracted with ethyl acetate (3×50 mL). The organic layers were combined and washed with saturated sodium hydrogen carbonate solution (3×50 mL). The organic layer was dried over magnesium sulphate. Solvent was evaporated under reduced pressure.

Yield; 0.04 g, 0.0004 mol, 6%.

Melting point: 92.3-93.5° C.

$^1$H NMR (CDCl$_3$) (250 MHz) δ=0.68 (s, 3H, 18-CH$_3$), 0.89 (s, 3H, 19-CH$_3$), 0.98 (d, 3H, 21-CH$_3$ J=7.5), 2.38 (m, 6H, CH$_2$), 3.48 (broad singlet, 2H, CH$_2$), 3.62 (broad singlet, 2H, CH$_2$), 3.98 (broad singlet, 1H, 12-CH) ppm.

$^{13}$C NMR (62.9 MHz) δ=12.7 (CH$_3$, C18), 14.0 (CH$_2$), 17.5 (CH$_3$, C21), 20.6 (CH$_2$), 23.1 (CH$_3$, C19), 23.6 (CH$_2$, C15), 27.5 (CH$_2$, C7), 28.6 (CH$_2$, C6), 28.8 (CH$_2$, C16), 30.1 (CH$_2$, C11), 30.5 (CH$_2$, C2), 31.3 (CH$_2$, C23), 33.6 (CH$_2$, C22), 34.1 (CH, C9), 35.2 (C, C10), 35.2 (CH$_2$, C1), 36.0 (CH, C20), 36.4 (CH$_2$, C4), 41.4 (CH$_2$), 42.0 (CH, C5), 45.6 (CH$_2$) 46.5 (CH$_2$) 47.2 (CH, C17), 48.3 (CH, C14), 52.8 (CH$_2$) 53.4 (CH$_2$) 71.8 (CH, C3), 73.1 (CH, C12), 171.9 (CO, C24) ppm.

IR=3300 (OH), 2930 (alkyl), 2861 (alkyl), 1594 (C=O), 1443, 1282, 1162 (C=O ester stretch), 1011 (R$_2$CH—OH) cm$^{-1}$.

MS (+ESI) m/z=Found 517.4359 (M+H)+; calculated for $C_{32}H_{57}N_2O_3$ 517.4364; 0.9 ppm.

Synthesis of 4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]-N-(2-pyrrolidin-1-ylethyl)pentanamide (107)

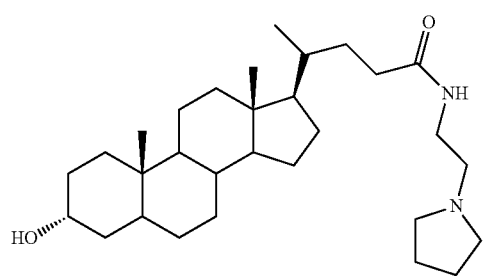 [SMILES: CC(CCC(=O)NCCN1CCCC1)[C@H]1CCC2C3CCC4C[C@H](O)CC[C@]4(C)C3CC[C@@]21C]

Lithocholic acid (0.5 g 0.001 mol) was dissolved in tetrahydrofuran (20 mL) with triethylamine (0.20 mL, 0.001 mol). The solution was cooled for 10 minutes in cold water. Ethyl chloroformate (0.20 mL, 0.001 mol) was then added dropwise over a ten minute period. Once added, the cold water was removed and the solution was stirred for 2 hours at room temperature. After 2 hours 1-(2-aminoethyl)pyrolidine (0.25 mL, 0.002 mol) was added and the solution was stirred for 3 hours. Water (50 mL) was then added and the solution was extracted with ethyl acetate (3×50 mL). The organic layers were combined and dried over magnesium sulphate. The solvent was evaporated under reduced pressure to produce a white powder.

Yield; 0.56 g, 0.001 mol, 91.8%.

Melting point: 144.1-145.1° C.

$^1$H NMR (CDCl$_3$) (250 MHz) δ=0.64 (s, 3H, 18-CH$_3$), 0.92 (s, 3H, 19-CH$_3$) 0.94 (d, 3H, 21-CH$_3$, J=7.5), 1.80 (m, 4H, CH$_2$), 2.54 (broad singlet, 4H, CH$_2$), 2.60 (t, 2H, CH$_2$, J=5.0) 3.63 (q, 2H, CH$_2$, J=5.0) 3.63 (m, 1H, 3-CH), 6.13 (broad s, 1H, NH) ppm.

$^{13}$C NMR (62.9 MHz) δ=12.0 (CH$_3$, C18), 18.4 (CH$_3$, C21), 20.8 (CH$_2$, C11), 23.4 (CH$_3$, C19), 24.2 (CH$_2$, C15), 26.4 (CH$_2$, C7), 27.2 (C H$_2$, C6), 28.2 (CH$_2$, C16), 30.5 (CH$_2$, C2), 31.7 (CH$_2$, C22), 33.5 (CH$_2$, C23), 34.5 (C, C10), 35.3 (CH, C20), 35.5 (CH$_2$, C1), 35.8 (CH, C8), 36.4 (CH$_2$, C4), 37.7 (CH$_2$) 40.2 (CH$_2$, C12), 40.4 (CH$_2$, C9), 42.1 (CH, C5), 42.7 (C, C13), 53.8 (CH$_2$), 54.9 (CH$_2$) 56.0 (CH, C17), 56.5 (CH, C14), 71.8 (CH, C3), 173.9 (CO, C24) ppm.

IR=3415 (NH), 3310 (OH), 2933 (alkyl), 2865 (alkyl), 2872 (alkyl), 1648 (C=O), 1548, 1444, 1378, 1265 (C=O ester stretch), 1064 (R$_2$CH—OH) cm$^{-1}$.

MS (+ESI) m/z=Found 473.4096 (M+H)$^+$; calculated for C$_{30}$H$_{53}$N$_2$O$_2$ 473.4102; 1.2 ppm.

Synthesis of 4-[(3R,10S,12S,13R,17R)-3,12-dihydroxy-10,13-dimethyl-2,3,4,5,6,7,8,9,11,12,14,15,16,17-tetradecahydro-1H-cyclopenta[a]phenanthren-17-yl]-N-(2-pyrrolidin-1-ylethyl)pentanamide (108)

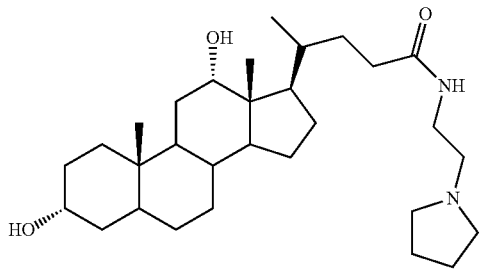 [SMILES: CC(CCC(=O)NCCN1CCCC1)[C@H]1CCC2C3CCC4C[C@H](O)CC[C@]4(C)C3C[C@H](O)[C@@]21C]

Deoxycholic acid (2.0 g 0.005 mol) was dissolved in dioxane (60 mL) with triethylamine (1.28 mL, 0.01 mol). The solution was cooled for 10 minutes in cold water. Ethyl chloroformate (0.37 mL, 0.003 mol) was then added dropwise over a ten minute period. Once added, the cold water was removed and the solution was stirred for 2 hours. After 2 hours 1-(2-aminoethyl)pyrollidine (0.77 mL, 0.006 mol) was added and the solution was stirred for 3 hours at room temperature. Water (50 mL) was then added and the solution was extracted with ethyl acetate (3×50 mL). The organic layers were combined and washed with saturated sodium hydrogen carbonate solution (3×50 mL). The organic layer was dried over magnesium sulphate. The solvent was evaporated under reduced pressure to produce a white powder.

Yield; 1.2 g, 0.0025 mol, 49%.

Melting point: 155.3-158.7° C.

$^1$H NMR (CDCl$_3$) (250 MHz) δ=0.66 (s, 3H, 18-CH$_3$), 0.89 (s, 3H, 19-CH$_3$), 0.975 (d, 3H, 21-CH$_3$, J=7.5), 1.78 (m, 4H, CH$_2$), 2.42-2.58 (m, 6H, CH$_2$), 3.35 (m, 2H, CH$_2$), 3.58 (m, 1H, 3-CH), 3.95 (broad s, 1H, 12-CH), 6.49 (broad s, 1H, NH) ppm.

$^{13}$C NMR (62.9 MHz) δ=12.7 (CH$_3$, C18), 17.5 (CH$_3$, C21), 23.3 (CH$_3$, C19), 23.7 (CH$_2$, C15), 26.1 (CH$_2$, C7), 27.1 (CH$_2$, C6), 28.6 (CH$_2$, C16), 30.4 (CH$_2$, C11), 30.5 (CH$_2$, C2), 33.3 (CH$_2$, C23), 33.6 (CH$_2$, C22), 34.1 (CH, C9), 35.2 (C, C10), 35.3 (CH$_2$, C1), 36.0 (CH, C20), 36.5 (CH$_2$, C4), 37.9 (CH, C8), 42.1 (CH$_2$), 46.5 (C, C13), 46.8 (CH, C17), 48.2 (CH, C14), 53.9 (CH), 55.0 (CH$_2$) 71.5 (CH, C3), 73.0 (CH$_2$, C12), 173.9 (CO, C24) ppm.

IR=3287 (OH), 2916 (alkyl), 2865 (alkyl), 1641 (C=O), 1539, 1441, 1040 (R$_2$CH—OH) cm$^{-1}$.

MS (+ESI) m/z=Found 489.4046 (M+H)$^+$; calculated for C$_{30}$H$_{53}$N$_2$O$_3$ 489.4051; 1 ppm.

Synthesis of 4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]-N-[2-(1-piperidyl)ethyl]pentanamide (109)

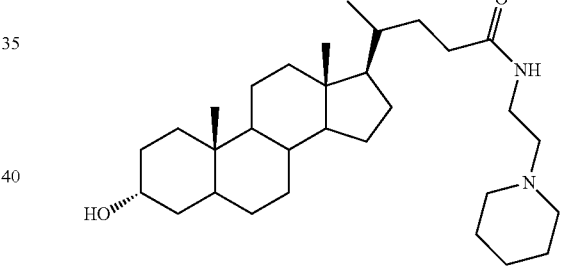

Methyl lithocholate 0.5 g (0.001 mol) 1,2 amino-ethyl piperidine 0.36 mL (0.002 mol) were heated at and stirred at 150° C. for 48 hours in a argon environment. More 1,2 amino-ethyl piperidine (1 mL, 0.007 mol) of was added and the reaction was continued under the same conditions overnight. The crude material was purified by flash column chromatography (1:1 EtOAc/MeOH) to give a solid.

Yield; 0.01 g, 0.00001 mol, 1.6%.

Melting point: 85.0-89.9° C.

$^1$H NMR CDCl$_3$ (250 MHz) δ=0.59 (s, 3H, 18-CH$_3$) 0.87-0.89 (s, 3H, 19-CH$_3$ J=5.5) 1.72 (m, 4H, CH$_2$) 2.68 (t, 2H, CH$_2$, J=5.6) 3.42-3.44 (q, 2H, CH$_2$, J=5.6) 3.58 (m, 1H, 3-CH) 7.18 (s/t, 1H, NH) ppm.

$^{13}$C NMR (62.9 MHz) δ=18.3 (CH) 23.4 (CH$_3$) 24.2 (CH$_3$CH) 26.4 (CH$_2$) 42.2 (CH$_3$) 56.5 (CH$_2$) 71.8 (COH) 173.9 (CO) ppm.

IR=3418 (NH), 3465 (OH) 2935 (alkyl), 2865 (alkyl), 1641 (C=O) cm$^{-1}$.

MS (ES) m/z=Found 487.4347 (M+H)$^+$; calculated for C$_{31}$H$_{54}$N$_2$O$_3$ 487.4264; 0.8 ppm.

Synthesis of (4R)-4-[(3R,10S,12S,13R,17R)-3,12-dihydroxy-10,13-dimethyl-2,3,4,5,6,7,8,9,11,12,14,15,16,17-tetradecahydro-1H-cyclopenta[a]phenanthren-17-yl]-N-[2-(1-piperidyl)ethyl]pentanamide (110)

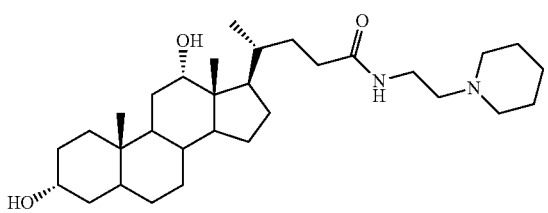 [SMILES: C[C@H](CCC(=O)NCCN1CCCCC1)[C@H]1CCC2C3CCC4C[C@H](O)CC[C@]4(C)C3C[C@H](O)[C@@]21C]

Methyl deoxycholate (1.0 g 0.002 mol) was dissolved in methanol (10 mL) with 1-(2-aminoethyl)piperidine (3.15 g, 0.024 mol) was added and the solution was stirred for 5 days. The solvent was evaporated under reduced pressure and the product was recrystallized from ethyl acetate to produce a white powder.

Yield; 0.56 g, 0.0011 mol, 45%.
Melting point: 158.5-161.1° C.
$^1$H NMR (CDCl$_3$) (250 MHz) δ=0.66 (s, 3H, 18-CH$_3$), 0.90 (s, 3H, 19-CH$_3$), 0.99 (d, 3H, 21-CH$_3$, J=5.0), 2.52 (m, 2H, CH$_2$), 3.385 (q, 2H, CH$_2$, J=5.0), 3.60 (m, 1H, 3-CH), 3.97 (s, 1H, 12-CH), 6.72 (broad s, 1H, NH) ppm.
$^{13}$C NMR (62.9 MHz) δ=12.7 (CH$_3$, C18), 17.5 (CH$_3$, C21), 23.1 (CH$_3$, C19), 23.7 (CH$_2$), 23.8 (CH$_2$) 25.2 (CH$_2$, C15), 26.1 (CH$_2$) 27.1 (CH$_2$, C7), 27.5 (CH$_2$, C6), 28.6 (CH$_2$, C16), 30.5 (CH$_2$, C2), 31.6 (CH$_2$, C23), 33.3 (CH$_2$, C22), 33.6 (CH, C9), 34.1 (C, C10), 35.2 (CH$_2$, C1), 35.2 (CH, C20), 35.4 (CH$_2$, C4), 36.0 (CH, C8), 36.5 (CH, C5), 42.0 (C, C13), 46.5 (CH, C17), 47.0 (CH$_2$) 48.3 (CH, C14), 54.2 (CH$_2$), 57.4 (CH$_2$) 71.6 (CH, C3), 73.0 (CH$_2$, C12), 173.9 (CO, C24) ppm.
IR=3300 (OH), 2925 (alkyl), 2861 (alkyl), 1642 (C=O), 1543, 1437, 1313, 1040 (R$_2$CH—OH) cm$^{-1}$.
MS (+ESI) m/z=Found 503.4202 (M+H)$^+$; calculated for C$_{31}$H$_{55}$N$_2$O$_3$ 503.4207; 1 ppm.

Synthesis of (4R)—N-(4-benzoylphenyl)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]pentanamide (111)

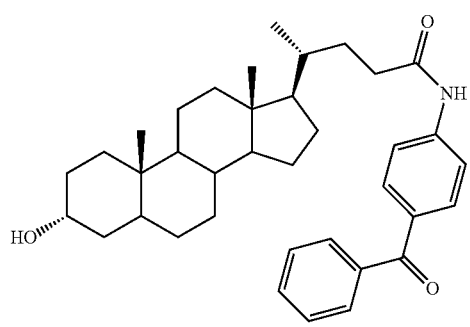 [SMILES: C[C@H](CCC(=O)Nc1ccc(C(=O)c2ccccc2)cc1)[C@H]1CCC2C3CCC4C[C@H](O)CC[C@]4(C)C3CC[C@@]21C]

Lithocholic acid (2.0 g 0.005 mol) was dissolved in tetrahydrofuran (60 mL) with N-methylmorpholine (1.07 mL, 0.01 mol). The solution was cooled for 10 minutes in cold water. Ethyl chloroformate (0.54 mL, 0.005 mol) was then added dropwise over a ten minute period. Once added, the cold water was removed and the solution was stirred for 2 hours. After 2 hours amino-benzophenone (1.5 g, 0.007 mol) was added and the solution was stirred for a further 48 hours. Water (50 mL) was then added and the solution was extracted with ethyl acetate (3×50 mL). The organic layers were combined and washed with saturated sodium hydrogen carbonate solution (3×50 mL) and 2 M hydrochloric acid solution (3×50 mL). The organic layer was dried over magnesium sulphate. The solvent was evaporated under reduced pressure and the product was triturated with ethyl acetate to produce a white powder.

Yield 0.57 g, 0.001 mol, 19%.
Melting point: 228.6-230.8° C.
$^1$H NMR (DMSO) (250 MHz) δ=0.62 (s, 3H, 18-CH$_3$) 0.87 (s, 3H, 19-CH$_3$) 0.92 (d, 2H, CH$_2$ J=7.5) 4.44 (d, 1H, 3-OH, J=5.0) 7.52-7.805 (m, 9H, Ar—CH), 10.20 (s, 1H, NH) ppm.
$^{13}$C NMR (62.9 MHz) δ=11.8 (CH$_3$, C18), 18.3 (CH$_3$, C21), 20.3 (CH$_2$, C11), 23.2 (CH$_3$, C19), 23.8 (CH$_2$, C15), 26.1 (CH$_2$, C7), 26.8 (CH$_2$, C6), 27.7 (CH$_2$, C16), 30.3 (CH$_2$, C2), 31.1 (CH$_2$, C22), 33.4 (CH$_2$, C23), 34.1 (C, C10), 34.9 (CH, C20), 35.1 (CH$_2$, C1), 35.3 (CH, C8), 41.4 (CH, C5), 42.2 (C, C13), 55.5 (CH, C17), 56.0 (CH, C14), 69.8 (CH, C3), 118.1, 128.4, 129.3, 131.0, 131.1, 132.1, 137.5, 143.5 (Ar—CH) 172.3 (CO, C24), 194.4 (CO) ppm.
IR=3488 (NH), 3249 (OH), 2925 (alkyl), 2857 (alkyl), 1675 (C=O), 1586, 1296, 1245, 1168 (C=O ester stretch), 1031 (R$_2$CH—OH) cm$^{-1}$.
MS (+ESI) m/z=Found 556.3781 (M+H)$^+$; calculated for C$_{37}$H$_{50}$NO$_3$ 556.3785; 0.8 ppm.

Synthesis of (4R)—N-(4-benzoylphenyl)-4-[(3R,10S,12S,13R,17R)-3,12-dihydroxy-10,13-dimethyl-2,3,4,5,6,7,8,9,11,12,14,15,16,17-tetradecahydro-1H-cyclopenta[a]phenanthren-17-yl]pentanamide (112)

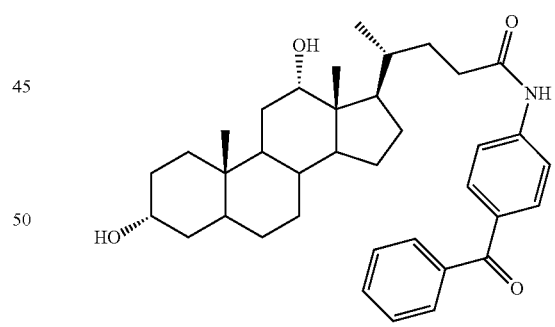

Deoxycholic acid (2.0 g 0.005 mol) was dissolved in 1, 4 dioxane (60 mL) with N-methylmorpholine (1.07 mL 0.01 mol). The solution was cooled for 10 minutes in cold water. Ethyl chloroformate (0.69 mL 0.006 mol) was then added dropwise over a ten minute period. Once added, the cold water was removed and the solution was stirred for 2 hours. After 2 hours amino-benzophenone (1.5 g 0.007 mol) was added and the solution was stirred for a further 24 hours. Water (50 mL) was then added and the solution extracted with ethyl acetate (3×50 mL). The organic layers were combined and washed with saturated sodium hydrogen carbonate solution (3×50 mL) and 2 M hydrochloric acid (3×50 mL). The organic layer was dried over magnesium sulphate. Solvent was evaporated under reduced pressure and triturated with ethyl acetate to produce a white powder.

Yield; 0.24 g, 0.0004 mol, 8%.

Melting point: 220-227.6° C.

$^1$H NMR (DMSO) (250 MHz) δ=0.60 (s, 3H, 18-CH$_3$), 0.85 (s, 3H, 19-CH$_3$), 0.97 (d, 3H, 21-CH$_3$, J=5.0), 3.80 (s, 1H, 3-CH), 4.03 (s, 1H, 12-CH), 4.21 (d, 1H, 3-OH, J=2.5), 4.46 (d, 1H, 12-OH, J=5.0), 7.52-7.79 (multiple overlapping multiplets, 9H, Ar—CH), 10.26 (s, 1H, NH) ppm.

$^{13}$C NMR (62.9 MHz) δ=12.4 (CH$_3$, C18), 17.0 (CH$_3$, C21), 23.0 (CH$_3$, C19), 26.9 (CH$_2$, C7), 27.2, (CH$_2$, C2), 32.9 (CH$_2$, C22), 33.5 (CH, C9), 33.7 (C, C10), 35.0 (CH$_2$, C1), 35.6 (CH, C20), 45.9 (C, C13), 46.1 (CH, C17), 47.2 (CH, C14), 70.9 (CH, C3), 118.1 (CH), 128.4 (CH), 129.3 (CH), 131.1 (CH), 132.1 (CH), 143.5 (CH), 172.4 (CO, C24), 194.5 (CO) ppm.

IR=3462 (OH), 2921 (alkyl), 2861 (alkyl), 1675 (C=O), 1586 (C=O), 1441, 1279, 1168.78 (C=O ester stretch), 1036 (R$_2$CH—OH) cm$^{-1}$.

MS (+ESI) m/z=Found 572.3730 (M+H)$^+$; calculated for C$_{37}$H$_{50}$NO$_4$ 572.3734; 0.8 ppm.

Synthesis of (4R)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]-1-[4-(4-pyridyl)piperazin-1-yl]pentan-1-one (113)

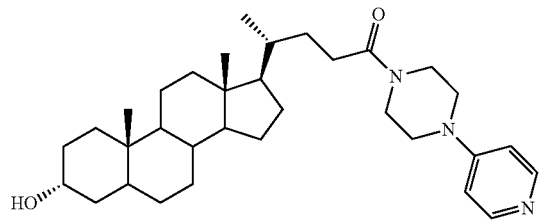 [SMILES: C[C@H](CCC(=O)N1CCN(c2ccncc2)CC1)[C@H]1CCC2C3CCC4C[C@H](O)CC[C@]4(C)C3CC[C@@]21C]

Lithocholic acid (0.5 g, 0.001 mol) was dissolved in tetrahydrofuran (15 mL) with triethylamine (0.20 mL, 0.001 mol). The solution was cooled for 10 minutes in cold water. Ethyl chloroformate (0.2 mL, 0.001 mol) was then added dropwise over a ten minute period. Once added, the cold water was removed and the solution was stirred for 2 hours. After 2 hours 1-(4-pyridyl)piperazine (0.21 mL, 0.001 mol) was added and the solution was stirred for 24 hours. Water (50 mL) was then added and the solution extracted with ethyl acetate (3×50 mL). The organic layers were combined and washed with saturated sodium hydrogen carbonate solution (3×50 mL). Due to impurities, re-dissolved in a methanol/water solution (20 mL 50/50) and extracted with chloroform (4×20 mL). The combined organic layers were dried over magnesium sulphate. The solvent was evaporated under reduced pressure to produce a white powder.

Yield; 0.03 g, 0.00005 mol, 4%.

Melting point: 150-157° C.

$^1$H NMR (CDCl$_3$) (250 MHz) δ=0.65 (s, 3H, 18-CH$_3$), 0.92 (s, 3H, 19-CH$_3$), 3.35 (m, 4H, CH$_2$), 3.64 (m, 2H, CH$_2$), 6.68 (d, 2H, Ar—CH, J=5.0), 8.31 (s, 2H, Ar—CH) ppm.

$^{13}$C NMR (62.9 MHz) δ=12.0 (CH$_3$, C18), 18.6 (CH$_3$, C21), 20.8 (CH$_2$, C11), 23.3 (CH$_3$, C19), 24.3 (CH$_2$, C15), 26.3 (CH$_2$, C7), 27.1 (CH$_2$, C6), 28.3 (CH$_2$, C16), 30.2 (CH$_2$, C2), 31.3 (CH$_2$, C22), 34.5 (C, C10), 35.4 (CH, C20), 35.8 (CH$_2$, C1), 36.4 (CH$_2$, C4), 40.1 (CH$_2$, C12), 40.4 (CH, C9), 40.7 (CH, C5), 42.1 (C, C13), 42.7 (CH$_2$), 44.7 (CH$_2$), 45.8 (CH$_2$), 45.9 (CH$_2$) 55.9 (CH, C17), 56.5 (CH, C14), 71.8 (CH, C3), 108.5 (CH), 129.7 (CH), 149.9 (CH), 150.0 (CH), 154.6 (CH), 172.7 (CO, C24) ppm.

IR=3387 (OH), 2925 (alkyl), 2852 (alkyl), 1641 (C=O), 1445, 1236, 1044, 989 (R$_2$CH—OH) cm$^{-1}$.

MS (ES) m/z=Found 522.4048 (M+H)$^+$; calculated for C$_{31}$H$_{57}$N$_2$O$_4$ 521.4313; 1.5 ppm Synthesis of (4R)—N-(4-aminobutyl)-4-[(3R,10S,12S,13R,17R)-3,12-dihydroxy-10,13-dimethyl-2,3,4,5,6,7,8,9,11,12,14,15,16,17-tetradecahydro-1H-cyclopenta[a]phenanthren-17-yl]pentanamide (114)

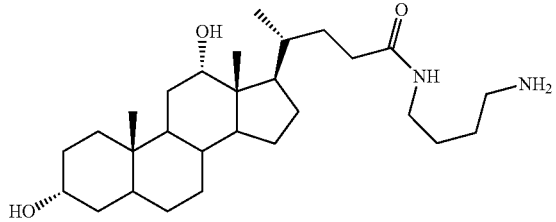 [SMILES: C[C@H](CCC(=O)NCCCCN)[C@H]1CCC2C3CCC4C[C@H](O)CC[C@]4(C)C3C[C@H](O)[C@@]21C]

Methyl deoxycholate (1.0 g 0.009 mol) was dissolved in methanol (10 mL). 1,4 Diaminobutane (2.47 mL 0.02 mol) was added and the solution was stirred for a further 72 hours. Water (50 mL) was then added and the resultant precipitate was collected by vacuum filtration, washed with water (3×20 mL) and dried under vacuum to produce a white powder.

Yield; 0.29 g, 0.0006 mol, 25%.

Melting point: 137.4-141° C.

$^1$H NMR (DMSO) (250 MHz) δ=0.58 (s, 3H, 18-CH$_3$), 0.84 (s, 3H, 19-CH$_3$), 0.91 (d, 3H, 21-CH$_3$, J=5.0), 2.99 (q, 2H, CH$_2$, J=7.5), 3.6 (m, 1H, 3-CH), 3.78 (s, 1H, 12-CH), 7.73 (broad s, 1H, NH) ppm.

$^{13}$C NMR (62.9 MHz) δ=12.4 (CH$_3$, C18), 17.0 (CH$_3$, C21), 23.0 (CH$_3$, C19), 23.4 (CH$_2$, C15), 26.0, (CH$_2$), 26.6 (CH$_2$), 26.9 (CH$_2$) 27.1 (CH$_2$, C7), 28.5 (CH$_2$, C16), 30.2 (CH$_2$, C11), 30.5 (CH$_2$, C2), 31.7 (CH$_2$, C23), 32.5 (CH$_2$, C22), 32.8 (CH, C9), 33.7 (C, C10), 35.0 (CH$_2$, C1), 35.1 (CH, C20), 35.6 (CH$_2$, C4), 36.2 (CH, C8), 41.3 (CH, C5), 41.5 (CH) 45.9 (C, C13), 46.1 (CH, C17), 47.4 (CH, C14), 69.8 (CH, C3), 69.8 (CH$_2$, C12), 172.2 (CO, C24)v ppm.

IR=3322 (OH), 2929 (alkyl), 2857 (alkyl), 1624 (C=O), 1539, 1437, 1360, 1040 (R$_2$CH—OH) cm$^{-1}$.

MS (+ESI) m/z=Found 463.3886 (M+H)$^+$; calculated for C$_{28}$H$_{51}$N$_2$O$_3$ 463.3894; 1.8 ppm.

Synthesis of (4R)—N-[2-[2-(2-aminoethoxy)ethoxy]ethyl]-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]pentanamide (115)

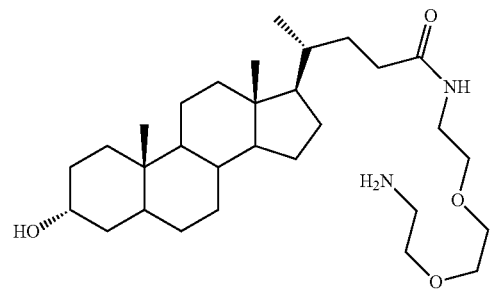 [SMILES: C[C@H](CCC(=O)NCCOCCOCCN)[C@H]1CCC2C3CCC4C[C@H](O)CC[C@]4(C)C3CC[C@@]21C]

Lithocholic acid (2.0 g, 0.005 mol) was dissolved in toluene (40 mL). 2, 2'-(ethylenedioxy)bis(ethylamine) (7.8 mL, 0.052 mol) was added and the solution was heated at reflux for 5 days. Water (50 mL) was then added and resultant precipitate collected by vacuum filtration, with further washes of water (3×20 mL). The product was dried under vacuum to produce an off-white powder.

Yield, 1.62 g, 0.003 mol, 60.22%

Melting point: 81.1-85.5° C.

$^1$H NMR (CDCl$_3$) (250 MHz) δ=0.64 (s, 3H, 18-CH$_3$), 0.92 (s, 3H, 19-CH$_3$), 2.91 (broad s, 2H, CH$_2$), 3.46-3.63 (multiple overlapping multiplets, 10H, CH$_2$), 6.24 (broad s, 1H, NH) ppm.

$^{13}$C NMR (62.9 MHz) δ=12.0 (CH$_3$, C18), 18.4 (CH$_3$, C21), 19.9 (CH$_2$) 20.8 (CH$_2$, C11), 23.3 (CH$_3$, C19), 24.2 (CH$_2$, C15), 26.4 (CH$_2$, C7), 27.2 (CH$_2$, C6), 28.2 (CH$_2$, C16), 30.5 (CH$_2$, C2), 31.7 (CH$_2$, C22), 33.4 (CH$_2$, C23), 34.5 (C, C10), 35.3 (CH, C20), 35.5 (CH$_2$, C1), 35.8 (CH, C8), 36.4 (CH$_2$, C4), 39.0 (CH$_2$, C12), 39.1 (CH, C9), 40.2 (CH$_2$), 40.4 (CH$_2$) 42.1 (CH, C5), 42.7 (C, C13), 56.0 (CH, C17), 56.5 (CH, C14), 70.1 (CH$_2$), 70.5 (CH, C3), 71.7 (CH$_2$), 173.7 (CO, C24) ppm.

IR=3356 (OH), 2921 (alkyl), 2857 (alkyl), 1641 (C═O), 1552, 1441, 1300, 1104 (C═O ester stretch), 1053 (R$_2$CH—OH) cm$^{-1}$.

MS (+ESI) m/z=Found 507.4149 (M+H)$^+$; calculated for C$_{30}$H$_{55}$N$_2$O$_4$ 507.4156; 1.4 ppm.

Synthesis of (4R)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]-N-[2-[2-[2-(2 methylprop-2-enoylamino)ethoxy]ethoxy]ethyl]pentanamide (116)

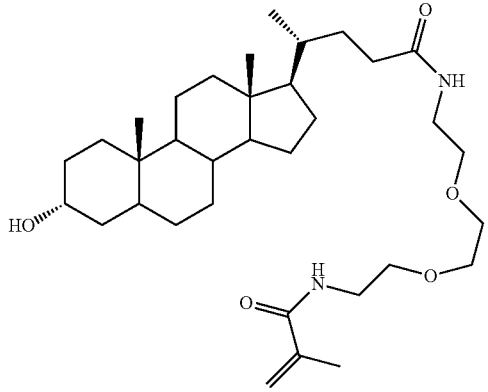 [SMILES: C=C(C)C(=O)NCCOCCOCCNC(=O)CC[C@@H](C)[C@H]1CCC2C3CCC4C[C@H](O)CC[C@]4(C)C3CC[C@@]21C]

Compound 115 (0.5 g 0.0009 mol) was dissolved in anhydrous tetrahydrofuran (10 mL) with triethylamine (0.20 mL, 0.001 mol). Methacrylic anhydride (0.30 mL, 0.0018) was then added. The solution was stirred for 48 hours, protected from sunlight by tin foil at ambient room temperature. Water (30 mL) was then added and the resulting precipitate was collected by vacuum filtration, washed with water (3×20 mL) and dried under vacuum.

Yield; 0.07 g, 0.0001 mol, 12.5%.

Melting point: 57.3-59.0° C.

$^1$H NMR (DMSO) (250 MHz) δ=0.60 (s, 3H, 18-CH$_3$), 0.87 (s, 3H, 19-CH$_3$), 1.84 (s, 3H, acryloyl-CH$_3$), 3.154-3.50 (m, 13H, CH/CH$_2$), 4.42 (d, 1H, 3-OH, J=5.0), 5.31 (s, 1H, ═CH), 5.64 (s, 1H, ═CH), 7.78 (broad s, 1H, NH), 7.91 (broad s, 1H, NH) ppm.

$^{13}$C NMR (62.9 MHz) δ=11.8 (CH$_3$, C18), 18.2 (CH$_3$, C21), 18.6 (CH), 20.3 (CH$_2$, C11), 23.2 (CH$_3$, C19), 23.8 (CH$_2$, C15), 26.1 (CH$_2$, C7), 26.8 (CH$_2$, C6), 27.7 (CH$_2$, C16), 30.3 (CH$_2$, C2), 31.5 (CH$_2$, C22), 32.2 (CH$_2$, C23), 34.1 (C, C10), 34.9 (CH, C20), 35.1 (CH$_2$, C1), 35.3 (CH, C8), 41.4 (CH, C5), 42.2 (C, C13), 55.2 (CH, C17), 56.0 (CH, C14), 68.8 (CH$_2$), 69.1 (CH$_2$), 69.5 (CH$_2$), 69.8 (CH, C3), 118.9 (CH$_2$), 139.8 (CH$_2$), 167.4 (CO) 172.5 (CO, C24) ppm.

IR=3415 (NH), 3292 (OH), 2933 (alkyl), 2861 (alkyl), 1658 (C═O), 1590 (C═O), 1394, 1249 (C═O ester stretch), 1036 (R$_2$CH—OH) cm$^{-1}$.

MS (+ESI) m/z=Found 575.4412 (M+H)$^+$; calculated for C$_{34}$H$_{59}$N$_2$O$_5$ 575.4418; 1.1 ppm.

Synthesis of (4R)—N-(4-acetylphenyl)-4-[(3R,10S,12S,13R,17R)-3,12-dihydroxy-10,13-dimethyl-2,3,4,5,6,7,8,9,11,12,14,15,16,17-tetradecahydro-1H-cyclopenta[a]phenanthren-17-yl]pentanamide (117)

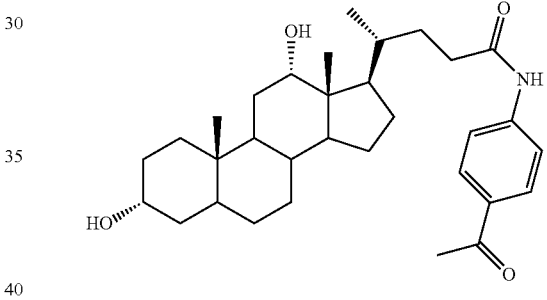

Deoxycholic acid (2.0 g 0.005 mol) was dissolved in 1, 4 dioxane (60 mL) with triethylamine (1.32 mL, 0.01 mol). The solution was cooled for 10 minutes in cold water. Ethyl chloroformate (0.40 mL, 0.003 mol) was then added dropwise over a ten minute period. Once added, the cold water was removed and the solution was stirred for 2 hours. After 2 hours 4'-aminoacetophenone (0.75 g, 0.005 mol) was added and the solution was stirred for a further 48 hours. Water (50 mL) was then added and the resulting precipitate was collected by vacuum filtration. The crude product was triturated with ethyl acetate to produce a white powder.

Yield; 0.65 g, 0.001 mol, 25%.

$^1$H NMR (DMSO) (250 MHz) δ=0.62 (s, 3H, 18-CH$_3$), 0.86 (s, 3H, 19-CH$_3$), 2.52 (s, 3H, ketone-CH$_3$), 3.81 (broad s, 1H, 12-CH), 4.21 (d, 1H, 3-OH, J=2.5), 4.46 (d, 1H, 12-OH, J=2.5), 7.73 (d, 2H, Ar—CH, J=10.0), 7.92 (d, 2H, Ar—CH, J=7.5), 10.21 (s, 1H, NH) ppm.

IR=3475 (OH), 2921 (alkyl), 2861 (alkyl), 1684 (C═O), 1646 (C═O), 1594, 1539, 1407, 1044 (C═O ester stretch) cm$^{-1}$.

MS (+ESI) m/z=Found 510.3570 (M+H)$^+$; calculated for C$_{32}$H$_{48}$NO$_4$ 510.3578; 1.3 ppm.

Synthesis of ethane; (4R)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]-1-[4-(2-hydroxyethyl)piperazin-1-yl]pentan-1-one (118)

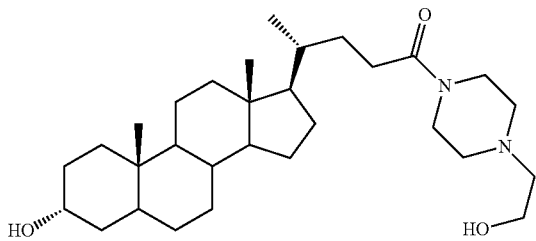 [SMILES: C[C@H](CCC(=O)N1CCN(CCO)CC1)[C@H]1CCC2C3CCC4C[C@H](O)CC[C@]4(C)C3CC[C@@]21C]

Lithocholic acid (4.0 g 0.01 mol) was dissolved in tetrahydrofuran (120 mL) with triethylamine (1.30 mL, 0.01 mol). The solution was cooled for 10 minutes in cold water. Ethyl chloroformate (1.02 mL, 0.009 mol) was then added dropwise over a ten minute period. Once added, the cold water was removed and the solution was stirred for 2 hours. After 2 hours 1-(2-hydroxyethylpiperazine) (1.5 mL, 0.01 mol) was added and the solution was stirred for a further 48 hours. Water (50 mL) was then added and the solution was extracted with ethyl acetate (3×50 mL). The organic layers were combined and washed with saturated sodium hydrogen carbonate solution (3×50 mL). The organic layer was dried over magnesium sulphate. The solvent was evaporated under reduced pressure and the product was recrystallized from ethyl acetate to produce a white powder.

Yield; 2.27 g, 0.004 mol, 43%.
Melting point: 153.0-154.8° C.
$^1$H NMR (CDCl$_3$) (250 MHz) δ=0.65 (s, 3H, 18CH$_3$), 0.92 (s, 3H, 19-CH$_3$), 2.50 (m, 4H, CH$_2$), 2.58 (t, 2H, CH$_2$, J=5.0), 3.49 (t, 2H, CH$_2$, J=2.5), 3.65 (t, 4H, CH$_2$, J=5.0) ppm.
$^{13}$C NMR (62.9 MHz) δ=12.0 (CH$_3$, C18), 18.5 (CH$_3$, C21), 20.8 (CH$_2$, C11), 23.3 (CH$_3$, C19), 24.2 (CH$_2$, C15), 26.4 (CH$_2$, C7), 27.2 (CH$_2$, C6), 28.2 (CH$_2$, C16), 30.2 (CH$_2$, C2), 30.5 (CH$_2$, C22), 31.4 (CH$_2$, C23), 34.5 (C, C10), 35.3 (CH, C20), 35.6 (CH$_2$, C1), 35.8 (CH, C8), 36.4 (CH$_2$, C4), 40.2 (CH$_2$, C12), 40.4 (CH, C9), 41.4 (CH, C5), 42.1 (C, C13), 42.7 (CH$_2$), 45.6 (CH$_2$), 52.6 (CH$_2$), 53.1 (CH$_2$) 56.0 (CH, C17), 56.5 (CH, C14), 57.7 (CH$_2$), 59.3 (CH$_2$) 71.8 (CH, C3), 172.1 (CO, C24) ppm.
IR=3381 (OH), 2916 (alkyl), 2840 (alkyl), 1620 (C=O), 1445, 1258, 1044 (R$_2$CH—OH) cm$^{-1}$.
MS (ES) m/z=Found 489.4045 (M+H)$^+$; calculated for C$_{30}$H$_{53}$N$_2$O$_3$ 489.4051; 1.2 ppm.

Synthesis of (4R)-4-[(3R,10S,12S,13R,17R)-3,12-dihydroxy-10,13-dimethyl-2,3,4,5,6,7,8,9,11,12,14,15,16,17-tetradecahydro-1H-cyclopenta[a]phenanthren-17-yl]-1-[4-(2-hydroxyethyl)piperazin-1-yl]pentan-1-one (119)

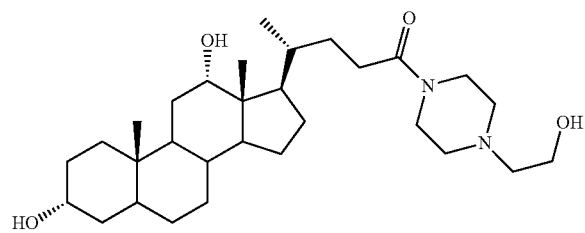 [SMILES: C[C@H](CCC(=O)N1CCN(CCO)CC1)[C@H]1CCC2C3CCC4C[C@H](O)CC[C@]4(C)C3C[C@H](O)[C@@]21C]

Deoxycholic acid (4.0 g 0.01 mol) was dissolved in 1, 4 dioxane (120 mL) with triethylamine (2.70 mL 0.02 mol). The solution was cooled for 10 minutes in cold water. Ethyl chloroformate (0.8 mL 0.005 mol) was then added dropwise over a ten minute period. Once added, the cold water was removed and the solution was stirred for 2 hours. After 2 hours 1-(2-hydroxyethylpiperazine) (1.32 mL 0.01 mol) was added and the solution was stirred for 48 hours. Water (50 mL) was then added and the solution extracted with ethyl acetate (3×50 mL). The organic layers were combined and washed with saturated sodium hydrogen carbonate solution (3×50 mL). The organic layer was dried over magnesium sulphate. Solvent was evaporated under reduced pressure and recrystallized from methanol to produce a white powder.

Yield; 2.41 g, 0.004 mol, 46.8%.
Melting point: 241.0-243.9° C.
$^1$H NMR (CDCl$_3$/MeOH) (250 MHz) δ=0.70 (s, 3H, 18-CH$_3$), 0.93 (s, 3H, 19-CH$_3$), 2.58 (multiple overlapping multiplets, 6H, CH$_2$), 3.53 (broad t, 3H, 3-CH/CH$_2$), 3.65-3.72 (multiple overlapping multiplets, 4H, CH$_2$), 3.96 (broad s, 1H, 12-CH) ppm.
IR=3407 (OH), 2929 (alkyl), 1620 (C=O), 1454, 1215, 1044 (R$_2$CH—OH) cm$^{-1}$.
MS (+ESI) m/z=Found 505.3994 (M+H)$^+$; calculated for C$_{31}$H$_{57}$N$_2$O$_4$ 505.4000; 1.2 ppm.

Synthesis of (4R)—N-[3-(dibutylamino)propyl]-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]pentanamide (120)

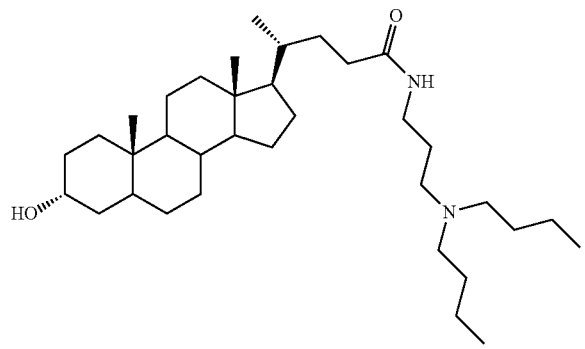 [SMILES: CCCCN(CCCC)CCCNC(=O)CC[C@@H](C)[C@H]1CCC2C3CCC4C[C@H](O)CC[C@]4(C)C3CC[C@@]21C]

Lithocholic acid (0.5 g 0.001 mol) was dissolved in tetrahydrofuran (15 mL) with triethylamine (0.20 mL 0.001 mol). The solution was cooled for 10 minutes in cold water. Ethyl chloroformate (0.2 mL 0.001 mol) was then added dropwise over a ten minute period. Once added, the cold water was removed and the solution was stirred for 2 hours. After 2 hours 3-(dibutylamino)-1-propylamine (0.25 mL, 0.001 mol) was added and the solution was stirred for 24 hours. Water (50 mL) was then added and the solution extracted with ethyl acetate (3×50 mL). The organic layers were combined and washed with saturated sodium hydrogen carbonate solution (3×50 mL). This crude material was further purified using column chromatography (8:2 ethyl acetate/methanol). The compound containing fractions were dried over magnesium sulphate. Solvent was evaporated under reduced pressure to produce a white powder.

Yield; 0.24 g, 0.0004 mol, 33%.
Melting point: 62.9-69.3° C.

¹H NMR (CDCl₃) (250 MHz) δ=0.64 (s, 3H, 18-CH₃), 0.93 (s, 3H, 19-CH₃), 0.94 (m, 6H, CH₃), 1.35 (m, 8H, CH₂), 2.45 (t, 4H, CH₂, J=5.0), 3.32 (q, 2H, CH₂, J=5.0), 7.51 (broad s, 1H, NH) ppm.

¹³C NMR (62.9 MHz) δ=12.0 (CH₃, C18), 14.0 (CH), 18.3 (CH₃, C21), 20.7 (CH₂, C11), 23.3 (CH₃, C19), 24.2 (CH₂, C15), 25.1 (CH₂), 26.4 (CH₂, C7), 27.2 (CH₂, C6), 28.2 (CH₂, C16), 28.4 (CH₂), 28.5 (CH₂) 30.4 (CH₂, C2), 30.5 (CH₂, C22), 33.8 (CH₂, C23), 34.5 (C, C10), 35.3 (CH, C20), 36.4 (CH₂, C1), 39.4 (CH₂, C4), 40.1 (CH₂, C12), 40.4 (CH, C9), 42.0 (CH, C5), 42.1 (C, C13), 42.7 (CH₂) 56.1 (CH, C17), 56.4 (CH, C14), 71.6 (CH, C3), 173.6 (CO, C24) ppm.

IR=3296 (OH), 2916 (alkyl), 2861 (alkyl), 1650 (C=O), 1548, 1441, 1377, 1070, 1066, 1036 (R₂CH—OH) cm⁻¹.

MS (+ESI) m/z=Found 545.5032 (M+H)⁺; calculated for C₃₅H₆₅N₂O₂ 545.5041; 1.6 ppm.

Synthesis of (4R)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]-N-octadecyl-pentanamide (121)

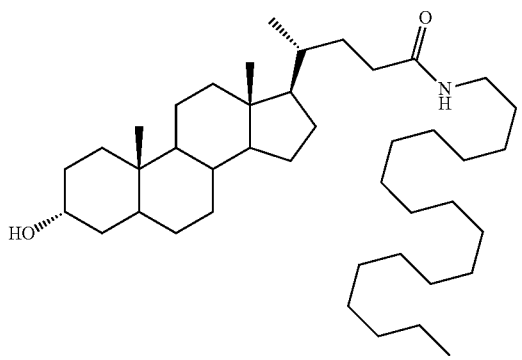 [SMILES: CCCCCCCCCCCCCCCCCCNC(=O)CC[C@@H](C)[C@H]1CCC2C3CCC4C[C@H](O)CC[C@]4(C)C3CC[C@@]21C]

Lithocholic acid (2.0 g 0.005 mol) was dissolved in tetrahydrofuran (60 mL) with 4-methylmorpholine (2.14 mL, 0.02 mol). The solution was cooled for 10 minutes in cold water. Ethyl chloroformate (0.51 mL, 0.005 mol) was then added dropwise over a ten minute period. Once added, the cold water was removed and the solution was stirred for 2 hours. After 2 octadecylamine (1.43 mL, 0.005 mol) was added and the solution was stirred for a further 21 hours. Water (50 mL) was then added and the solution was extracted with ethyl acetate (3×50 mL). The crude product was purified by column chromatography (100% ethyl acetate). The product containing fractions were dried over magnesium sulphate. The solvent was evaporated under reduced pressure to produce a white powder.

Yield; 0.8 g, 0.001 mol, 23.9%.

Melting point: 94.8-95.4° C.

¹H NMR (250 MHz) CDCl₃ δ=0.64 (s, 3H, 18-CH₃), 0.92 (s, 3H, 19-CH₃), 1.25 (s, 30H, aliphatic CH₂) 3.23 (q, 3H, chain terminal CH₃, J=5.0), 3.64 (m, 1H, 3-CH), 5.36 (broad s, 1H, NH) ppm.

¹³C NMR (62.9 MHz) δ=12.0 (CH₃, C18), 18.4 (CH₃, C21), 20.8 (CH₂, C11), 22.7 (CH₃, C19), 23.3 (CH₂, C15), 24.2 (CH₂) 26.4 (CH₂, C7), 26.9 (CH₂, C6), 27.2 (CH₂, C16), 28.2 (CH₂), 29.3 (CH₂), 29.5 (CH₂), 29.7 (CH₂), 30.5 (CH₂, C2), 31.8 (CH₂, C22), 29.3 (CH₂, C23), 33.7 (C, C10), 35.3 (CH, C20), 35.4 (CH₂, C1), 35.8 (CH, C8), 39.5 (CH₂, C4), 40.2 (CH₂, C12), 40.4 (CH, C9), 42.1 (C, C5), 56.0 (CH, C17), 56.5 (CH, C14), 71.9 (CH, C3), 185.3 (CO, C24) ppm.

IR=3411 (NH), 3325 (OH), 2912 (alkyl), 2849 (alkyl), 1653 (C=O), 1544, 1464, 1367, 1308, 1040 (R₂CH—OH) cm⁻¹.

MS (+ESI) m/z=Found 628.6205 (M+H)⁺; calculated for C₄₂H₇₈NO₂ 628.6207; 0.6 ppm.

Synthesis of (4R)-4-[(3R,10S,12S,13R,17R)-3,12-dihydroxy-10,13-dimethyl-2,3,4,5,6,7,8,9,11,12,14,15,16,17-tetradecahydro-1H-cyclopenta[a]phenanthren-17-yl]-N-octadecyl-pentanamide (122)

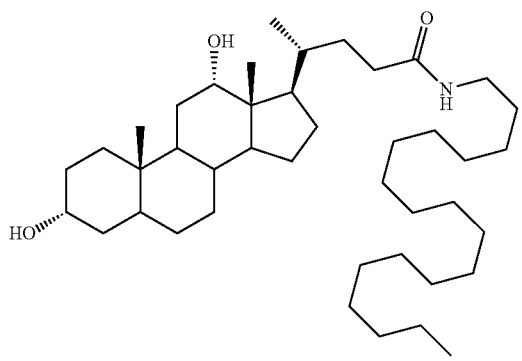 [SMILES: CCCCCCCCCCCCCCCCCCNC(=O)CC[C@@H](C)[C@H]1CCC2C3CCC4C[C@H](O)CC[C@]4(C)C3C[C@H](O)[C@@]21C]

Deoxycholic acid (2.0 g 0.005 mol) was dissolved in 1, 4 dioxane (60 mL) with triethylamine (1.32 mL, 0.01 mol). The solution was cooled for 10 minutes in cold water. Ethyl chloroformate (0.40 mL, 0.003 mol) was then added dropwise over a ten minute period. Once added, the cold water was removed and the solution was stirred for 2 hours. After 2 hours octadecylamine (1.37 g, 0.005 mol) was added and the solution was stirred for a further 48 hours. Water (50 mL) was then added and the solution was extracted with ethyl acetate (3×50 mL). The organic layers were combined and washed with saturated sodium hydrogen carbonate solution (3×50 mL). The organic layer was dried over magnesium sulphate. The solvent was evaporated under reduced pressure and the product was recrystallized from ethyl acetate to produce a transparent glass-like solid.

Yield; 2.32 g, 0.003 mol, 70%.

Melting point: 54.2-57.3° C.

¹H NMR (CDCl₃) (250 MHz) δ=0.68 (s, 3H, 18-CH₃), 0.91 (s, 3H, 19-CH₃), 1.25 (s, 32H, aliphatic CH₂) 3.22 (q, 2H, CH₂, J=7.5), 3.61 (m, 1H, 3-CH), 3.98 (1H, 12-CH), 5.53 (broad s, 1H, NH) ppm.

¹³C NMR (62.9 MHz) δ=12.7 (CH₃, C18), 14.1 (CH₂), 17.4 (CH₃, C21), 22.6 (CH₂), 23.1 (CH₃, C19), 23.6 (CH₂, C15), 26.1 (CH), 26.9 (CH₂, C7), 28.6 (CH₂, C16), 29.3 (CH₂, C11), 29.5 (CH₂, C2), 29.7 (CH₂), 30.5 (CH) 31.7 (CH₂, C23), 31.9 (CH₂, C22), 33.5 (CH, C9), 33.6 (CH), 34.1 (CH), 35.2 (C, C10), 35.2 (CH) 36.0 (CH₂, C1), 36.4 (CH, C20), 39.5 (CH₂, C4), 42.1 (CH, C5), 46.5 (C, C13), 47.2 (CH, C17), 48.2 (CH, C14), 71.7 (CH, C3), 73.1 (CH₂, C12), 173.4 (CO, C24) ppm.

IR=3292 (OH), 2912, 2852 (alkyl), 1637 (C=O), 1548, 1189.78 (C=O ester stretch), 1036 (RCHOH) cm⁻¹.

MS (+ESI) m/z=Found 644.5971 (M+H)⁺; calculated for C₄₂H₇₈NO₃ 644.5976; 0.8 ppm.

Synthesis of 2-[[(4R)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]pentanoyl]amino]ethyl-trimethyl-ammonium iodide (123)

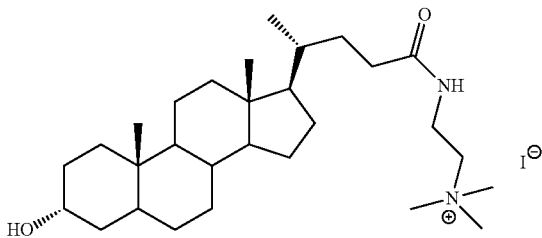 [SMILES: C[C@H](CCC(=O)NCC[N+](C)(C)C)[C@H]1CCC2C3CCC4C[C@H](O)CC[C@]4(C)C3CC[C@@]21C ; [I-]]

Compound 101 (0.2 g 0.0004 mol) was dissolved in chloroform (10 mL) with Iodomethane (0.31 mL 0.002 mol). The solution was left overnight at which point a precipitate had formed which was collected by vacuum filtration, washed with water (3×20 mL) and dried under vacuum to produce a white powder.

Yield; 0.212 g, 0.0003 mol, 81.5%.

Melting point: 212.8-216.1° C.

$^1$H NMR (MeOD) (250 MHz) δ=0.69, (s, 3H, 18-CH$_3$), 0.94 (s, 3H, 19-CH$_3$), 3.19, (s, 9H, 3×CH$_3$), 3.45 (q, 2H, CH$_2$, J=7.5), 3.55 (m, 1H, 3-CH), 3.64 (t, 2H, CH$_2$, J=7.5) ppm.

$^{13}$C NMR (62.9 MHz) δ=11.0 (CH$_3$), 12.5 (CH$_3$), 17.3 (CH$_3$), 18.8 (CH$_2$), 21.9 (CH) 23.9 (CH$_2$), 27.6 (CH), 28.3 (CH), 31.2 (CH), 33.0 (CH), 33.9 (CH), 36.9 (CH$_2$), 37.2 (CH$_2$), 41.9 (CH), 43.5 (C, C13), 57.4 (CH, C17), 57.9 (CH, C14), 65.8 (CH$_2$) 72.4 (CH), 181.2 (CO) ppm.

IR=3368 (NH), 3245 (OH), 2938 (alkyl), 2852 (alkyl) 1639 (C=O), 1560, 1441, 1258 (C=O ester stretch), 1040 (R$_2$CH—OH) cm$^{-1}$.

MS (+ESI) m/z=Found 461.4105 M$^+$; calculated for C$_{29}$H$_{53}$N$_2$O$_2$ 461.4102; 0.7 ppm.

Synthesis of 2-[[(4R)-4-[(3R,10S,12S,13R,17R)-3,12-dihydroxy-10,13-dimethyl-2,3,4,5,6,7,8,9,11,12,14,15,16,17-tetradecahydro-1H-cyclopenta[a]phenanthren-17-yl]pentanoyl]amino]ethyl-trimethyl-ammonium iodide (124)

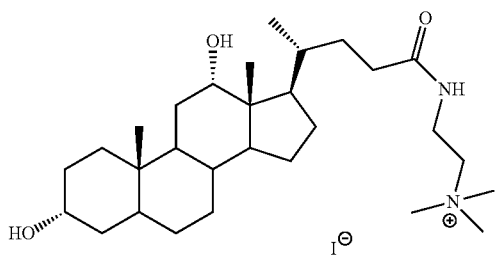 [SMILES: C[C@H](CCC(=O)NCC[N+](C)(C)C)[C@H]1CCC2C3CCC4C[C@H](O)CC[C@]4(C)C3C[C@H](O)[C@@]21C ; [I-]]

Compound 102 (0.15 g 0.0003 mol) was dissolved in chloroform (5 mL). Iodomethane (0.22 mL, 0.001 mol) was added and the solution was stirred overnight at ambient temperature. The resultant precipitate was collected via vacuum filtration and dried in a desiccator overnight to give the product as an off-white solid.

Yield 0.09 g, 0.0001 mol, 78.9%.

Melting point: 160.1-169.1° C.

$^1$H NMR (MeOD) (250 MHz) δ=0.70 (s, 3H, 18-CH$_3$), 0.93 (s, 3H, 19-CH$_3$), 1.02 (d, 3H, 21-CH$_3$, J=5.0), 3.20 (s, 9H, 3×CH$_3$), 3.47 (t, 2H, CH$_2$, J=7.5), 3.64 (t, 2H, CH$_2$, J=5.0), 3.95 (s, 1H, 12-CH) ppm.

$^{13}$C NMR (62.9 MHz) δ=13.2 (CH$_3$, C18), 17.6 (CH$_3$, C21), 23.7 (CH$_3$, C19), 24.8 (CH$_2$, C15), 27.4 (CH$_2$, C7), 28.4 (CH$_2$, C6), 28.7 (CH$_2$, C16), 29.9 (CH$_2$, C11), 31.0 (CH$_2$, C2), 33.0 (CH$_2$, C23), 33.8 (CH$_2$), 34.6 (CH$_2$), 36.4 (CH$_2$, C1), 36.8 (CH, C20), 37.2 (CH$_2$, C4), 37.4 (CH, C8), 43.6 (CH, C5), 54.0 (CH), 54.0 (CH), 54.1 (CH), 72.5 (CH, C3), 74.0 (CH$_2$, C12), 177.3 (CO, C24) ppm.

IR=3377 (NH), 3249 (OH), 2921 (alkyl), 2861 (alkyl), 1641 (C=O), 1573, 1454, 1373, 1249, 1031 (R$_2$CH—OH) cm$^{-1}$.

MS (+ESI) m/z=Found 477.4060 M$^+$; calculated for C$_{29}$H$_{53}$N$_2$O$_3$ 477.4051; 1.9 ppm.

Synthesis of ethyl-[3-[[(4R)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]pentanoyl]amino]propyl]-dimethyl-ammonium iodide (125)

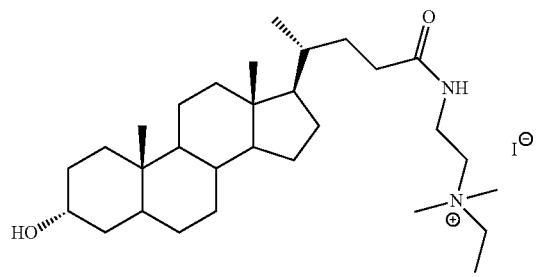 [SMILES: CC[N+](C)(C)CCNC(=O)CC[C@@H](C)[C@H]1CCC2C3CCC4C[C@H](O)CC[C@]4(C)C3CC[C@@]21C ; [I-]]

Compound 101 (0.2 g 0.0004 mol) was dissolved in chloroform (10 mL). Ethyl Iodide (0.34 mL, 0.001 mol) was added and the solution was stirred overnight at ambient temperature. The resulting precipitate was collected by vacuum filtration and was dried overnight in a desiccator to give the product as an off-white solid.

Yield; 0.2 g, 0.0003 mol, 76%.

Melting point: 120.0-123.0° C.

$^1$H NMR (MeOD) (250 MHz) δ=0.69 (s, 3H, 18-CH$_3$), 0.95 (s, 3H, 19-CH$_3$), 3.13 (s, 6H, 2×CH$_3$), 3.43 (m, 4H, 3-CH/CH$_2$), 3.60 (q, 2H, CH$_2$, J=7.5) ppm.

$^{13}$C NMR (62.9 MHz) δ=8.4 (CH) 12.5 (CH$_3$, C18), 18.8 (CH$_3$, C21), 21.4 (CH$_2$, C11), 21.9 (CH$_3$, C19), 23.9 (CH$_2$, C15), 25.2 (CH$_2$, C7), 28.3 (CH$_2$, C16), 29.3 (CH$_2$, C2), 31.2 (CH$_2$, C23), 33.0 (CH$_2$), 33.9 (CH$_2$), 34.2 (C, C10), 35.6 (CH, C20), 36.4 (CH$_2$, C1), 37.1 (CH, C8), 37.2 (CH$_2$, C4), 41.5 (CH, C9), 41.9 (CH, C5), 43.5 (C, C13), 43.9 (CH$_2$), 51.1 (CH$_2$) 57.3 (CH, C17), 57.9 (CH, C14), 62.4 (CH) (CH, C3), 177.3 (CO, C24) ppm.

IR=3373 (OH), 2942 (alkyl), 2844 (alkyl), 1646 (C=O), 1441, 1270, 1036 (R$_2$CH—OH) cm$^{-1}$.

MS (+ESI) m/z=Found 475.4247 M$^+$; calculated for C$_{30}$H$_{55}$N$_2$O$_2$ 475.4258; 2.3 ppm.

Synthesis of 3-[[(4R)-4-[(3R,10S,12S,13R,17R)-3,12-dihydroxy-10,13-dimethyl-2,3,4,5,6,7,8,9,11,12,14,15,16,17-tetradecahydro-1H-cyclopenta[a]phenanthren-17-yl]pentanoyl]amino]propyl-ethyl-dimethyl-ammonium iodide (126)

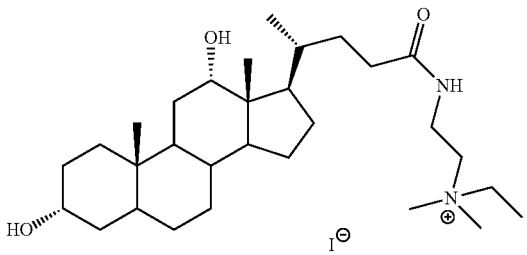 [SMILES: CC[N+](C)(C)CCNC(=O)CC[C@@H](C)[C@H]1CCC2C3CCC4C[C@H](O)CC[C@]4(C)C3C[C@H](O)[C@@]21C ; [I-]]

Compound 102 (0.2 g 0.0004 mol) was dissolved in chloroform (5 mL). Ethyl Iodide (0.62 mL, 0.003 mol) was added and the solution was stirred overnight at ambient temperature. The resulting precipitate was collected by vacuum filtration and was dried overnight in a desiccator. The product was an off-white solid.

Yield; 0.13 g, 0.0002 mol, 52%.
Melting point: 115.3-120.3° C.
$^1$H NMR (CDCl$_3$) (250 MHz) δ=0.70 (s, 3H, 18-CH$_3$), 0.93 (s, 3H, 19-CH$_3$), 1.02 (d, 2H, CH$_2$), 2.21 (m, 6H, 3-CH/CH$_2$), 3.4 (broad s, 2H, CH$_2$), 3.45-3.61 (multiple overlapping multiplets, 8H, CH$_2$) ppm.
$^{13}$C NMR (62.9 MHz) δ=8.4 (CH$_2$) 12.4 (CH$_3$, C18), 16.9 (CH$_3$, C21), 21.9 (CH$_2$) 22.9 (CH$_3$, C19), 24.0 (CH$_2$, C15), 26.6 (CH$_2$, C7), 27.9 (CH$_2$, C16), 29.1 (CH$_2$, C11), 30.3 (CH$_2$, C2), 32.2 (CH$_2$, C23), 33.1 (CH$_2$, C22), 34.0 (CH, C9), 34.5 (C, C10), 35.6 (CH$_2$, C1), 36.0 (CH, C20), 36.4 (CH$_2$, C4), 36.6 (CH, C8), 42.8 (CH, C5), 55.6 (CH), 57.1 (CH), 63.2 (CH) 71.7 (CH, C3), 73.2 (CH$_2$, C12), 176.6 (CO, C24) ppm.
IR=3368 (NH), 3253 (OH), 2921 (alkyl), 2852 (alkyl), 1650 (C=O), 1522, 1445, 1364, 1253, 1036 (R$_2$CH—OH) cm$^{-1}$.
MS (+ESI) m/z=Found 517.4354 M$^+$; calculated for C$_{32}$H$_{57}$N$_2$O$_3$ 517.4364; 1.9 ppm.

Synthesis of allyl-[2-[[(4R)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]pentanoyl]amino]ethyl]-dimethyl-ammonium bromide (127)

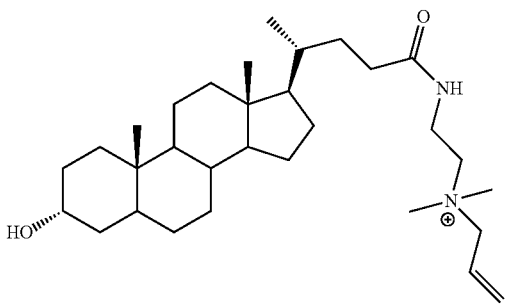

Compound 101 (0.2 g, 0.0004 mol) was dissolved in a solution of chloroform (10 mL). Allyl bromide (0.27 mL, 0.002 mol) was added and the solution was stirred overnight at which point a precipitate was formed. The precipitate was collected by vacuum filtration and was dried overnight in a desiccator. The product was an off-white solid.

Yield; 0.13 g, 0.0002 mol, 54%.
Melting point: 198.7-203.8° C.
$^1$H NMR (MeOD) (250 MHz) δ=0.68 (s, 3H, 18-CH$_3$), 0.94 (s, 3H, 19-CH$_3$), 3.12 (s, 6H, 2×CH$_3$), 3.39 (t, 2H, CH$_2$), 3.65 (t, 2H, CH$_2$), 5.70 (m, 2H, CH$_2$), 6.10 (m, 1H, =CH—) ppm.
$^{13}$C NMR (62.9 MHz) δ=12.5 (CH$_3$, C18), 18.8 (CH$_3$, C21), 21.9 (CH$_2$, C11), 23.9 (CH$_3$, C19), 25.2 (CH$_2$, C15), 27.6 (CH$_2$, C7), 28.3 (CH$_2$), 28.0 (CH$_2$, C16), 33.0 (CH$_2$) 34.2 (C, C10), 37.1 (CH$_2$), 41.5 (CH$_2$), 41.9 (CH$_2$), 43.8 (CH), 57.3 (CH$_2$), 57.9 (CH$_2$), 63.0 (CH$_2$), 72.4 (CH, C3), 126.0 (CH), 129.8 (CH), 177.3 (CO, C24) ppm.
IR=3266 (OH), 2929 (alkyl), 2848 (alkyl), 1646 (C=O), 1569, 1420, 1066, 1036 (R$_2$CH—OH) cm$^{-1}$.
MS (+ESI) m/z=Found 487.4252 M$^+$; calculated for C$_{31}$H$_{55}$N$_2$O$_2$ 487.4258; 1.2 ppm.

Synthesis of allyl-[2-[[(4R)-4-[(3R,10S,12S,13R,17R)-3,12-dihydroxy-10,13-dimethyl-2,3,4,5,6,7,8,9,11,12,14,15,16,17-tetradecahydro-1H-cyclopenta[a]phenanthren-17-yl]pentanoyl]amino]ethyl]-dimethyl-ammonium iodide (128)

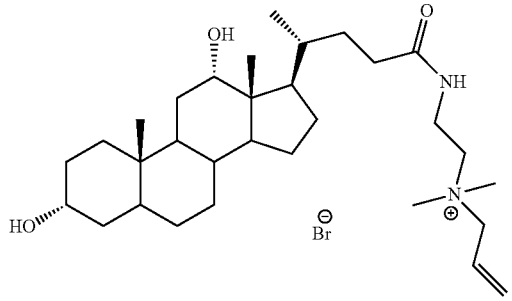 [SMILES: C=CC[N+](C)(C)CCNC(=O)CC[C@@H](C)[C@H]1CCC2C3CCC4C[C@H](O)CC[C@]4(C)C3C[C@H](O)[C@@]21C ; [Br-]]

Compound 102 (0.15 g, 0.0003 mol) was dissolved in chloroform (5 mL). Allyl bromide (0.20 mL, 0.0016 mol) was added and the solution was stirred overnight at ambient temperature. The resulting precipitate was collected by vacuum filtration and was dried overnight in a desiccator. The product was an off-white solid.

Yield; 0.19 g, 0.0001 mol, 53%.
Melting point: 184.2-186.7° C.
$^1$H NMR (MeOD) (250 MHz) δ=0.70 (s, 3H, CH$_3$), 0.93 (s, 3H, CH$_3$), 3.13 (s, 6H, CH$_3$), 3.40 (t, 2H, CH$_2$, J=7.5), 3.65 (t, 2H, CH$_2$, J=5.0), 3.95 (s, 1H, 12-CH), 4.05 (d, 2H, CH$_2$, J=5.0), 5.75 (m, 2H, CH$_2$), 6.10 (m, 1H, =CH—) ppm.
$^{13}$C NMR (62.9 MHz) δ=13.2 (CH$_3$, C18), 17.6 (CH$_3$, C21), 23.7 (CH$_3$, C19), 24.8 (CH$_2$, C15), 27.4 (CH$_2$, C7), 28.4 (CH$_2$, C6), 28.7 (CH$_2$, C16), 29.9 (CH$_2$, C11), 31.1 (CH$_2$, C2), 33.0 (CH$_2$, C23), 33.8 (CH$_2$, C22), 34.8 (CH, C9), 36.9 (CH), 37.2 (CH), 37.4 (CH), 43.6 (CH, C5), 47.5 (CH, C17), 48.0 (CH, C14), 63.0 (CH$_2$), 63.1 (CH$_2$), 67.9 (CH$_2$), 68.0 (CH$_2$), 68.0 (CH$_2$) 72.5 (CH, C3), 74.0 (CH$_2$, C12), 126.1 (CH$_3$), 129.8 (CH), 177.4 (CO, C24) ppm.
IR=3415 (NH), 3245 (OH), 2925 (alkyl), 2852 (alkyl), 1646 (C=O), 1441, 1364, 1292 cm$^{-1}$.

MS (+ESI) m/z=Found 503.4202 M⁺; calculated for C₃₁H₅₅N₂O₃ 503.4207; 1.0 ppm.

Synthesis of 2-[[(4R)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]pentanoyl]amino]ethyl-dimethyl-[(4-vinylphenyl)methyl]ammonium chloride (129)

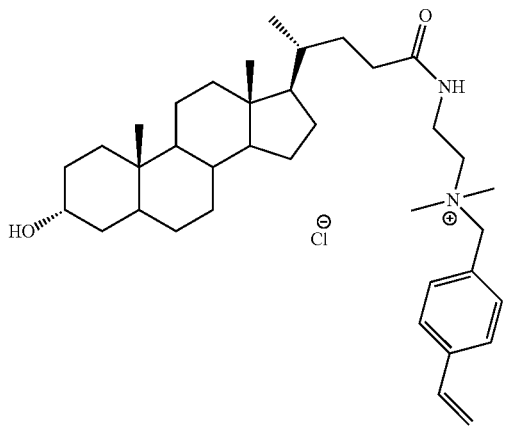 [SMILES: C=Cc1ccc(C[N+](C)(C)CCNC(=O)CC[C@@H](C)[C@H]2CCC3C4CCC5C[C@H](O)CC[C@]5(C)C4CC[C@@]32C)cc1 ; [Cl-]]

Compound 101 (0.2 g 0.0004 mol) was dissolved in chloroform (10 mL). Vinyl benzyl chloride (0.64 mL, 0.004 mol) was added and the solution was stirred overnight at ambient temperature. The resulting precipitate was collected by vacuum filtration and was dried overnight in a desiccator. The product was an off-white solid.

Yield; 0.07 g, 0.0016 mol, 26.9%.

Melting point: 143.8-148.9° C.

¹H NMR (MeOD) (250 MHz) δ=0.66 (s, 3H, 18-CH₃), 0.94 (s, 3H, 19-CH₃), 3.09 (s, 6H, 2×CH₃), 3.41 (t, 2H, CH₂, J=7.5), 3.73 (t, 2H, CH₂, J=5.0), 4.56 (s, 2H, CH₂), 5.37 (d, 1H, =CH—, J=12.5), 5.91 (d, 1H, =CH, J=20.0) 6.80 (dd, 1H, =CH, J=10.0), 7.57 (dd, 4H, Ar—CH, J=5.0) ppm.

¹³C NMR (62.9 MHz) δ=11.7 (CH₃, C18), 18.0 (CH₃, C21), 21.1 (CH₂, C11), 23.1 (CH₃, C19), 24.4 (CH₂, C15), 26.8 (CH₂, C7), 27.5 (CH₂, C6), 28.4 (CH₂, C16), 30.3 (CH₂, C2), 33.0 (CH₂), 33.9 (CH₂), 35.7 (CH₂), 36.8 (CH), 37.2 (CH), 41.9 (CH), 43.5 (CH), 57.4 (CH, C17), 57.9 (CH, C14), 63.5 (CH₂) 71.6 (CH, C3), 115.8 (CH), 126.9 (CH), 127.2 (CH), 133.6 (CH), 136.2 (CH), 140.8 (CH), 176.5 (CO, C24) ppm.

IR=3339 (NH), 3215 (OH), 2921 (alkyl), 2857 (alkyl), 1667 (C=O), 1646, 1445, 1356, 1070 (R₂CH—OH) cm⁻¹.

MS (+ESI) m/z=Found 563.4558 M⁺; calculated for C₃₇H₅₉N₂O₂ 563.4571; 2.3 ppm.

Synthesis 3-[[(4R)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]pentanoyl]amino]propyl-trimethyl-ammonium iodide (130)

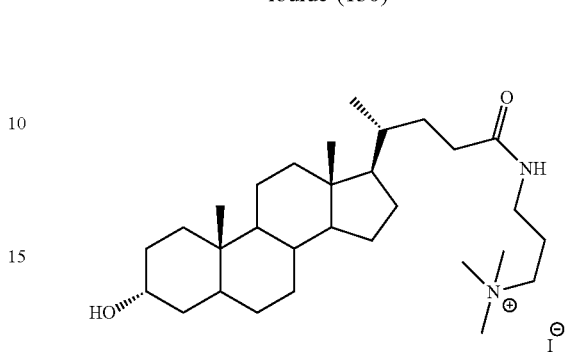

Compound 103 (0.5 g 0.002 mol) was dissolved in a mixture of chloroform (15 mL) and methanol (4 mL). Iodomethane (3.63 mL, 0.02 mol) was added and the solution was stirred for four days at ambient temperature. To induce precipitation the solution was placed in a acetone/dry ice mixture (−78° C.). The resulting precipitate was collected by vacuum filtration and was dried overnight in a desiccator. The product was an off-white solid.

Yield; 0.42 g, 0.06 mol, 64.6%.

Melting point: 253.8-255.4° C.

¹H NMR (CDCl₃) (250 MHz) δ=0.69 (s, 3H, 18-CH₃), 0.94 (s, 3H, 19-CH₃), 3.13 (s, 9H, 3×CH₃), 3.54 (m, 1H, 3-CH) ppm.

¹³C NMR (62.9 MHz) δ=10.9 (CH₃, C18), 17.3 (CH₃, C21), 20.4 (CH₂, C11), 22.4 (CH₂), 23.0 (CH₃, C19), 23.7 (CH₂, C15), 26.1 (CH₂, C7), 26.8 (CH₂, C6), 28.0 (CH₂, C16), 29.6 (CH₂, C2), 31.6 (CH₂, C22), 32.5 (CH₂, C23), 34.1 (C, C10), 34.9 (CH, C20), 35.4 (CH₂, C1), 35.6 (CH, C8), 35.7 (CH₂, C4), 40.0 (CH₂, C12), 40.4 (CH, C9), 42.0 (CH, C5), 42.4 (C, C13), 52.2 (CH, C17), 55.8 (CH, C14), 56.8 (CH), 64.2 (CH₂) 70.8 (CH, C3), 175.7 (CO, C24) ppm.

IR=3386 (OH), 2921 (alkyl), 2852 (alkyl), 1641 (C=O), 1552, 1441, 1368, 1253 (C=O ester stretch), 1031 (R₂CH—OH) cm⁻¹.

MS (+ESI) m/z=Found 475.4256 M⁺; calculated for C₃₀H₅₅N₂O₂ 475.4258; 0.4 ppm.

Synthesis of 3-[[(4R)-4-[(3R,10S,12S,13R,17R)-3,12-dihydroxy-10,13-dimethyl-2,3,4,5,6,7,8,9,11,12,14,15,16,17-tetradecahydro-1H-cyclopenta[a]phenanthren-17-yl]pentanoyl]amino]propyl-trimethyl-ammonium iodide (131)

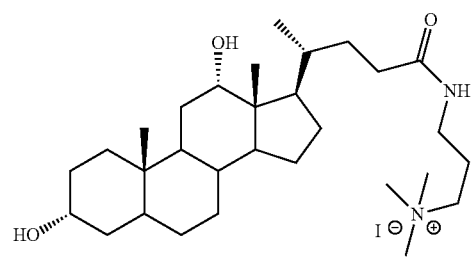 [SMILES: C[C@H](CCC(=O)NCCC[N+](C)(C)C)[C@H]1CCC2C3CCC4C[C@H](O)CC[C@]4(C)C3C[C@H](O)[C@@]21C ; [I-]]

Compound 104 (0.1 g 0.0002 mol) was dissolved in chloroform (5 mL). Iodomethane (0.29 mL, 0.002 mol) was added and the solution was stirred overnight at ambient temperature. The resulting precipitate was collected by vacuum filtration and was dried overnight in a desiccator. The product was an off-white solid.

Yield; 0.09 g, 0.0014 mol, 75%.

Melting point: 150.1-153.3° C.

$^1$H NMR (MeOD) (250 MHz) δ=0.71 (s, 3H, 18-CH$_3$), 0.93 (s, 3H, 19-CH$_3$), 1.03 (d, 3H, 21-CH$_3$, J=7.5), 3.15 (s, 6H, 2×CH$_3$), 3.53 (m, 1H, 3-CH), 3.95 (s, 1H, 12-CH) ppm.

$^{13}$C NMR (62.9 MHz) δ=13.2 (CH$_3$, C18), 17.7 (CH$_3$, C21), 23.7 (CH$_3$, C19), 27.4 (CH$_2$, C7), 28.4 (CH$_2$, C6), 28.7 (CH$_2$, C16), 29.9 (CH$_2$, C11), 31.1 (CH$_2$, C2), 33.1 (CH$_2$, C23), 35.3 (C, C10), 37.2 (CH$_2$, C4), 43.6 (CH, C5), 72.5 (CH, C3), 74.0 (CH$_2$, C12), 177.3 (CO, C24) ppm.

IR=3364 (OH), 2933 (alkyl), 2852 (alkyl), 1654 (C=O), 1548, 1437 cm$^{-1}$.

MS (ES) m/z=Found 491.4195 M$^+$; calculated for C$_{30}$H$_{55}$N$_2$O$_3$ 491.4207; 2.5 ppm.

Synthesis of allyl-[3-[[(4R)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]pentanoyl]amino]propyl]-dimethyl-ammonium bromide (132)

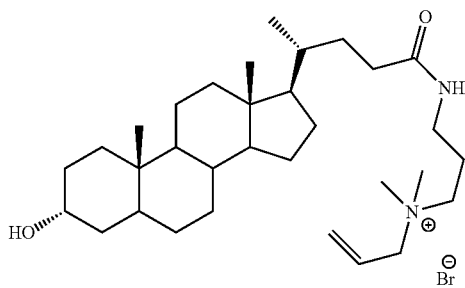 [SMILES: C=CC[N+](C)(C)CCCNC(=O)CC[C@@H](C)[C@H]1CCC2C3CCC4C[C@H](O)CC[C@]4(C)C3CC[C@@]21C ; [Br-]]

Compound 103 (0.5 g 0.001 mol) was dissolved in dichloromethane (20 mL). Allyl bromide (1.88 mL, 0.01 mol) was added and the solution was stirred for a further 5 days. The reaction mixture was chilled to −78° C. A precipitate formed. This was collected by vacuum filtration.

Yield; 0.45 g, 0.0007 mol, 71%.

Melting point: 191.1-209.9° C.

$^1$H NMR (CDCl$_3$) (250 MHz) δ=0.68 (s, 3H, 18-CH$_3$), 0.94 (s, 3H, 19-CH$_3$), 3.10 (s, 6H, 2×CH$_3$), 3.27 (q, 2H, CH$_2$), 3.54 (m, 1H, 3-CH), 4.01 (d, 2H, CH$_2$, J=7.5), 5.74 (t, 2H, CH$_2$, J=10.0), 6.08 (m, 1H, NH) ppm.

$^{13}$C NMR (62.9 MHz) δ=11.1 (CH$_3$, C18), 17.5 (CH$_3$, C21), 20.5 (CH$_2$, C11), 22.5 (CH$_3$, C19), 23.8 (CH$_2$, C15), 26.2 (CH$_2$, C7), 26.9 (CH$_2$, C6), 27.0 (CH$_2$, C16), 29.7 (CH$_2$, C2), 31.7 (CH$_2$, C22), 32.5 (CH$_2$, C23), 34.2 (C, C10), 35.0 (CH, C20), 35.4 (CH$_2$, C1), 35.7 (CH, C8), 35.9 (CH$_2$, C4), 40.0 (CH$_2$, C12), 40.4 (CH, C9), 42.0 (CH, C5), 42.4 (C, C13), 55.9 (CH, C17), 56.4 (CH, C14), 61.7 (CH$_2$), 66.1 (CH$_2$) 70.9 (CH, C3), 124.8 (CH), 128.0 (CH$_2$), 175.8 (CO, C24) ppm.

IR=3411 (NH), 3270 (OH), 2925 (alkyl), 2857 (alkyl), 1646 (C=O), 1543, 1437, 1373, 1036 (R$_2$CH—OH) cm$^{-1}$.

MS (+ESI) m/z=Found 501.4405 M$^+$; calculated for C$_{31}$H$_{55}$N$_2$O$_2$.

Synthesis of cyclopentylmethyl-[3-[[(4R)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]pentanoyl]amino]propyl]-dimethyl-ammonium bromide (133)

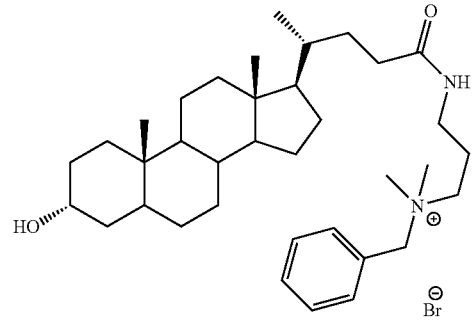 [SMILES: C[C@H](CCC(=O)NCCC[N+](C)(C)Cc1ccccc1)[C@H]1CCC2C3CCC4C[C@H](O)CC[C@]4(C)C3CC[C@@]21C ; [Br-]]

Compound 103 (0.5 g 0.001 mol) was dissolved in chloroform (20 mL) with benzyl bromide (1.37 mL, 0.008 mol) and the solution was stirred for 48 hours. The solvent was evaporated under reduced pressure, then re-dissolved in methanol and washed with petroleum ether 60/80 (3×20 mL). The solvent was removed under reduced pressure to produce a white powder.

Yield; 0.24 g, 0.0003 mol, 35%.

Melting point: 145-147.9° C.

$^1$H NMR (MeOD) (250 MHz) δ=0.68 (s, 3H, 18-CH$_3$), 0.94 (s, 3H, 19-CH$_3$), 3.05 (s, 6H, 2×CH$_3$), 3.54 (m, 1H, 3-CH), 4.56 (s, 2H, CH$_2$), 7.55 (broad s, 5H, Ar—CH) ppm.

$^{13}$C NMR (62.9 MHz) δ=10.9 (CH$_3$, C18), 17.3 (CH$_3$, C21), 20.4 (CH$_2$, C11), 22.4 (CH$_3$, C19), 22.6 (CH$_2$, C15), 23.7 (CH) 26.1 (CH$_2$, C7), 26.8 (CH$_2$, C6), 27.7 (CH$_2$, C16), 29.6 (CH$_2$, C2), 31.6 (CH$_2$, C22), 32.5 (CH$_2$, C23), 34.1 (C, C10), 34.9 (CH, C20), 35.3 (CH$_2$, C1), 35.6 (CH, C8), 35.6 (CH$_2$, C4), 39.9 (CH$_2$, C12), 40.3 (CH, C9), 41.9 (CH, C5), 42.3 (C, C13), 55.8 (CH, C17), 56.3 (CH, C14), 61.7 (CH), 67.4 (CH), 70.8 (CH, C3), 127.3 (CH), 128.8 (CH), 130.3 (CH), 132.6 (CH), 175.6 (CO, C24) ppm.

IR=3253 (OH), 2929 (alkyl), 2865 (alkyl), 1637 (C=O), 1565, 1441 cm$^{-1}$.

MS (+ESI) m/z=Found 551.4570 M$^+$; calculated for C$_{36}$H$_{59}$N$_2$O$_2$ 551.4571; 0.2 ppm.

Synthesis of 3-[[(4R)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]pentanoyl]amino]propyl-dimethyl-[(4-vinylphenyl)methyl]ammonium chloride (134)

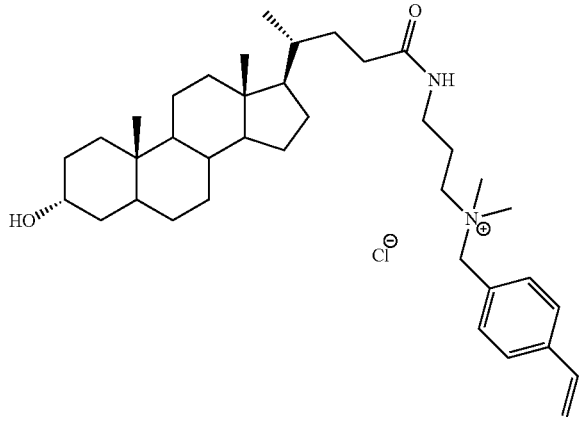 [SMILES: C=Cc1ccc(C[N+](C)(C)CCCNC(=O)CC[C@@H](C)[C@H]2CCC3C4CCC5C[C@H](O)CC[C@]5(C)C4CC[C@@]32C)cc1 ; [Cl-]]

Compound 103 (1.0 g 0.001 mol) was dissolved in dichloromethane (20 mL). Vinyl benzyl chloride (0.89 mL, 0.005) was added and the solution was stirred for 48 hours at ambient temperature. The resulting precipitate was collected by vacuum filtration and was washed with petroleum ether 60/80 (3×20 mL). The resultant crude product was dissolved in methanol and again washed with petroleum ether 60/80 (3×20 mL).

The solvent was removed under reduced pressure to produce off-white solid.

Yield; 1 g, 0.001 mol, 75%.

Melting point: >350° C.

$^1$H NMR (MeOD) (250 MHz) δ=0.67 (s, 3H, 18-CH$_3$), 0.94 (s, 3H, 19-CH$_3$), 3.05 (s, 6H, 2×CH$_3$), 4.54 (s, 2H, CH$_2$), 5.37 (d, 1H, =CH—, J=12.5), 5.91 (d, 2H, =CH, J=15.0), 6.80 (dd, 1H, =CH, J=12.5), 7.56 (q, 5H, Ar—CH, J=7.5) ppm.

$^{13}$C NMR (62.9 MHz) δ=11.9 (CH$_3$, C18), 18.2 (CH$_3$, C21), 20.6 (CH$_2$, C11), 23.3 (CH$_3$, C19), 24.0 (CH$_2$, C15), 26.3 (CH$_2$, C7), 27.1 (CH$_2$, C6), 28.0 (CH$_2$, C16), 30.3 (CH$_2$, C2), 30.9 (CH$_2$, C7), 30.9 (CH$_2$, C22), 30.9 (CH$_2$, C23), 34.2 (C, C10), 35.1 (CH, C20), 35.3 (CH$_2$, C1), 35.6 (CH, C8), 36.3 (CH$_2$, C4), 40.0 (CH$_2$, C12), 40.2 (CH, C9), 41.9 (CH, C5), 42.4 (C, C13), 55.8 (CH, C17), 56.3 (CH, C14), 70.5 (CH, C3), 178.1 (CO, C24) ppm.

IR=3356 (OH), 2929 (alkyl), 2852 (alkyl), 1633 (C=O), 1548, 1441, 1031 (R$_2$CH—OH) cm$^{-1}$.

MS (+ESI) m/z=Found 577.4723 M$^+$; calculated for C$_{38}$H$_{61}$N$_2$O$_2$ 577.4728; 0.8 ppm.

Synthesis of (4R)-4-[(3R,10S,12S,13R,17R)-3,12-dihydroxy-10,13-dimethyl-2,3,4,5,6,7,8,9,11,12,14,15,16,17-tetradecahydro-1H-cyclopenta[a]phenanthren-17-yl]-N-[2-(1-methylpyrrolidin-1-ium-1-yl)ethyl]pentanamide iodide (135)

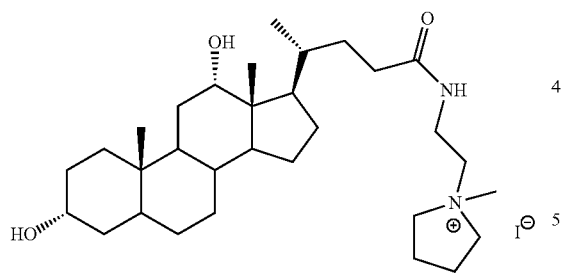

Compound 108 (0.1 g 0.0002 mol) was dissolved in chloroform (10 mL). Methyl iodide (0.09 mL 0.0006 mol) was added and the solution was stirred for 1 week. The solvent was evaporated under reduced pressure. The residue was re-dissolved in methanol and washed with petroleum ether 60/80 (3×20 mL). The methanol phase was evaporated under reduced pressure to give the product as a green-brown oil was produced.

Yield; 0.08 g, 0.0001 mol, 66%.

$^1$H NMR (CDCl$_3$) (250 MHz) δ=0.70 (s, 3H, 18-CH$_3$), 0.93 (s, 3H, 19-CH$_3$), 1.00 (d, 3H, 21-CH$_3$ J=10.0), 3.15 (s, 3H, CH$_3$), 3.50-3.70 (multiple overlapping multiplets, 7H, CH/CH$_2$), 3.95 (s, 1H, 12-CH) ppm.

$^{13}$C NMR (250 MHz) δ=13.2 (CH$_3$, C18), 17.7 (CH$_3$, C21), 22.56 (CH$_2$) 23.7 (CH$_3$, C19), 24.9 (CH$_2$, C15), 27.5 (CH$_2$, C7), 28.44 (CH$_2$, C6), 28.7 (CH$_2$, C16), 29.9 (CH$_2$, C11), 31.1 (CH$_2$, C2), 33.0 (CH$_2$, C23), 33.9 (CH$_2$, C22), 34.8 (CH, C9), 35.3 (C, C10), 36.4 (CH$_2$, C1), 36.9 (CH, C20), 37.2 (CH$_2$, C4), 37.4 (CH, C8), 43.6 (CH, C5), 63.5 (CH$_2$), 66.1 (CH$_2$), 72.5 (CH, C3), 74.0 (CH$_2$, C12), 176.5 (CO, C24) ppm.

IR=3394 (OH), 2916 (alkyl), 2857 (alkyl), 1646 (C=O), 1530, 1445, 1368, 1253, 1036 (RCH—OH) cm$^{-1}$.

MS (+ESI) m/z=Found 503.4201 M$^+$; calculated for C$_{31}$H$_{55}$N$_2$O$_3$ 503.4207; 1.2 ppm.

Synthesis of (4R)—N-[2-(1-allylpyrrolidin-1-ium-1-yl)ethyl]-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]pentanamide bromide (136)

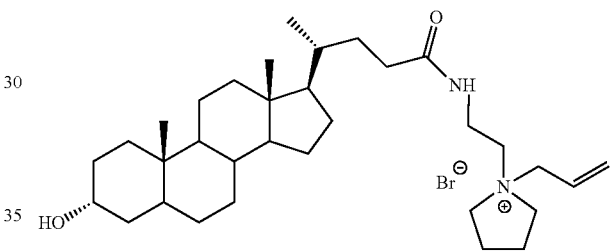

Compound 107 (0.5 g 0.001 mol) was dissolved in dichloromethane (15 mL). Ally bromide (2.79 mL, 0.02) was added and the solution was stirred for 48 hours at 50° C. The resulting precipitate was collected by vacuum filtration, triturated chloroform (3×20 mL) and dried under vacuum.

Yield; 0.168 g, 0.0002 mol, 27%.

Melting point: 211.6-214.8° C.

$^1$H NMR (MeOD) (250 MHz) δ=0.68 (s, 3H, 18-CH$_3$), 0.94 (s, 3H, 19-CH$_3$), 3.62 (overlapping mutliplets, 4H, CH$_2$), 4.02 (d, 2H, CH$_2$, J=7.5), 5.74 (multiple overlapping multiplets, 2H, =CH$_2$), 6.11 (m, 1H, =CH—) ppm.

$^{13}$C NMR (62.9 MHz) δ=11.0 (CH$_3$, C18), 17.3 (CH$_3$, C21), 20.4 (CH$_2$, C11), 22.3 (CH$_3$, C19), 22.4 (CH) 23.7 (CH$_2$, C15), 26.1 (CH$_2$, C7), 26.8 (CH$_2$, C6), 27.7 (CH$_2$, C16), 29.6 (CH$_2$, C2), 31.4 (CH$_2$, C22), 32.3 (CH$_2$, C23), 33.2 (C, C10), 34.1 (CH, C20), 34.9 (CH$_2$, C1), 35.3 (CH, C8), 35.6 (CH$_2$, C4), 40.0 (CH$_2$, C12), 40.3 (CH, C9), 42.0 (CH, C5), 42.4 (C, C13), 55.6 (CH, C17), 56.4 (CH, C14), 57.8 (CH$_2$), 61.3 (CH$_2$), 62.1 (CH$_2$) 70.8 (CH, C3), 125.2 (CH), 127.3 (CH$_2$) 175.8 (CO, C24) ppm.

IR=3411 (NH), 3198 (OH), 2925 (alkyl), 2852 (alkyl), 1637 (C=O), 1560, 1441, 1368, 1066 (R$_2$CH—OH) cm$^{-1}$.

MS (+ESI) m/z=Found 513.4405 M$^+$; calculated for C$_{33}$H$_{57}$N$_2$O$_2$ 513.4415; 1.9 ppm.

Synthesis of (4R)—N-[2-(1-allylpyrrolidin-1-ium-1-yl)ethyl]-4-[(3R,10S,12S,13R,17R)-3,12-dihydroxy-10,13-dimethyl-2,3,4,5,6,7,8,9,11,12,14,15,16,17-tetradecahydro-1H-cyclopenta[a]phenanthren-17-yl] pentanamide bromide (137)

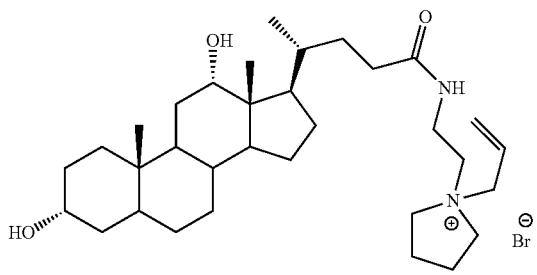 [SMILES: C=CC[N+]1(CCNC(=O)CC[C@@H](C)[C@H]2CCC3C4CCC5C[C@H](O)CC[C@]5(C)C4C[C@H](O)[C@@]32C)CCCC1 ; [Br-]]

Compound 108 (0.1 g 0.0002 mol) was dissolved in chloroform (10 mL) with allyl bromide (0.08 mL, 0.0006 mol). The solution was stirred for 1 week. The solvent was evaporated under reduced pressure and the product was re-dissolved in methanol and washed with petroleum ether (3×10 mL). The solvent was then removed under reduced pressure to produce a white solid.

Yield; 0.1 g, 0.0001 mol, 83%.
Melting point: 176.2-179.8° C.
$^1$H NMR (MeOD) (250 MHz) δ=0.70 (s, 3H, 18-CH$_3$), 0.93 (s, 3H, 19-CH$_3$), 1.02 (d, 3H, 21-CH$_3$, J=5.0), 2.22 (broad s, 4H, CH$_2$), 3.515 (q, 2H, CH$_2$), 3.65 (m, 3H, CH$_2$/3-CH), 4.01 (broad s, 1H, 12-CH), 4.025 (d, 2H, CH$_2$ J=7.5), 5.74 (m, 2H, CH$_2$), 6.11 (m, 1H, =CH—) ppm.
$^{13}$C NMR (62.9 MHz) δ=12.4 (CH$_3$, C18), 16.8 (CH$_3$, C21), 21.8 (CH$_2$), 22.9 (CH$_3$, C19), 24.0 (CH$_2$, C15), 26.6 (CH$_2$), 27.6 (CH$_2$, C7), 27.9 (CH$_2$, C6), 28.1 (CH$_2$, C16), 30.9 (CH$_2$, C2), 32.2 (CH$_2$, C23), 33.0 (CH$_2$, C22), 34.0 (CH, C9), 36.0 (CH$_2$), 36.6 (CH, C20), 42.7 (CH, C5), 44.8 (C, C13), 47.1 (CH, C17), 58.4 (CH$_2$), 61.9 (CH$_2$), 62.8 (CH$_2$) 71.7 (CH, C3), 73.1 (CH$_2$, C12), 126.7 (CH$_2$), 128.9 (CH$_2$) 177.4 (CO, C24) ppm.
IR=3305 (OH), 2921 (alkyl), 2857 (alkyl), 1641 (C=O), 1539, 1449, 1040 (R$_2$CH—OH) cm$^{-1}$.
MS (+ESI) m/z=Found 529.4349 M$^+$; calculated for C$_{33}$H$_{57}$N$_2$O$_3$, 529.4364; 2.8 ppm.

Synthesis of (4R)—N-[2-(1-benzylpyrrolidin-1-ium-1-yl)ethyl]-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl] pentanamide bromide (138)

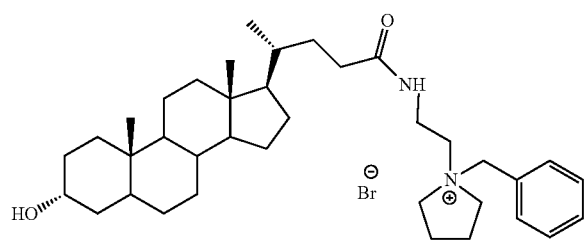 [SMILES: C[C@H](CCC(=O)NCC[N+]1(Cc2ccccc2)CCCC1)[C@H]1CCC2C3CCC4C[C@H](O)CC[C@]4(C)C3CC[C@@]21C ; [Br-]]

Compound 107 (0.5 g 0.001 mol) was dissolved in dichloromethane (20 mL). Benzyl bromide (1.42 mL 0.008 mol) was added and the solution was stirred for 24 hours. The resultant precipitate was collected by vacuum filtration to produce a white powder.

Yield: 0.01 g, 0.0001 mol, 1.5%.
Melting point: 216.2-220.8° C.
$^1$H NMR (CDCl$_3$) (250 MHz) δ=0.66 (s, 3H, 18-CH$_3$), 0.94 (s, 3H, 19-CH$_3$), 3.54-3.76 (multiple overlapping multiplets, 7H, 3-CH/CH$_2$), 4.57 (s, 2H, CH$_2$), 7.56 (m, 5H, Ar—CH) ppm.
$^{13}$C NMR (62.9 MHz) δ=10.9 (CH$_3$, C18), 17.3 (CH$_3$, C21), 20.4 (CH$_2$), 20.7 (CH$_2$, C11), 22.4 (CH$_3$, C19), 23.7 (CH$_2$, C15), 27.7 (CH$_2$, C16), 29.6 (CH$_2$, C2), 31.5 (CH$_2$, C22), 32.3 (CH$_2$, C23), 34.1 (C, C10), 34.9 (CH, C20), 35.3 (CH$_2$, C1), 35.6 (CH, C8), 35.7 (CH$_2$, C4), 40.0 (CH$_2$, C12), 40.3 (CH, C9), 41.9 (CH, C5), 42.4 (C, C13), 55.8 (CH, C17), 56.4 (CH, C14), 57.0 (CH), 61.2 (CH), 70.8 (CH, C3), 127.7 (CH), 129.0 (CH), 130.4 (CH), 132.2 (CH) 175.8 (CO, C24) ppm.
IR=3343 (NH), 3241 (OH), 2929 (alkyl), 2844 (alkyl), 1667 (C=O), 1535, 1445, 1360, 1070 (R$_2$CH—OH) cm$^{-1}$.
MS (+ESI) m/z=Found 563.4563 M$^+$; calculated for C$_{37}$H$_{59}$N$_2$O$_2$ 563.4571; 1.4 ppm.

Synthesis of (4R)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]-N-[2-[1-[(4-vinylphenyl)methyl]pyrrolidin-1-ium-1-yl]ethyl]pentanamide chloride (139)

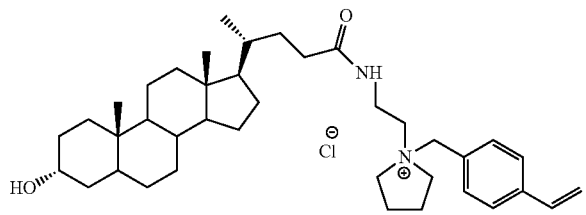 [SMILES: C=Cc1ccc(C[N+]2(CCNC(=O)CC[C@@H](C)[C@H]3CCC4C5CCC6C[C@H](O)CC[C@]6(C)C5CC[C@@]43C)CCCC2)cc1 ; [Cl-]]

Compound 107 (0.5 g 0.001 mol) was dissolved in dichloromethane (20 mL). Vinyl benzyl chloride (1.74 mL 0.01 mol) was added and the solution was stirred for 48 hours at ambient temperature followed by heating at 50° C. for 15 h. The solvent was evaporated under reduced pressure. The material re-dissolved in methanol and washed with petroleum ether 60-80 (3×20 mL). A white solid was produced. This was collected by vacuum filtration and dried under vacuum.

Yield: 0.08 g, 0.0001 mol, 12%.
Melting point: >350° C.
$^1$H NMR (CDCl$_3$) (250 MHz) δ=0.65 (s, 3H, 18-CH$_3$), 0.94 (s, 3H, 19-CH$_3$), 3.56 (multiple overlapping multiplets, 4H, CH$_2$), 4.57 (s, 2H, CH$_2$), 5.37 (d, 1H, =CH—, J=12.5), 5.90 (d, 1H, =CH, J=17.5), 6.80 (dd, 1H, =CH, J=12.5), 7.60 (s, 4H, Ar—CH) ppm.
$^{13}$C NMR (62.9 MHz) δ=10.9 (CH$_3$, C18), 17.3 (CH$_3$, C21), 20.4 (CH$_2$, C11), 20.7 (CH$_2$), 22.4 (CH$_3$, C19), 23.7 (CH$_2$, C15), 26.1 (CH$_2$, C7), 27.7 (CH$_2$, C16), 29.6 (CH$_2$, C2), 31.5 (CH$_2$, C22), 32.3 (CH$_2$, C23), 33.2 (C, C10), 34.1 (CH, C20), 34.9 (CH$_2$, C1), 35.3 (CH, C8), 35.7 (CH$_2$, C4), 40.0 (CH$_2$, C12), 40.3 (CH, C9), 41.9 (CH, C5), 42.4 (C, C13), 55.8 (CH, C17), 56.4 (CH, C14), 57.0 (CH$_2$), 61.2 (CH), 61.8 (CH$_2$) 70.8 (CH, C3), 115.0 (CH), 126.6 (CH), 132.5 (CH), 135.4 (CH), 139.9 (CH), 175.8 (CO, C24) ppm.

IR=3360 (OH), 2925 (alkyl), 2852 (alkyl), 1641 (C=O), 1539, 1437, 1368, 1036 (R$_2$CH—OH) cm$^{-1}$.

MS (+ESI) m/z=Found 589.4719 M$^+$; calculated for C$_{39}$H$_{61}$N$_2$O$_2$ 589.4728; 1.5 ppm.

Synthesis of (4R)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]-1-[4-(2-hydroxyethyl)-4-methyl-piperazin-4-ium-1-yl]pentan-1-one iodide (140)

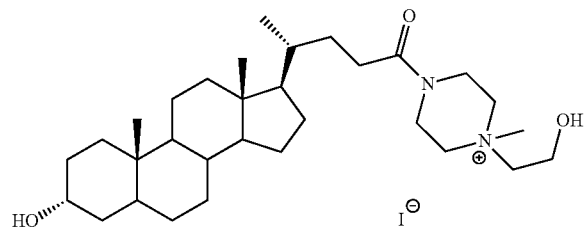 [SMILES: C[C@H](CCC(=O)N1CC[N+](C)(CCO)CC1)[C@H]1CCC2C3CCC4C[C@H](O)CC[C@]4(C)C3CC[C@@]21C ; [I-]]

Compound 118 (0.2 g 0.0004 mol) was dissolved in chloroform (5 mL). Iodomethane (0.29 mL, 0.002 mol) was added and the solution was stirred overnight at ambient temperature. The resulting precipitate was collected by vacuum filtration and was dried overnight in a desiccator. The product was an off-white solid.

Yield; 0.01 g, 0.00001 mol, 4%.
Melting point: 245.3-251.3° C.

$^1$H NMR (MeOD) (250 MHz) δ=0.69 (s, 3H, 18-CH$_3$), 0.94 (s, 3H, 19-CH$_3$), 0.98 (d, 3H, 21-CH$_3$, J=5.0), 3.54-3.65 (multiple overlapping multiplets, 6H, CH$_2$), 4.01 (multiple overlapping multiplets, 6H, CH$_2$) ppm.

$^{13}$C NMR (62.9 MHz) δ=11.5 (CH$_3$, C18), 16.4 (CH$_3$, C21), 22.9 (CH$_2$, C11), 25.9 (CH$_2$), 27.8 (CH$_2$), 32.2 (CH), 33.2 (CH), 34.6 (C, C10), 35.1 (CH, C20), 41.1 (CH, C5), 42.4 (C, C13), 44.5 (CH$_2$), 45.8 (CH), 47.4 (CH), 60.4 (CH$_2$), 61.3 (CH), 61.8 (CH), 67.1 (CH$_2$), 70.1 (CH, C3), 71.2 (CH$_2$), 75.7 (CH$_2$), 76.3 (CH$_2$), 80.6 (CH$_2$) 174.8 (CO, C24) ppm.

IR=3313 (OH), 2929 (alkyl), 2852 (alkyl), 1607 (C=O), 1466, 1249, 1044 (R$_2$CH—OH) cm$^{-1}$.

MS (+ESI) m/z=Found 503.4195 M$^+$; calculated for C$_{31}$H$_{55}$N$_2$O$_3$ 503.4207; 2.4 ppm.

Synthesis of (4R)-1-[4-allyl-4-(2-hydroxyethyl)piperazin-4-ium-1-yl]-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]pentan-1-one bromide (141)

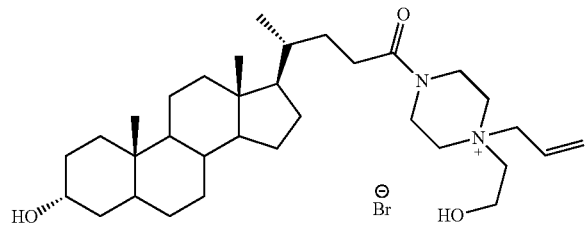

Compound 118 (0.2 g 0.0004 mol) was dissolved in chloroform (5 mL). Allyl bromide (0.44 mL, 0.003 mol) was added and the solution was stirred overnight at ambient temperature. The resulting precipitate was collected by vacuum filtration and was dried overnight in a desiccator. The product was an off-white solid.

Yield; 0.02 g, 0.00003 mol, 8%.
Melting point: 194.9-197.8° C.

$^1$H NMR (MeOD) (250 MHz) δ=0.70 (s, 3H, 18-CH$_3$), 0.94 (s, 3H, 19-CH$_3$), 0.98 (d, 3H, 21-CH$_3$, J=7.5), 3.54-3.65 (multiple overlapping multiplets, 6H, CH$_2$), 4.01 (multiple overlapping multiplets, 6H, CH$_2$), 4.27 (d, 2H, CH$_2$, J=7.5), 5.76 (dd, 2H, =CH$_2$), 6.10 (m, 1H, =CH—) ppm.

$^{13}$C NMR (62.9 MHz) δ=12.5 (CH$_3$, C18), 18.9 (CH$_3$, C21), 21.9 (CH$_2$, C11), 23.9 (CH$_3$, C19), 25.3 (CH$_2$, C15), 27.6 (CH$_2$, C6), 28.3 (CH$_2$, C16), 29.3 (CH$_2$, C2), 30.6 (CH$_2$, C22), 31.1 (CH$_2$, C23), 32.2 (C, C10), 35.6 (CH, C20), 36.4 (CH$_2$, C1), 36.9 (CH, C8), 37.2 (CH$_2$, C4), 41.5 (CH$_2$, C12), 41.9 (CH, C9), 56.4 (CH, C17), 57.4 (CH, C14), 57.9 (CH$_2$), 59.4 (CH$_2$), 61.6 (CH$_2$), 63.7 (CH$_2$) 72.4 (CH, C3), 125.6 (CH), 129.9 (CH), 174.8 (CO, C24) ppm.

IR=3350 (NH), 3241 (OH), 2938 (alkyl), 2850 (alkyl), 1633 (C=O), 1439, 1244, 1189.78 (C=O ester stretch), 1244 (R$_2$CH—OH) cm$^{-1}$.

MS (ES) m/z=Found 529.4349 M$^+$; calculated for C$_{33}$H$_{57}$N$_2$O$_3$ 529.4364; 2.8 ppm.

Synthesis of (4R)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]-1-[4-(2-hydroxyethyl)-4-pentyl-piperazin-4-ium-1-yl]pentan-1-one bromide (142)

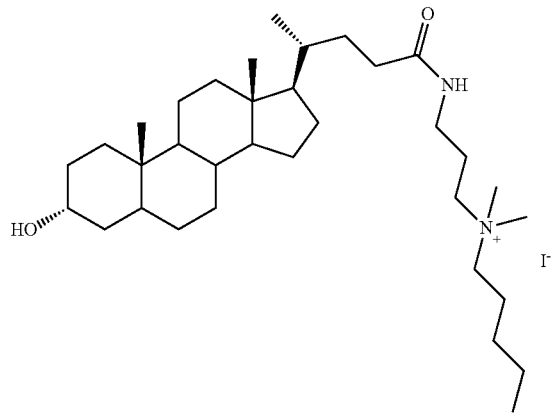

Compound 103 (0.5 g 0.001 mol) was dissolved in dichloromethane (20 mL). Iodopentane (1.57 mL, 0.007 mol) was added and the solution was stirred overnight at 40° C. The resulting precipitate was collected by vacuum filtration and was dried overnight in a desiccator. The product was an off-white solid.

Yield; 0.36 g, 0.0005 mol, 50.7%.
Melting point: 104.8-108.6° C.

$^1$H NMR (MeOD) (250 MHz) δ=0.66 (s, 3H, 18-CH$_3$), 0.92 (s, 3H, 19-CH$_3$), 0.94 (multiple overlapping multiplets consisting of both CH$_3$ and CH$_2$), 3.08 (s, 5H, CH$_3$/CH$_2$). 3.51 (m, 1H, 3-CH) ppm.

$^{13}$C NMR (62.9 MHz) δ=11.0 (CH$_3$, C18), 12.7, 17.3 (CH$_3$, C21), 20.4 (CH$_2$, C11), 21.8 (CH$_3$, C19), 26.1 (CH$_2$, C7), 29.6 (CH$_2$, C2), 34.1 (C, C10), 35.4 (CH, C20), 35.7 (CH$_2$, C1), 40.0 (CH$_2$, C12), 40.4 (CH, C9), 42.0 (CH, C5), 42.4 (C, C13), 49.8, 55.9 (CH, C17), 56.4 (CH, C14), 70.8 (CH, C3), 175.7 (CO, C24) ppm.

IR=3449 (OH), 2921 (alkyl), 2857 (alkyl), 1641 (C=O), 1548, 1445, 1364, 1036 ($R_2CH-OH$) $cm^{-1}$.

MS (+ESI) m/z=Found 531.4880 M$^+$; calculated for $C_{34}H_{63}N_2O_2$ 531.4884; 0.8 ppm.

Synthesis of (4R)-4-[(3R,10S,13R,17R)-3-hydroxy-10,13-dimethyl-2,3,4,5,6,7,8,9,11,12,14,15,16,17-tetradecahydro-1H-cyclopenta[a]phenanthren-17-yl]-1-[4-(2-hydroxyethyl)-4-[(4-vinylphenyl)methyl]piperazin-4-ium-1-yl]pentan-1-one chloride (143)

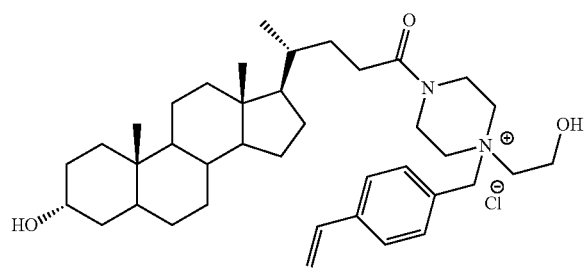 [SMILES: C=Cc1ccc(C[N+]2(CCO)CCN(C(=O)CC[C@@H](C)[C@H]3CCC4C5CCC6C[C@H](O)CC[C@]6(C)C5CC[C@@]43C)CC2)cc1 ; [Cl-]]

Compound 118 (0.2 g 0.0004 mol) was dissolved in chloroform (5 mL). Vinyl benzyl chloride (0.31 mL, 0.002 mol) was added and the solution was stirred overnight at ambient temperature. The resulting precipitate was collected by vacuum filtration and was dried overnight in a desiccator. The product was an off-white solid.

Yield; 0.1 g, 0.0001 mol, 38%.

Melting point: 143.6-146.0° C.

$^1$H NMR (MeOD) (250 MHz) δ=0.680 (s, 3H, 18-$CH_3$), 0.94 (s, 3H, 19-$CH_3$), 3.61 (multiple overlapping multiplets, 6H, $CH_2$), 5.37 (d, 1H, =CH—, J=12.5), 5.90 (d, 1H, =CH, J=17.5), 6.80 (dd, 1H, =CH, J=12.5), 7.59 (broad s, 4H, Ar—CH) ppm.

$^{13}$C NMR (62.9 MHz) δ=12.5 ($CH_3$, C18), 18.9 ($CH_3$, C21), 21.9 ($CH_2$, C11), 23.9 ($CH_3$, C19), 25.3 ($CH_2$, C15), 27.6 ($CH_2$, C7), 28.3 ($CH_2$, C6), 29.3 ($CH_2$, C16), 30.6 ($CH_2$, C2), 31.2 ($CH_2$, C22), 32.2 ($CH_2$, C23), 35.6 (C, C10), 36.4 (CH, C20), 36.8 ($CH_2$, C1), 37.2 (CH, C8), 40.6 ($CH_2$, C12), 41.5 (CH, C9), 41.9 (CH, C5), 43.5 (C, C13), 56.5 (CH, C17), 57.4 (CH, C14), 57.9 (CH, $CH_2$), 58.8 ($CH_2$) 67.1 (CH) 72.4 (CH, C3), 116.7 (CH), 127.2 (CH), 128.0 (CH), 134.9 (CH), 137.0 (CH), 141.6 (CH), 174.8 (CO, C24) ppm.

IR=3283 (OH), 2925 (alkyl), 2857 (alkyl), 1616 (C=O), 1445, 1044 ($R_2CH-OH$) $cm^{-1}$.

MS (ES) m/z=Found 605.4669 M$^+$; calculated for $C_{39}H_{61}N_2O_3$ 605.4677; 1.3 ppm.

Germination Tests

Many of the synthesised compounds were tested for their germinating and antimicrobial abilities against *C. difficile*. Due to the insolubility of some of the compounds in water, DMSO, ethanol and methanol were used to dissolve the compounds.

Methods

The *C. difficile* reference strain, NCTC 11204 and *C. difficile* ribotype 027 (R20291) (Anaerobic Reference Laboratory, Cardiff, UK) were used during testing.

Preparation of Spore Suspensions

Spore suspensions of *C. difficile* were prepared following the method proposed by Shetty et al. (1999). Briefly, Columbia base agar plates were inoculated with the relevant strain of *C. difficile* and incubated for 72 hours anaerobically at 37° C. (MiniMACS anaerobic cabinet, Don Whitley Scientific, Shipley, UK). Then, the plates were removed and left or 24 hours in aerobic conditions at room temperature. Colonies were then harvested into 20 mL of 50% (w/v) ethanol and 50% saline, and vortex thoroughly. These were stored at 4° C. until needed.

All experiments were performed in triplicate using spore suspensions containing $1 \times 10^7$ CFU $mL^{-1}$ spores of *C. difficile* NCTC 11204 and ribotype 027.

Before use, 1 mL of spores were centrifuged at 13000 rpm for 10 minutes (Spectrafuge 24D; Labnet, Woodbridge, USA). The supernatant was discarded, and the pellet resuspended in 1 mL sterile distilled water and vortex mixed thoroughly.

Germination solutions were prepared using 2% (w/v) of the compound in diluent (DMSO, ethanol, methanol, water) plus double strength thioglycollate medium (Oxoid, UK).

Heat Shock Method

For the heat shock method, 100 μl spores were exposed to 100 μl of the germination solution and incubated at room temperature in air for 1 hour. The entire 200 μl sample was then added to 800 μl sterile distilled water to dilute out the germinant to ineffective concentrations. Samples were placed on heat at 70° C. for 20 minutes to eliminate any germinated, metabolically active spores. Control samples were kept on ice. Solutions were then diluted accordingly using sterile distilled water, and cultured onto fastidious anaerobic agar (Lab M, Bury, UK), supplemented with 0.1% (w/v) sodium taurocholate (ST) and 5% (w/v) defibrinated horse blood using the Miles and Misra method (Miles et al., 1938). These were then incubated anaerobically for 48 hours at 37° C. (MiniMACS anaerobic cabinet, Don Whitley Scientific, Shipley, UK) and the CFU $mL^{-1}$ counted.

| Germination results for strains 11204 and 027 | | | | |
|---|---|---|---|---|
| Compound number | Compound name | Structure | >1 log reduction on heat | >1 log reduction on ice |
| 4 | 3-cholanamidopropyl-allyl-dimethyl-ammonium bromide | | yes | X |

-continued

| Compound number | Compound name | Structure | >1 log reduction on heat | >1 log reduction on ice |
|---|---|---|---|---|
| 50 | N-[2-(1-benzylpyrrolidin-1-ium-1-yl)ethyl] cholanamide bromide | 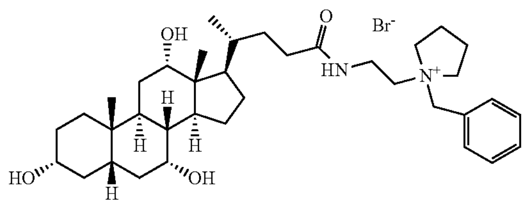 | yes | yes |
| 29 | 3-cholan amidopropyl-hexyl-dimethyl-ammonium iodide | 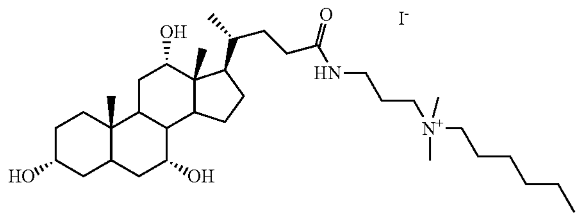 [SMILES: CCCCCC[N+](C)(C)CCCNC(=O)CC[C@@H](C)[C@H]1CCC2C3C(C[C@H](O)[C@@]21C)[C@@]1(C)CC[C@@H](O)CC1C[C@H]3O ; [I-]] | yes | X |
| 45 | N-[2-(1-propylpyrrolidin-1-ium-1-yl)ethyl] cholanamide iodide | 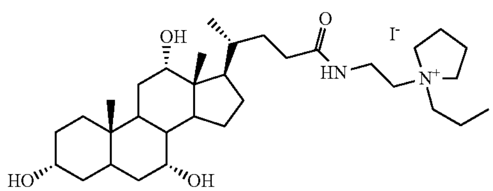 [SMILES: CCC[N+]1(CCNC(=O)CC[C@@H](C)[C@H]2CCC3C4C(C[C@H](O)[C@@]32C)[C@@]2(C)CC[C@@H](O)CC2C[C@H]4O)CCCC1 ; [I-]] | yes | yes |
| 16 | N-octadecyl cholanamide | 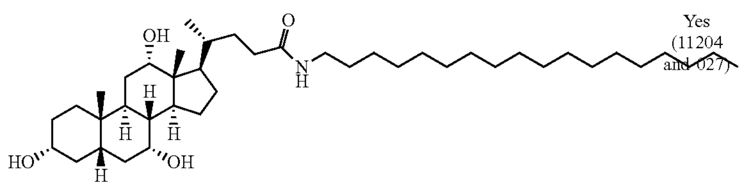 | Yes (11204 and 027) | X |
| 7 | N-[3-(dibutylamino) propyl] cholanamide | 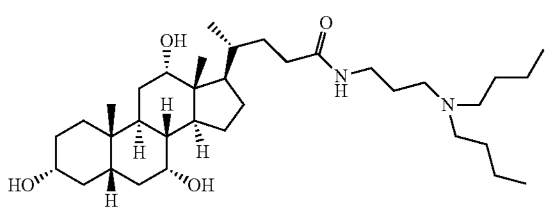 | Yes (11204) | Yes (11204) |
| 2 | cholic acid benzyl amide | 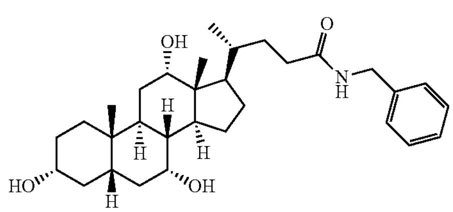 | X | Yes (11204) |
| 2/150 | | 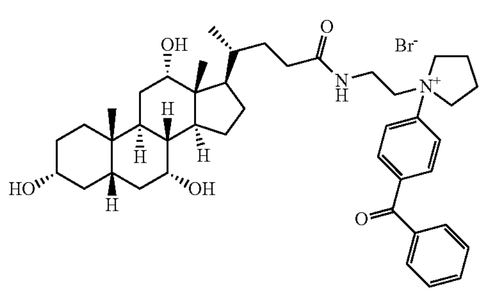 | X | Yes (11204) |

| Compound number | Compound name | Structure | >1 log reduction on heat | >1 log reduction on ice |
|---|---|---|---|---|
| 2/148 | | 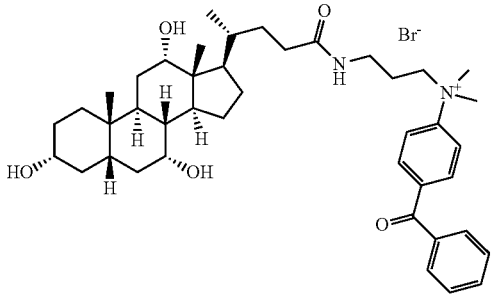 | Yes (027) | x |
| 10 | N-(2-pyrrolidin-1-ylethyl) cholanamide | 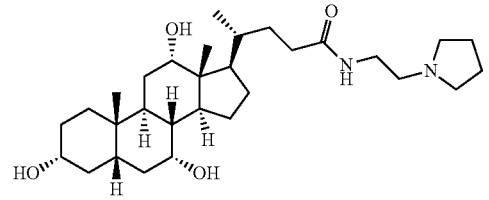 | Yes (11204) | X |

The results from the table above show the compounds that gave a 1 log reduction or more between the initial spore count and the spore count after the heat and ice treatment. A reduction in the heat count suggests the compound is a germinant, whereas a reduction in the ice suggests a sporicide or a germinant/antimicrobial compound.